US008257941B2

(12) United States Patent
Sakurada et al.

(10) Patent No.: US 8,257,941 B2
(45) Date of Patent: Sep. 4, 2012

(54) METHODS AND PLATFORMS FOR DRUG DISCOVERY USING INDUCED PLURIPOTENT STEM CELLS

(75) Inventors: Kazuhiro Sakurada, Yokohama (JP); Kenneth J. Seidenman, San Diego, CA (US)

(73) Assignee: Kyoto University, Kyoto (JP)

( * ) Notice: Subject to any disclaimer, the term of this patent is extended or adjusted under 35 U.S.C. 154(b) by 151 days.

(21) Appl. No.: 12/484,163

(22) Filed: Jun. 12, 2009

(65) Prior Publication Data

US 2009/0324559 A1 Dec. 31, 2009

Related U.S. Application Data

(63) Continuation-in-part of application No. 12/157,967, filed on Jun. 13, 2008.

(60) Provisional application No. 61/040,646, filed on Mar. 28, 2008, provisional application No. 61/061,592, filed on Jun. 13, 2008, provisional application No. 61/061,594, filed on Jun. 13, 2008.

(30) Foreign Application Priority Data

| Jun. 15, 2007 | (JP) | ................................ 2007-159382 |
| Nov. 20, 2007 | (WO) | ................. PCT/EP2007/010019 |
| Jun. 13, 2008 | (WO) | ................. PCT/EP2008/005047 |
| Jun. 13, 2008 | (WO) | ................. PCT/IB2008/002540 |

(51) Int. Cl.
*C12N 15/00* (2006.01)
(52) U.S. Cl. .......................................... 435/29; 435/377
(58) Field of Classification Search .......................... None
See application file for complete search history.

(56) References Cited

U.S. PATENT DOCUMENTS

| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Hasegawa et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |
| 6,013,517 A | 1/2000 | Respess et al. |
| 6,017,735 A | 1/2000 | O'hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |
| 6,203,975 B1 | 3/2001 | Wilson et al. |
| 6,251,398 B1 | 6/2001 | O'Hare et al. |
| 6,255,071 B1 | 7/2001 | Beach et al. |
| 6,312,948 B1 | 11/2001 | Cohen-haguenauer |
| 6,312,949 B1 | 11/2001 | Sakurada et al. |
| 6,333,195 B1 | 12/2001 | Respess et al. |
| 6,365,352 B1 | 4/2002 | Yerramilli et al. |
| 6,395,546 B1 | 5/2002 | Zobel et al. |
| 6,451,595 B1 | 9/2002 | Kim et al. |
| 6,485,959 B1 | 11/2002 | Demetriou et al. |
| 6,521,453 B1 | 2/2003 | Crameri et al. |
| 6,521,455 B2 | 2/2003 | O'Hare et al. |
| 6,605,275 B1 | 8/2003 | Boyse et al. |
| 6,660,514 B1 | 12/2003 | Zolotukhin et al. |
| 6,773,920 B1 | 8/2004 | Dalby et al. |
| 6,833,269 B2 | 12/2004 | Carpenter |

(Continued)

FOREIGN PATENT DOCUMENTS

AU      2008201280 A1    4/2008

(Continued)

OTHER PUBLICATIONS

Kozarsky et al. Adenovirus-Mediated Correction of the Genetic Defect in Hepatocytes from Patients with Familial Hypercholesterolemia Somatic Cell Molecular Genetics, 1993, vol. 19, pp. 449-458.*
Brimble et al. Karyotypic Stability, Genotyping, Differentiation, Feeder-Free Maintenance, and Gene Expression Sampling in Three Human Embryonic Stem Cell Lines Derived Prior to Aug. 9, 2001 Stem Cells Develop., 2004, vol. 13, pp. 585-596.*
Bosman et al. Progress Toward the Clinical Application of Autologous Induced Pluripotent Stem Cells and Gene Repair Therapy for Treatment of Familial Hypercholesterolemia. The International Liver Congress 2011, 2011, abstract.*
International Search Report and Written Opinion issued in PCT/JP2011/051685.

(Continued)

*Primary Examiner* — Deborah Crouch
(74) *Attorney, Agent, or Firm* — Knobbe Martens Olson & Bear LLP

(57) ABSTRACT

The present invention involves methods for identifying an agent that corrects a phenotype associated with a health condition or a predisposition for a health condition. The invention also involves methods for identifying a diagnostic cellular phenotype, determining the risk of a health condition in a subject, methods for reducing the risk of drug toxicity in a human subject, and methods for identifying a candidate gene that contributes to a human disease. The invention also discloses human induced pluripotent stem cell lines.

11 Claims, 7 Drawing Sheets

U.S. PATENT DOCUMENTS

| | | |
|---|---|---|
| 6,841,535 B2 | 1/2005 | Divita et al. |
| 6,872,528 B2 | 3/2005 | Klatzmann et al. |
| 6,875,578 B2 | 4/2005 | Giuliano et al. |
| 6,881,825 B1 | 4/2005 | Robbins et al. |
| 6,910,434 B2 | 6/2005 | Lundgren et al. |
| 6,995,009 B1 | 2/2006 | Kitamura et al. |
| 7,029,913 B2 | 4/2006 | Thomson |
| 7,030,292 B2 | 4/2006 | Yan et al. |
| 7,070,994 B2 | 7/2006 | Barber et al. |
| 7,250,255 B2 | 7/2007 | Yamanaka |
| 7,439,064 B2 | 10/2008 | Thomson et al. |
| 2002/0090722 A1 | 7/2002 | Dominko et al. |
| 2002/0174013 A1 | 11/2002 | Freeman et al. |
| 2003/0003574 A1 | 1/2003 | Toma et al. |
| 2003/0044976 A1 | 3/2003 | Dominko et al. |
| 2003/0161817 A1 | 8/2003 | Young et al. |
| 2004/0048297 A1 | 3/2004 | Scherf |
| 2004/0137460 A1 | 7/2004 | Yamanaka et al. |
| 2005/0019801 A1 | 1/2005 | Rubin et al. |
| 2005/0026133 A1 | 2/2005 | Nakatsuji et al. |
| 2005/0079606 A1 | 4/2005 | Tamaki et al. |
| 2005/0130144 A1 | 6/2005 | Nakatsuji et al. |
| 2006/0030041 A1 | 2/2006 | Furcht et al. |
| 2006/0084172 A1 | 4/2006 | Muller et al. |
| 2006/0088599 A1 | 4/2006 | Prasad et al. |
| 2006/0095319 A1 | 5/2006 | Cardwell |
| 2006/0110830 A1 | 5/2006 | Dominko et al. |
| 2006/0222636 A1 | 10/2006 | Rambukkana |
| 2006/0292620 A1 | 12/2006 | Yamanaka et al. |
| 2007/0033061 A1 | 2/2007 | Patten et al. |
| 2007/0053884 A1 | 3/2007 | Suda et al. |
| 2007/0155013 A1 | 7/2007 | Akaike et al. |
| 2007/0202592 A1 | 8/2007 | Kitagawa et al. |
| 2007/0254884 A1 | 11/2007 | Chen et al. |
| 2007/0269790 A1 | 11/2007 | Amit et al. |
| 2008/0003560 A1 | 1/2008 | Nakatsuji et al. |
| 2008/0076176 A1 | 3/2008 | Dominko et al. |
| 2008/0085555 A1 | 4/2008 | Asahara et al. |
| 2008/0132803 A1 | 6/2008 | Friedlander |
| 2008/0171358 A1 | 7/2008 | Perrault |
| 2008/0171385 A1 | 7/2008 | Bergendahl et al. |
| 2008/0206865 A1 | 8/2008 | Zhang et al. |
| 2008/0233610 A1 | 9/2008 | Thomson et al. |
| 2008/0274914 A1 | 11/2008 | Yamanaka |
| 2008/0280362 A1 | 11/2008 | Jaenisch et al. |
| 2008/0293143 A1 | 11/2008 | Lin et al. |
| 2008/0299548 A1 | 12/2008 | Yamanaka |
| 2009/0047263 A1 | 2/2009 | Yamanaka et al. |
| 2009/0068742 A1 | 3/2009 | Yamanaka et al. |
| 2009/0191159 A1 | 7/2009 | Sakurada et al. |
| 2009/0191171 A1 | 7/2009 | Ma |
| 2009/0227032 A1 | 9/2009 | Yamanaka |
| 2009/0299763 A1 | 12/2009 | Sakurada et al. |
| 2009/0304646 A1 | 12/2009 | Sakurada et al. |
| 2009/0324559 A1 | 12/2009 | Sakurada |
| 2010/0003757 A1 | 1/2010 | Mack |
| 2010/0021437 A1 | 1/2010 | Isacson |
| 2010/0062533 A1 | 3/2010 | Yamanaka |
| 2010/0062534 A1 | 3/2010 | Hochedlinger |
| 2010/0075421 A1 | 3/2010 | Yamanaka |
| 2010/0093090 A1 | 4/2010 | Deng |
| 2010/0105100 A1 | 4/2010 | Sakurada et al. |
| 2010/0120069 A1 | 5/2010 | Sakurada et al. |
| 2010/0144031 A1 | 6/2010 | Jaenisch |
| 2010/0184051 A1 | 7/2010 | Hochedlinger |
| 2010/0184227 A1 | 7/2010 | Thomson |
| 2010/0210014 A1 | 8/2010 | Yamanaka |
| 2010/0216236 A1 | 8/2010 | Yamanaka |
| 2010/0221827 A1 | 9/2010 | Jaenisch |
| 2010/0233804 A1 | 9/2010 | Zhou |
| 2010/0240090 A1 | 9/2010 | Sakurada et al. |
| 2010/0267135 A1 | 10/2010 | Sakurada et al. |
| 2010/0279404 A1 | 11/2010 | Yamanaka |
| 2011/0039332 A1 | 2/2011 | Sakurada et al. |

FOREIGN PATENT DOCUMENTS

| | | |
|---|---|---|
| CN | 101250502 A | 8/2008 |
| CN | 101550428 A | 10/2009 |
| EP | 1384775 A1 | 1/2004 |
| EP | 1403366 A1 | 3/2004 |
| EP | 1970446 A1 | 9/2008 |
| EP | 2096169 A1 | 9/2009 |
| JP | 2-227075 | 9/1990 |
| JP | 2002-065261 | 3/2002 |
| JP | 2003-009854 | 1/2003 |
| JP | 2004-161682 A | 6/2004 |
| JP | 2005-095027 | 4/2005 |
| JP | 2005-359537 | 12/2005 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 00/18885 A1 | 4/2000 |
| WO | WO 00/23567 A2 | 4/2000 |
| WO | WO 00/27995 A1 | 5/2000 |
| WO | WO 00/23567 A3 | 7/2000 |
| WO | WO 00/73423 A1 | 12/2000 |
| WO | WO 01/21767 A2 | 3/2001 |
| WO | WO 01/34776 A1 | 5/2001 |
| WO | WO 01/51616 A2 | 7/2001 |
| WO | WO 01/21767 A3 | 8/2001 |
| WO | WO 01/81549 A2 | 11/2001 |
| WO | WO 02/00871 A2 | 1/2002 |
| WO | WO 02/061033 A2 | 8/2002 |
| WO | WO 02/00871 A3 | 10/2002 |
| WO | WO 02/086129 A1 | 10/2002 |
| WO | WO 02/086134 A2 | 10/2002 |
| WO | WO 02/097090 A1 | 12/2002 |
| WO | WO 03/018780 A1 | 3/2003 |
| WO | WO 02/086134 A3 | 12/2003 |
| WO | WO 2004/081205 A1 | 9/2004 |
| WO | WO 2005/080598 A1 | 9/2005 |
| WO | WO 2005/090557 A1 | 9/2005 |
| WO | WO 2006/035741 A1 | 4/2006 |
| WO | WO 2006/084229 A2 | 8/2006 |
| WO | WO 2006/088867 A2 | 8/2006 |
| WO | WO 2007/026255 A2 | 3/2007 |
| WO | WO 2007/054720 A1 | 5/2007 |
| WO | WO 2007/069666 A1 | 6/2007 |
| WO | WO 2007/097494 A1 | 8/2007 |
| WO | WO 2008/030610 A2 | 3/2008 |
| WO | WO 2008/035110 A1 | 3/2008 |
| WO | WO 2008/038148 A2 | 4/2008 |
| WO | WO 2008/089351 A1 | 7/2008 |
| WO | WO 2008/105566 A1 | 9/2008 |
| WO | WO 2008/105630 A1 | 9/2008 |
| WO | WO 2008/116213 A1 | 9/2008 |
| WO | WO 2008/118820 A2 | 10/2008 |
| WO | WO 2008/124133 A1 | 10/2008 |
| WO | WO 2008/118820 A3 | 11/2008 |
| WO | WO 2008/150814 A2 | 12/2008 |
| WO | WO 2008/151058 A2 | 12/2008 |
| WO | WO 2008/151058 A3 | 1/2009 |
| WO | WO 2009/006997 A1 | 1/2009 |
| WO | WO 2009/007852 A2 | 1/2009 |
| WO | WO 2008/150814 A3 | 2/2009 |
| WO | WO 2009/023161 A1 | 2/2009 |
| WO | WO 2009/032194 A1 | 3/2009 |
| WO | WO 2009/032456 A2 | 3/2009 |
| WO | WO 2009/032456 A3 | 4/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/096614 A1 | 6/2009 |
| WO | WO 2009/007852 A3 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2009/149233 A1 | 12/2009 |
| WO | WO 2010/013359 A1 | 2/2010 |
| WO | WO 2010/048567 A1 | 4/2010 |

OTHER PUBLICATIONS

European Examination Report on EP 07 856 194.1, issued Sep. 29, 2011.
A reprogramming rush. Editorial. Nature. Mar. 27, 2008. 452:388. Published online Mar. 26, 2008.
Adachi et al. Role of SOX2 in maintaining pluripotency of human embryonic stem cells. Genes Cells. May 2010; 15(5):455-70.
Adhikary et al. Transcriptional regulation and transformation by Myc proteins. Nat Rev Mol Cell Biol. Aug. 2005;6(8):635-45.
Akimov et al., Bypass of Senescence, Immortalization, and Transformation of Human Hematopoietic Progenitor Cells, Stem Cells 23:1423-33, 2005.
Amsellem et al., Ex vivo Expansion of Human Hematopoietic Stem Cells by Direct Delivery of the HOXB4 Homeoprotein, Nat. Med. 9(11):1423-27, 2003.
Asahi Shimbun Weekly AERA, The Novel Pluripotent Cells Established by Professor Yamanaka of Kyoto University May change Medical Care, pp. 72-73, Dec. 24, 2009, along with a partial English language translation thereof.
Avilion et al., Multipotent Cell Lineages in Early Mouse Development Depend on SOX2 Function, Genes Dev. 17:126-40, 2003.
Bagutti et al. Differentiation of embryonal stem cells into keratinocytes: comparison of wild-type and beta 1 integrin-deficient cells. Dev Biol. Oct. 10, 1996; 179(1): 184-96.
Bang et al., Deconstructing Pluripotency, Science 320:58-59, 2008.
Barrett et al. NCBI GEO: mining tens of millions of expression profiles—database and tools update. Nucleic Acids Res. Jan. 2007;35(Database issue):D760-S.
Barrett et al., Activation Domains of L-Myc and c-Myc Determine Their Transforming Potencies in Rat Embryo Cells, Mol. Cell. Biol. 12(7):3130-37, 1992.
Bayani et al. Multi-color Fish techniques. Curr. Protoc. Cell Biol. 2004; Chapter 22:Unit 22.5.
Becker-Hapak et al. Protein transduction: generation of full-length transducible proteins using the TAT system. Curr Protoc Cell Biol. May 2003;Chapter 20: Unit 20.2.
Belmonte et al. "Induced pluripotent stem cells and reprogramming: seeing the science through the hype." Nat Rev Genet. Dec. 2009;10(12):878-83.
Benetti et al., A Mammalian microRNA Cluster Controls DNA Methylation and Telomere Recombination Via Rbl2-Dependent Regulation of DNA Methyltransferases, Nat. Struct. Mol. Biol. 15(3):268-79, published online Mar. 2, 2008.
Ben-Shushan et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4): 1866-78, 1998.
Berg et al. An argument against a role for Oct4 in somatic stem cells. Cell Stem Cell. Oct. 11, 2007;1(4):359-60.
Bibel et al., "Differentiation of mouse embryonic stem cells into a defined neuronal lineage," Nature Neuroscience, 2004, vol. 7, pp. 1003-1009.
Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.
BioPorter™ Gene Therapy System, Inc., Wako Bio Window 40:7, 2002.
BioPorter™ Protein Delivery Reagent From www.biocarta.com, 2002.
Birnbaum et al. Slicing across Kingdoms: Regeneration in Plants and Animals. Cell. Feb. 22, 2008; 132(4):697-710.
Birrer et al., L-myc Cooperates With ras to Transform Primary Rat Embryo Fibroblasts, Mol. Cell. Biol. 8(6):2668-73, 1988.
Blackwood et al., Max: A Helix-Loop-Helix Zipper Protein That Forms a Sequence-Specific DNA-Binding Complex With Myc, Science 251(499):1211-17, 1991.
Block et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.
Boquest et al. Epigenetic programming of mesenchymal stem cells from human adipose tissue. Stem Cell Rev. 2006;2(4):319-29.
Bortvin et al., Incomplete Reactivation of Oct4-Related Genes in Mouse Embryos Cloned From Somatic Nuclei, Development 130:1673-80, 2003.
Boyer et al. Core Transcriptional Regulatory Circuitry in Human Embryonic Stem Cells. Cell. 2005;122(6):947-956.
Brambrink et al. Sequential Expression of Pluripotency Markers during Direct Reprogramming of Mouse Somatic Cells. Cell Stem Cell. 2008; 2, 151-159.
Brough et al., An Essential Domain of the c-Myc Protein Interacts With a Nuclear Factor That is Also Required for E1A-Mediated Transformation, Mol. Cell. Biol. 15(3):1536-44, 1995.
Campbell et al. Phosphonate Ester Synthesis Using a Modified Mitsunobu Condensation. J. Org. Chem.1994;59: 658-660.
Carey et al., "Reprogramming of murine and human somatic cells using a single polycistronic vector," Proc. Natl. Acad. Sci. USA, Jan. 6, 2009, vol. 106(1), pp. 157-162, Epub. Dec. 24, 2008. Erratum in: Proc. Natl. Acad. Sci. USA, Mar. 31, 2009, Vol.
Cartwright et al. LIF/STAT3 controls ES cell self-renewal and pluripotency by a Myc-dependent mechanism. Development. Mar. 2005; 132(5):885-96.
Chambers et al., Functional Expression Cloning of Nanog, A Pluripotency Sustaining Factor in Embryonic Stem Cells, Cell 113:643-55, 2003.
Chang et al. The c-Myc transactivation domain is a direct modulator of apoptotic versus proliferative signals. Mol Cell Biol. Jun. 2000;20(12):4309-19.
Chang et al., Embryonic Stem Cells/Induced Pluripotent Stem Cells, Stem Cells, 2009, vol. 27, pp. 1042-1049.
Check, E., Simple Recipe Gives Adult Cells Embryonic Powers, Nature 442:11, Jul. 6, 2006.
Chen et al. Analogous Organic-Synthesis of Small-Compound Libraries—Validation of Combinatorial Chemistry in Small-Molecule Synthesis. Journal of the American Chemical Society. 1994;116(6): 2661-2662.
Chen et al. From stem cells to oligodendrocytes: prospects for brain therapy. Stem Cell Rev. Dec. 2007;3(4):280-8.
Cheng et al., Mammalian Grb2 Regulates Multiple Steps in Embryonic Development and Malignant Transformation, Cell 95:793-803, 1998.
Cline et al. Randomize Gene Sequences with New PCR Mutagenesis Kit. Strategies Newsletter. 2000; 13: 157-161.
Cohen et al., "Ooplasmic Transfer in Mature Human Oocytes," Molecular Human Reproduction, 1998, vol. 4, pp. 269-280.
Correction printed in Nature 447:897, Jun. 21, 2007.
Cosmo Bio News 49:5, 2005 (catalog of ES cell culture medium).
Cowan et al. Nuclear Reprogramming of Somatic Cells After Fusion with Human Embryonic Stem Cells. Science, 2005, vol. 309, pp. 1369-1374.
Cowan et al., Derivation of Embryonic Stem-Cell Lines From Human Blastocysts, N. Engl. J. Med. 350:1353-56, 2004.
Cowling et al. Mechanism of transcriptional activation by the Myc oncoproteins. Semin Cancer Biol. Aug. 2006; 16(4):242-52.
Cyranoski et al. Simple switch turns cells embryonic. Nature. 2007; 447:618-619.
Cyranoski. Japan ramps up patent effort to keep iPS lead. Nature. 2008; 453(7198):962-3.
Daley, et al., "Broader implications of defining standards for the pluripotency of iPSCs." Cell Stem Cell. Mar 6, 2009;4(3):200-1; author reply 202.
Dang et al., The Biology of the Mammalian Kruppel-Like Family of Transcription Factors, Int. J. Biochem. Cell Biol. 32:1103-21, 2000.
Deb, et al. Embryonic Stem Cells: From Markers to Market. Feb. 2008; 11(1): 19-37.
Dewitt et al. "Diversomers": an approach to nonpeptide, nonoligomeric chemical diversity. Proc Natl Acad Sci USA. Aug. 1, 1993;90(15):6909-13.
Do et al., "Nuclei of Embryonic Stem Cells Reprogram Somatic Cells," Stem Cells, 2004, vol. 22, pp. 941-949.
Ehrich et al. Quantitative high-throughput analysis of DNA methylation patterns by base-specific cleavage and mass spectrometry. Proc Natl Acad Sci USA. Nov 1, 2005; 102(44): 15785-90.
Eisen et al. Cluster analysis and display of genome-wide expression patterns. Dec. 8, 1998;95(25): 14863-14868.

Essentials of Stem Cell Biology, R. Lanza et al. Ed., 2006, Elsevier Academic Press, pp. 266-267.

Evans et al. Krüppel-like factor 4 is acetylated by p300 and regulates gene transcription via modulation of histone acetylation. J Biol Chem. Nov. 23, 2007;282(47): 33994-4002.

Evans et al., Establishment in Culture of Pluripotential Cells From Mouse Embryos, Nature 292:154-56, 1981.

Examination Report issued in Australian Patent Application No. 2006325975, Apr. 18, 2011.

Extended European Search Report issued in connection with European Patent Application No. 10154819.6, Jun. 10, 2010.

Extended European Search Report issued in connection with European Patent Application No. EP 06834636.0, Mar. 11, 2009.

Extended European Search Report issued in connection with European Patent Application No. EP 10154817.0, Jun. 10, 2010.

Extended European Search Report issued in connection with European Patent Application No. EP 10154821.2, Jun. 10, 2010.

Feng et al., Reprogramming of Fibroblasts Into Induced Pluripotent Stem Cells With Orphan Nuclear Receptor Esrrb, Nature Cell Biology 11:197-203, 2009.

Ferrer-Costa et al. PMUT: a web-based tool for the annotation of pathological mutations on proteins. Bioinformatics. Jul. 15, 2005;21(14):3176-8.

Forsyth et al. Human Embryonic Stem Cell Telomere Length Impacts Directly on Clonal Progenitor Isolation Frequency. Rejuvenation Research. Feb. 2008;11(1):5-17.

Gallop et al. Applications of combinatorial technologies to drug discovery. 1. Background and peptide combinatorial libraries. J Med Chem. Apr. 29, 1994;37(9): 1233-51.

Ghaleb et al. Krüppel-like factors 4 and 5: the yin and yang regulators of cellular proliferation. Cell Res. Feb. 2005; 15(2):92-6.

Goswami et al. Embryonic stem cell therapy. IDrugs. Oct. 2007;10(10):713-9.

Griffiths-Jones et al., miRBase: Tools for microRNA Genomics, Nucleic Acids Research 36:D154-D158, published online Nov. 8, 2007.

Gu et al. Opposite regulation of gene transcription and cell proliferation by c-Myc and Max. Proc Natl Acad Sci USA. Apr. 1, 1993;90(7):2935-9.

Ha et al. Cryopreservation of human embryonic stem cells without the use of a programmable freezer. Hum Reprod. Jul. 2005;20(7): 1779-85.

Hakelien et al. Reprogramming Fibroblasts to Express T-Cell Functions Using Cell Extracts. Nature Biotechnology, May 2002, vol. 20, pp. 460-466.

Hanna et al., Direct Reprogramming of Terminally Differentiated Mature B Lymphocytes to Pluripotency, Cell 133:250-264, Apr. 17, 2008.

Hanna et al., Treatment of Sickle Cell Anemia Mouse Model With iPS Cells Generated From Autologous Skin, Science4 318(5858):1920-23, published online Dec. 6, 2007.

Hasegawa et al., Efficient Multicistronic Expression of a Transgene in Human Embryonic Stem Cells, Stem Cells 25:1707-12,. 2007.

Hatfield et al., Stem Cell Division is Regulated by the microRNA Pathway, Nature 435(7044):974-978, 2005.

Heng et al. Incorporating protein transduction domains (PTD) within intracellular proteins associated with the 'stemness' phenotype. Novel use of such recombinant 'fusion' proteins to overcome current limitations of applying autologous adult stem cells in Med. Hypotheses, 2005, vol. 64, pp. 992.

Herold et al., Negative Regulation of the Mammalian UV Response by Myc Through Association with Miz-1, Mol. Cell 10(3):509-21, 2002.

Highfield, R. Dolly creator Proflan Wilmut shuns cloning. Available at http://www.telegraph.co.uk/earth/main.jhtml?xml=/earth/2007/11/16/scidolly116.xml. Accessed Nov. 12, 2008.

Hong et al., "Suppression of induced pluripotent stem cell generation by the p53-p21 pathway." Nature. Aug 27, 2009;460(7259):1132-5.

Horikawa et al., Differential Cis-Regulation of Human Versus Mouse TERT Gene Expression in vivo: Identification of a Human-Specific Repressive Element, proc. Natl. Acad. Sci. U.S.A. 102(51):18437-42, 2005.

Houbaviy et al., Embryonic Stem Cell-Specific MicroRNAs, Developmental Cell 5(2):351-58, 2003.

Hsiao et al., Marking Embryonic Stem Cells With a 2A Self-Cleaving Peptide: A NKX2-5 Emerald GFP BAC Reporter, PLoS ONE 3(7):e2532, 2008.

Huangfu et al. Efficient Induction of Pluripotent Stem Cells Using Small Molecule Compounds. Companion manuscript to U.S. Appl. No. 61/029,287, 2008.

Huangfu et al., Induction of Pluripotent Stem Cells by Defined Factors is Greatly Improved by Small-Molecule Compounds, Nature Biotechnology 26(7):795-97, 2008.

Huangfu et al., Induction of Pluripotent Stem Cells From Primary Human Fibroblasts With Only Oct4 and Sox 2, Nature Biotechnology 26:1269-1275, 2008.

Humphries, C., Reprogrammed Stem Cells Work on Parkinson's: A Study in Rodents Suggests that Skin Cells Can Be Transformed into Neurons to Treat Neurodegeneration, Technology Review, published by MIT, Apr. 8, 2008: http://www.technologyreview.com/printer.

Hwang et al., Evidence of Pluripotent Human Embryonic Stem Cell Line Derived From a Cloned Blastocyst, Science 303:1669-74, 2004.

Hwang et al., Patient-Specific Embryonic Stem Cells Derived From Human SCNT Blastocysts, Science 308:1777-83, 2005.

Itskovitz-Eldor et al., Differentiation of Human Embryonic Stem Cells Into Embryoid Bodies Comprising the Three Embryonic Germ Layers, Mol. Med. 6(2):88-95, 2000.

Jaenisch et al. Stem Cells, the Molecular Circuitry of Pluripotency and Nuclear Reprogramming. Cell. Feb. 22, 2008; 132(4):567-582.

Jahagirdar et al. Multipotent adult progenitor cell and stem cell plasticity. Stem Cell Rev. 2005;1(1):53-9.

Jiang et al. A core Klf circuitry regulates self-renewal of embryonic stem cells. Nat Cell Biol. Mar. 2008; 10(3):353-60.

Jiang et al. Pluripotency of mesenchymal stem cells derived from adult marrow. Nature. Jul. 4, 2002;418(6893):41-9.

Jikken Igaku (Experimental Medicine) 24:814-19, 2006, along with an English language translation thereof.

Johnston et al. Minimum requirements for efficient transduction of dividing and nondividing cells by feline immunodeficiency virus vectors. J Virol. Jun. 1999;73(6):4991-5000.

Kaji et al., Virus-Free Induction of Pluripotency and Subsequent Excision of Reprogramming Factors, Nature, Mar. 1, 2009, vol. 458, Issue 7239, pp. 771-775.

Kamachi, et at. Mechanism of regulatory target selection by the SOX high-mobility-group domain proteins as revealed by comparison of SOX1/2/3 and SOX9. Mol Cell Biol. Jan. 1999;19(1):107-20.

Kanegae et al. Efficient gene activation in mammalian cells by using recombinant adenovirus expressing site-specific Cre recombinase. Nucleic Acids Res. Oct. 11, 1995;23(19):3816-21.

Kanellopoulou et al., Dicer-Deficient Mouse Embryonic Stem Cells Are Defective in Differentiation and Centromeric Silencing, Genes & Development 19:489-501, 2005.

Kim et al. Ex vivo characteristics of human amniotic membrane-derived stem cells. Cloning Stem Cells. 2007 Winter; 9(4):581-94.

Kim et al., Generation of Human Induced Pluripotent Stem Cells by Direct Delivery of Reprogramming Proteins, Cell Stem Cell 4:472-476, 2009.

Kim et al., Oct4-Induced Pluripotency in Adult Neural Stem Cells, Cell 136:411-419, 2009.

Kim et al., Pluripotent Stem Cells Induced From Adult Neural Stem Cells by Reprogramming with Two Factors, Nature 454:656-650, 2008.

Klingemann, H. Discarded stem cells svvith a future? Expert Opin Biol Ther. Dec. 2006;6(12): 1251-4.

Knoblich, J.A. Mechanisms of Asymmetric Stem Cell Division. Cell. Feb. 22, 2008; 132(4):583-597.

Koch et al. Transduction of human embryonic stem cells by ecotropic retroviral vectors. Nucl Acids Res. 2006; 34, e120.

Kohge et al. Promotion of antigen-specific antibody production in murine B cells by a moderate increase in histone acetylation. Biochem Pharmacol. Nov. 15, 1998;56(10): 1359-64.

Kohlhase et al., Cloning and Expression Analysis of Sall4, The Murine Homologue of the Gene Mutated in Okihiro Syndrome, Cytogenet. Genome Res. 98:274-77, 2002.

Kopsidas et al. RNA mutagenesis yields highly diverse mRNA libraries for in vitro protein evolution. BMC Biotechnol. Apr. 11, 2007;7:18.

Koyanagi et al., Screening and Functional Analysis of microRNAs which involve in Reprogramming, of Murine Somatic Cells, The Journal of Biochemistry, vol. 79, No. 11 Abstract 1T-7-7 From the 80$^{th}$ Annual Meeting of the Japanese Biochemical Society, Nov. 2007.

Krosl et al., In vitro Expansion of Hematopoietic Stem Cells by Recombinant TAT-HOXB4 Protein, Nat. Med 9(11):1428-32, 2003.

Kubicek et al., Reversal of H3K9me2 by a Small-Molecule Inhibitor for the G9a Histone Methyltransferase, Molecular Cell 25:473-81, 2007.

Kuroda et al. Octamer and Sox Elements Are Required for Transcriptional cis Regulation of Nanog Gene Expression. Mol Cell Biol. Mar. 2005; 25(6):2475-2485.

Kyoto Shimbun (Japanese Newspaper) article of Apr. 16, 2008, cols. 1-3, along with a partial English language translation thereof.

Laflamme et al, Cardiomyocytes Derived From Human Embryonic Stem Cells in Pro-Survival Factors Enhance Function of Infarcted Rat Hearts, Nat. Biotechnol. 25(9):1015-24, 2007.

Laird et al. Stem Cell Trafficking in Tissue Development, Growth, and Disease. Cell. Feb. 22, 2008; 132(4):612-630.

Lanza et al. (Eds.) Essentials of Stem Cell Biology. Elsevier Academic Press. 2006. (Table of Contents only).

Lemken et al. Evidence for intercellular trafficking of VP22 in living cells. Mol Ther. Feb. 2007;15(2):310-9.

Lengner et al. The pluripotency regulator Oct4: a role in somatic stem cells? Cell Cycle. Mar. 2008;7(6):725-8.

Lewitzky et al., "Reprogramming somatic cells towards pluripotency by defined factors." Curr Opin Biotechnol. Oct. 2007;18(5):467-73.

Li et al. Small dsRNAs induce transcriptional activation in human cells. Proc Natl Acad Sci. 2006; 103, 17337-17342.

Li et al., Leukaemia Disease Genes: Large-Scale Cloning and Pathway Predictions, Nat. Genet. 23(3):348-353, 1999.

Liao et al., Enhanced Efficiency of Generating Induced Pluripotent Stem (iPS) Cells From Human Somatic Cells by a Combination of Six Transcription Factors, Cell Research 18:600-603, doi: 10.1038/cr.2008.51, published online Apr. 15, 2008.

Lin et al., Mir-302 Reprograms Human Skin Cancer Cells into a Pluripotent ES-Cell-Like State, RNA 14:1-10, 2008.

Lin-Goerke et al. PCR-based random mutagenesis using manganese and reduced dNTP concentration. Biotechniques. Sep. 1997;23(3):409-12.

Link et al. Therapeutic protein transduction of mammalian cells and mice by nucleic acid-free lentiviral nanoparticles. Nucleic Acids Res. Jan. 30, 2006;34(2):e16.

Littlewood et al. A modified oestrogen receptor ligand-binding domain as an improved switch for the regulation of heterologous proteins. Nucleic Acids Res. May 25, 1995;23(10):1686-90.

Liu, S. iPS Cells: a More Critical Review. Stem Cells Dev. Jun. 2008;17(3):391-7.

Loh et al. The Oct4 and Nanog transcription network regulates pluripotency in mouse embryonic stem cells. Nat Genet. Apr. 2006;38(4):431-40.

Loriot et al., Five New Human Cancer-Germline Genes Identified Among 12 Genes Expressed in Spermatogonia, Int. J. Cancer 105:371-76, 2003.

Loudig et al. Transcriptional co-operativity between distant retinoic acid response elements in regulation of Cyp26A1 inducibility. Biochem J. Nov. 15, 2005;392(Pt 1):241-8.

Ludwig et al. Derivation of human embryonic stem cells in defined conditions. Nat Biotechnol. Feb. 2006;24(2):185-7.

Lunde et al. Zebrafish pou5fl/pou2, homolog of mammalian Oct4, functions in the endoderm . specification cascade. Curr Biol. Jan. 6, 2004;14(1):48-55.

Lungwitz et al. Polyethylenimine-based non-viral gene delivery systems. Eur J Pharm Biopharm. Jul. 2005;60(2):247-66.

Maherali et al. Directly reprogrammed fibroblasts show global epigenetic remodeling and widespread tissue contribution. Cell Stem Cell. Jun. 7, 2007;1(1):55-70.

Marson et al., Wnt Signaling Promotes Reprogramming of Somatic Cells to Pluripotency, Cell Stem Cell 3:132-35, 2008.

Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.

Maruyama et al., Differential Roles for Sox15 and Sox2 in Transcriptional Control in Mouse Embryonic Stem Cells, J. Biol., Chem. 280(26):24371-79, 2005.

Masaki et al. Heterogeneity of pluripotent marker gene expression in colonies generated in human iPS cell induction culture. Stem Cell Research. 2008; 1:105-115.

Masaki et al. Tendency of Pluripotential marker gene expression in colonies derived from human neonatal fibroblasts induced by the human iPS cell method. Stem Cell Researchr. 2008. doi: 10.1016/j.scr.2008.01.001 (Accepted Manuscript).

Mathe et al. Computational approaches for predicting the biological effect of p53 missense mutations: a comparison of three sequence analysis based methods. Nucleic Acids Res. Mar. 6, 2006;34(5):1317-25.

Matsuda et al. STAT3 activation is sufficient to maintain an undifferentiated state of mouse embryonic stem cells. EMBO J. Aug. 2, 1999;18(15):4261-9.

McMahon et al., The Wnt-1 (int-1) Proto-Oncogene is Required for Development of a Large Region of the Mouse Brain, Cell 62:1073-85, 1990.

Meiner et al, Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-46, 1996.

Meissner et al. Direct reprogramming of genetically unmodified fibroblasts into pluripotent stem cells. Nat Biotech. 2007; 25, 1177-1181.

microRNA Jikken Purotokoru (microRNA Experimental Protocol), pp. 20-35, 2008, Yodosha Co., Ltd.

Mikkelsen et al. Dissecting direct reprogramming through integrative genomic analysis. Nature. Jul. 3, 2008;454(7200):49-55. Erratum in: Nature. 2008;454(7205):794.

Mitsui et al., The Homeoprotein Nanog is Required for Maintenance of Pluripotency in Mouse Epiblast and ES Cells, Cell 113:631-42, 2003.

Miura et al. "Variation in the safety of induced pluripotent stem cell lines." Nat Biotechnol. Aug. 2009;27(8):743-5.

Miyagishi et al. Strategies for generation of an siRNA expression library directed against the human genome. Oligonucleotides. 2003;13(5):325-33.

Miyoshi et al. Development of a self-inactivating lentivirus vector. J Virol. Oct. 1998;72(10):8150-7.

More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1.

Morgenstern et al. Advanced mammalian gene transfer: high titre retroviral vectors with multiple drug selection markers and a complementary helper-free packaging cell line. Nucleic Acids Res. Jun. 25, 1990; 18(12):3587-3596.

Morita et al. Plat-E: An Efficient and Stable System for Transient Packaging of Retroviruses, Gene Ther. 7:1063-66, 2000.

Morling et al. Enhanced transduction efficiency of retroviral vectors coprecipitated with calcium phosphate. Gene Ther. Sep. 1995;2(7):504-8.

Morrison, S.J. Stem Cells and Niches: Mechanisms that Promote Stem Cell Maintenance throughout Life. Cell. Feb. 22, 2008; 132(4):598-611.

Nagano et al., "Large-Scale Identification of Proteins Expressed in Mouse Embryonic Stem Cells," Proteomics 5:1346-1361, 2005.

Nagy et al. Embryonic stem cells alone are able to support fetal development in the mouse. Development. Nov. 1990;110(3):815-21.

Nakagawa et al., "Promotion of direct reprogramming by transformation-deficient Myc." Proc Natl Acad Sci U S A. Aug. 10, 2010;107(32):14152-7.

Nakagawa et al., Generation of Induced Pluripotent Stem Cells Without Myc From Mouse and Human Fibroblasts, Nat. Biotechnol. 26(1):101-06, published online Nov. 30, 2007.

Nakatake et al. Klf4 cooperates with Oct3/4 and Sox2 to activate the Lefty1 core promoter in embryonic stem cells. Mol Cell Biol. Oct. 2006;26(20):7772-82.

Naldini et al. In vivo gene delivery and stable transduction of nondividing cells by a lentiviral vector. Science. Apr. 12, 1996;272(5259):263-7.

Needleman et al. A general method applicable to the search for similarities in the amino acid sequence of two proteins. J Mol Biol. Mar. 1970;48(3):443-53.

Négre et al. Lentiviral vectors derived from simian immunodeficiency virus. Curr Top Microbiol Immunol. 2002;261:53-74.

Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial Engli.

Ng et al. Predicting the effects of amino acid substitutions on protein function. Annu Rev Genomics Hum Genet. 2006;7:61-80.

Nichols et al., Formation of Pluripotent Stem Cells in the Mammalian Embryo Depends on the POU Transcription Factor Oct4, Cell 95:379-91, 1998.

Nienhuis et al., Genotoxicity of Retroviral Integration in Hematopoietic Cells, Mol. Ther. 13(6):1031-49, 2006.

Niwa et al. Self-renewal of pluripotent embryonic stem cells is mediated via activation of STAT3. Genes Dev. Jul. 1, 1998;12(13):2048-60.

Niwa et al., Efficient Selection for High-Expression Transfectants With a Novel Eukaryotic Vector, Gene 108(2):193-99, 1991.

Nolta et al., Transduction of Pluripotent Human Hematopoietic Stem Cells Demonstrated by Clonal Analysis After Engraftment in Immune-Deficient Mice, Proc. Natl. Acad. Sci. USA 93(6):2414-19, 1996.

Office Action issued in connection with Chinese Patent Application No. 200680048227.7, Sep. 9, 2010.

Office Action issued in connection with European Patent Application No. EP 06834636.0, Apr. 30, 2010.

Office Action issued in connection with European Patent Application No. EP 06834636.0, Oct. 25, 2010.

Office Action issued in connection with Israeli Patent Application No. 191903, Aug. 19, 2010.

Office Action issued in connection with Japanese Patent Application No. JP 2009-056747, mailed Jun. 2, 2009.

Office Action issued in connection with Japanese Patent Application No. JP 2009-056748, mailed Jun. 2, 2009.

Office Action issued in connection with Japanese Patent Application No. JP 2009-056749, mailed Jun. 4, 2009.

Office Action issued in connection with Japanese Patent Application No. JP 2009-056750, mailed Jun. 2, 2009.

Office Action issued in connection with New Zealand Patent Application No. 569530, Apr. 20, 2010.

Office Action issued in connection with Singapore Patent Application No. 200804231-9, Apr. 13, 2010.

Office Action issued in connection with Singapore Patent Application No. 200901803-7, Jan. 22, 2010.

Official Action issued in connection with Eurasian Patent Application No. 200870046, Nov. 9, 2009.

Official Action issued in connection with Eurasian Patent Application No. 201000858, Jul. 14, 2010.

Official Action issued in connection with Japanese Patent Application No. JP 2009-056748, mailed Nov. 4, 2009.

Official Rejection issued in connection with Japanese Patent Application No. JP 2009-056748, mailed Feb. 23, 2010.

Official Rejection issued in connection with Japanese Patent Application No. JP 2009-056749, mailed Nov. 4, 2009.

Ohnuki et al., "Generation and characterization of human induced pluripotent stem cells." Curr Protoc Stem Cell Biol. Jun. 2009;Chapter 4:Unit 4A.2.

Okabe et al., Green Mice' as a Source of Ubiquitous Green Cells, FEBS Letters, 1997, vol. 407, pp. 313-319.

Okamoto et al., A Novel Octamer Binding Transportation Factor is Differentially Expressed in Mouse Embryonic Cells, Cell 60:461-72, 1990.

Okita et al. Generation of germline-competent induced pluripotent stem cells. Nature Jul. 19, 2007; 448(7151)313-17.

Okita et al. Intracellular Signaling Pathways Regulating Pluripotency of Embryonic Stem Cells. Current Stem Cell Research & Therapy. 2006;1:103-111.

Okita et al., "Generation of mouse-induced pluripotent stem cells with plasmid vectors." Nat Protoc. 2010;5(3):418-28.

Okita et al., "Induction of pluripotency by defined factors." Exp Cell Res. Oct. 1, 2010;316(16):256570. Epub Apr. 24, 2010.

Okita et al., Generation of Mouse Induced Pluripotent Stem Cells Without Viral Vectors, Science 322(5903):949-53, published online Oct. 9, 2008.

Okuda et al., UTF1, A Novel Transcriptional Coactivator Expressed in Pluripotent Embryonic Stem Cells and Extra-Embryonic Cells, EMBO J. 17(7):2019-32, 1998.

Okumura-Nakanishi et al., "Oct-3/4 and Sox2 Regulate Oct-3/4 Gene in Embryonic Stem Cells," The Journal of Biological Chemistry 280(7):5307-5317, Feb. 18, 2006.

Onishi et al. Applications of retrovirus-mediated expression cloning. Exp Hematol. Feb. 1996;24(2):324-9.

Osuna et al. Protein evolution by codon-based random deletions. Nucleic Acids Res. Sep. 30, 2004; 32(17):e136.

Padmanabhan et al. Visualization of telomerase reverse transcriptase (hTERT) promoter activity using a trimodality fusion reporter construct. J Nucl Med. Feb. 2006;47(2):270-7.

Park et al. Reprogramming of human somatic cells to pluripotency with defined factors. Nature. 2008;451(7175):141-146.

Parson, A.B. Stem Cell Biotech: Seeking a Piece of the Action. Cell. Feb. 22, 2008; 132(4):511-513.

Pearson et al. Improved tools for biological sequence comparison. Proc Natl Acad Sci USA. Apr. 1988;85(8):2444-8.

Pearson, W.R. Rapid and sensitive sequence comparison with FASTP and FASTA. Methods Enzymol. 1990;183:63-98.

Peister et al., Gene Ther, Jan. 2004, vol. 11, Issue 2, pp. 224-228.

Pera, M.F. On the Road to Reprogramming. Stem Cell Research. 2008; 1:103-104.

Postic et al., Dual Roles for Glucokinase in Glucose Homeostasis as Determined by Liver and Pancreatic β Cell-Specific Gene Knockouts Using Cre Recombinase, J. Biol. Chem 274(1):305-15, 1999.

Pralong et al. Cell fusion for reprogramming pluripotency: toward elimination of the pluripotent genome. Stem Cell Rev. 2006;2(4):331-40.

Qin et al., Direct Generation of ES-Like Cells From Unmodified Mouse Embryonic Fibroblasts by Oct4/Sox2/Myc/Klf4, Cell Res. 17(11):959-62, 2007.

Quenneville et al., Mol. Ther., Oct. 2004, vol. 10, Issue 4, pp. 679-687.

Rao, M. Conserved and divergent paths that regulate self-renewal in mouse and human embryonic stem cells. Dev Biol. Nov. 15, 2004;275(2):269-86.

Ratajczak et al. Bone-marrow-derived stem cells—our key to longevity? J. Appl. Genet. 2007;48(4): 307-319.

Riviére et al. Effects of retroviral vector design on expression of human adenosine deaminase in murine bone marrow transplant recipients engrafted with genetically modified cells. Proc Natl Acad Sci USA. Jul. 18, 1995;92(15):6733-7.

Rodda et al. Transcriptional regulation of nanog by OCT4 and SOX2. J Biol Chern. Jul. 1, 2005;280(26):24731-7.

Rodriguez et al. Manipulation of OCT4 levels in human embryonic stem cells results in induction of differential cell types. Exp Biol Med (Maywood). Nov. 2007;232(10):1368-80.

Root et al. Genome-scale loss-of-function screening with a lentiviral RNAi library. Nat Methods. Sep. 2006;3(9):715-9.

Rosenfeld et al. Adenovirus-mediated transfer of a recombinant alpha 1-antitrypsin gene to the lung epithelium in vivo. Science. Apr. 19, 1991;252(5004):431-4.

Rossant, J. Stem Cell and Early Lineage Development. Cell. Feb. 22, 2008; 132(4):527-531.

Rossant, J. Stem Cells: The Magic Brew. Nature. Jul. 19, 2007;448, 260-262.

Rossi et al. Stem Cells and the Pathways to Aging and Cancer. Cell. Feb. 22, 2008; 132(4):681-696.

Ryan et al., POU Domain Family Values: Flexibility, Partnerships, and Developmental Codes, Genes Dev. 11:1207-25, 1997.

Sadowski et al. GAL4-VP16 is an unusually potent transcriptional activator. Nature. Oct. 6, 1988;335(6190):563-;4.

Sakai et al., A Transgenic Mouse Line That Retains Cre Recombinase Activity in Mature Oocytes Irrespective of the cre Transgene Transmission, Biochem. Biophys. Res. Commun. 237(2):318-24, 1997.

Saldanha et al. Assessment of telomere length and factors that contribute to its stability. Eur J Biochem. Feb. 2003;270(3):389-403.

Salmon et al., Reversible Immortalization of Human Primary Cells by Lentivector-Mediated Transfer of Specific Genes, Mol. Ther. 2(4):404-14, 2000.

Sato et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.

Schepers et al., Twenty Pairs of Sox: Extent, Homology, and Nomenclature of the Mouse and Human Sox Transcription Factor Gene Families, Dev. Cell 3:167-70, 2002.

Scherr et al. Gene silencing by small regulatory RNAs in mammalian cells. Cell Cycle. Feb. 1, 2007;6(4):444-9.

Shao et al., Generation of iPS Cells Using Defined Factors Linked Via the Self-Cleaving 2A Sequences in a Single Open Reading Frame, Cell Res., Mar. 2009, vol. 19, Issue 3, pp. 296-312.

Shi et al., A Combined Chemical and Genetic Approach for the Generation of Induced Pluripotent Stem Cells, Cell Stem Cell 2:525-28, 2008.

Shi et al., of Pluripotent Stem Cells From Mouse Embryonic Fibroblasts by Oct4 and Klf4 With Small-Molecule Compounds, Cell Stem Cell 3:568-74, 2008.

Silva et al. Capturing Pluripotericy. Cell. Feb. 22, 2008; 132(4):532-536.

Silva et al. Profiling essential genes in human mammary cells by multiplex RNAi screening. Science. Feb. 1, 2008;319(5863):617-20.

Silva et al., Promotion of Reprogramming to ground State Pluripotency by Signal Inhibition, PLoS Biology 6910):2237-47, 2008.

Sinkkonen et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.

Skottman et al. Culture conditions for human embryonic stem cells. Reproduction. Nov. 2006;132(5):691-8.

Soldner et al., Parkinson's Disease Patient-Derived Induced Pluripotent Stem Cells Free of Viral Reprogramming Factors, Cell, Mar. 6, 2009, vol. 136, Issue 5, pp. 964-977.

Spencer et al., E-Cadherin Inhibits Cell Surface Localization of the Pro-Migratory 5T4 Oncofetal i Antigen in Mouse Embryonic Stem Cells, Mol. Biol. Cell 18:2838-51, 2007.

Spivakov et al., Epigenetic Signatures of Stem-Cell Identify, Nat. Rev. Genet. 8(4):263-271, 2007.

Stadler et al. Small RNAs: Keeping Stem Cells in Line. Cell. Feb. 22, 2008; 132(4):563-566.

Stadtfeld et al., Induced Pluripotent Stem Cells Generated Without Viral Integration, Science 322(5903):945-49, published online Sep. 25, 2008.

Stadtfeld, M. Defining molecular cornerstones during fibroblast to iPS cell reprogramming in mouse. Cell Stem Cell. Mar. 6, 2008;2(3):230-40.

Stem Cells Made to Mimic Disease, BBC News, http://newsvote.bbc.co.uk/mpapps/pagetools/print/news.bbc.co.uk/2/hi/health/7334365.stm, Apr. 7, 2008.

Stewart et al. Mechanisms of self-renewal in human embryonic stem cells. Eur J Cancer. Jun. 2006;42(9):1257-72.

Stojkovic et al. Derivation, growth and applications of human embryonic stem cells. Reproduction. Sep. 2004;128(3):259-67.

Strelchenko et al. Embryonic stem cells from morula. Methods Enzymol. 2006;418:93-108.

Suh et al., Human Embryonic Stem Cells Express a Unique Set of microRNAs, Developmental Biology 270:488-498, 2004.

Sumi et al. Apoptosis and differentiation of human embryonic stem cells induced by sustained activation of c-Myc. Oncogene. Aug. 16, 2007;26(38):5564-76.

Surani et al., A New Route to Rejuvenation, nature 443:284-285, Sep. 21, 2006.

Tada et al., Nuclear Reprogramming of Somatic Cells by in vitro Hybridization With ES Cells, Current Biology 11(19):1553-58, 2001.

Takahashi et al. Induction of pluripotent stem cells from adult human fibroblasts by defined factors. Cell. Nov. 30, 2007;131(5):861-72.

Takahashi et al. Induction of pluripotent stem cells from fibroblast cultures. Nat Protoc. 2007;2(12):3081-9.

Takahashi et al. Induction of pluripotent stem cells from mouse embryonic and adult fibroblasts by defined factors. Cell. Aug. 25, 2006; 126(4):663-676.

Takahashi et al., Induced Pluripotent Stem Cells, Jikken Igaku (Experimental Medicine) 26(5):35-40, 2008.

Takahashi et al., Role of ERas in Promoting Tumour-Like Properties in Mouse Embryonic Stem Cells, Nature 423:541-45, 2003.

Takahashi, K. et al. "Human induced pluripotent stem cells on autologous feeders." PLoS One. Dec. 2, 2009;4(12):e8067.

Takeda et al., Characterization of Dental Pulp Stem Cells of Human Tooth Germs, Journal of Dental Research, 2008, vol. 87, pp. 676-681.

Takeda et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.

Tan et al. Changing viral tropism using immunoliposomes alters the stability of gene expression: implications for viral vector design. Mol Med. Mar.-Apr. 2007; 13(3-4):216-26.

Tantin et al. High-throughput biochemical analysis of in vivo location data reveals novel distinct classes of POU5FI(Oct4)/DNA complexes. Genome Res. Apr. 2008;18(4):631-9.

Taranger et al., Induction of Dedifferentiation, Genomewide Transcriptional Programming, and Epigenetic reprogramming by Extracts of Carcinoma and Embryonic Stem Cells, Mol. Biol. Cell. 16:5719-35, 2005.

Tateno et al., Heterogeneity of Growth Potential of Adult Rat Hepatocytes in vitro, Hepatology 31(1):65-74, 2000.

Thomson et al. Embryonic Stem Cell Lines Derived from Human Blastocysts. Science. Nov. 1998;282(5391):1145.

Time. The Top 10 Everything of 2008—1. First Neurons Created from ALS Patients. Available at http://www.time.com/time/specials/2008/top10/article/0,30583,1855948_1863993,00. html. Accessed Dec. 15, 2008.

Tokuzawa et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.

Tokuzawa et al., Fbx15 is a Novel Target of Oct3/4 but is Dispensible for Embryonic Stem Cell Self-Renewal and Mouse Development, Mol. Cell Biol. 23(8):2699-718, 2003.

Trompeter, et. al. Rapid and highly efficient gene transfer into natural killer cells by nucleofection. J Immunol Methods. Mar. 1, 2003;274(1-2):245-56.

Troyanskaya et al. Nonparametric methods for identifying differentially expressed genes in microarray data. Bioinformatics. 2002;18(11): 1454-1461.

Tsubooka et al. "Roles of Sall4 in the generation of pluripotent stem cells from blastocysts and fibroblasts." Genes Cells, Jun. 2009;14(6):683-94.

Tsunoda, Y., et al., The Recent Progress on Nuclear Transfer in Mammals, Zoological Science 17:1177-1184, 2000.

Tzukerman et al. Identification of a novel transcription factor binding element involved in the regulation by differentiation of the human telomerase (hTERT) promoter. Mol Biol Cell. Dec. 2000;11(12):4381-91.

Vermeesch et al. Guidelines for molecular karyotyping in constitutional genetic diagnosis. Eur J Hum Genet. Nov. 2007;15(11):1105-14.

Verrey et al., CATs and HATs: The SLC7 Family of Amino Acid Transporters, Pflugers Archive—European Journal of Physiology, DOI 10.1007/s00424-003-1086-Z, pp. 1-23, published online Jun. 11, 2003.

Vintersten et al., Mouse in Red: Red Fluorescent Protein Expression in Mouse ES Cells, Embryos, and Adult Animals, Genesis 40:41-46, 2004.
Viswanathan et al., Selective Blockade of MicroRNA Processing by Lin28, Science 320:97-100, 2008.
Wadia et al., Protein Transduction Technology, Curr. Opin. Biotechnol. 13:52-56, 2002.
Wakao et al., "Multilineage-Differentiating Stress-Enduring (Muse) Cells Are a Primary Source of Induced Pluripotent Stem Cells in Human Fibroblasts," PNAS Early Edition, pp. 1-6, May 31, 2011, available at www.pnas.org/cgi/content/short/1100816108.
Wakayama et al., Differentiation of Embryonic Stem Cell Lines Generated From Adult Somatic Cells by Nuclear Transfer, Science 292:740-43, 2001.
Wakayama et al., Full-Term Development of Mice From Enucleated Oocytes Injected With Cumulus Cell Nuclei, Nature 394:369-74, 1998.
Wang et al., A Protein Interaction Network for Pluripotency of Embryonic Stem Cells, Nature 444:364-68, 2006.
Watson et al. Identifying Genes Regulated in a Myc-dependent Manner. J Biol Chem. Oct. 4, 2002;277(40):36921-30.
Wernig et al. c-Myc is dispensable for direct reprogramming of mouse fibroblast. Cell Stem Cell. 2008; 2, 10-12.
Wernig et al. In vitro reprogramming of fibroblasts into a pluripotent ES-cell-like state. Nature. Jul. 19, 2007;448:318-324.
Wernig et al., Neurons Derived From Reprogrammed Fibroblasts Functionally Integrate Into the Fetal Brain and Improve Symptoms of Rats With Parkinson's Disease, Proc. Natl. Acad. Sci. U.S.A. 105(15):5856-5861, 2008.
Wilmut et al., Viable Offspring Derived From Fetal and Adult Mammalian Cells, Nature 385:810-13, 1997.
Woltjen et al., PiggyBac Transposition Reprograms Fibroblasts to Induced Pluripotent Stem Cells, Nature, Mar. 1, 2009, vol. 458, Issue 7239, pp. 766-770.
Wu et al., Sall4 Interacts With Nanog and Co-Occupies Nanog Genomic Sites in Embryonic Stem Cells, J. Biol., Chem., 281(34):24090-24094, 2000.
Xu et al. BMP4 initiates human embryonic stem cell differentiation to trophoblast. Nat Biotechnol. Dec. 2002;20(12):1261-4.
Xu et al. Random mutagenesis libraries: optimization and simplification by PCR. Biotechniques. Dec. 1999;27(6):1102, 1104, 1106, 1108.
Xu et al., Basic FGF and Suppression of BMP Signaling Sustain Undifferentiated Proliferation of Human ES Cells, Nat. Methods 2(3):185-90, 2005.
Yamanaka et al., "Nuclear reprogramming to a pluripotent state by three approaches." Nature. Jun. 10, 2010;465(7299):704-12.
Yamanaka et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.
Yamanaka S., "An interview with . . . Shinya Yamanaka. Interview by Mary Muers." Nat Rev Genet. Jun. 2010;11(6):390.
Yamanaka S., "Patient-specific pluripotent stem cells become even more accessible" Cell Stem Cell. Jul. 2, 2010;7(1):1-2.
Yamanaka S., "Pluripotency and nuclear reprogramming." Philos Trans R Soc Lond B Biol Sci. Jun. 27, 2008;363(1500):2079-87.
Yamanaka S., "Symposium: Nuclear reprogramming and the control of differentiation in mammalian embryos. Introduction." Reprod Biomed Online. Jan. 2008;16(1):11-2.
Yamanaka, Pluripotency of Differentiation and miRNA, The Journal of Biochemistry, vol. 79, No. 11, Abstract 3BT17 From the 80th Annual Meeting of the Japanese Biochemical Society, Nov. 25, 2007, along with an English language translation thereof.
Yamanaka, S. Induction of Pluripotent stem cells from mouse fibroblasts by four transcription factors. Cell Prolif. 2008;41 (Suppl. 1): 51-56.
Yamanaka, S., "A fresh look at iPS cells." Cell. Apr. 3, 2009;137(1):13-7.
Yamanaka, S., "Ekiden to iPS Cells." Nat Med. Oct. 2009;15(10):1145-8.
Yamanaka, S., "Elite and stochastic models for induced pluripotent stem cell generation." Nature. Jul. 2, 2009;460(7251):49-52.
Yamanaka, S., "Induction of Pluripotency by Defined Factors—The History of iPS Cells", Gairdner Award acceptance speech, presented on or about Oct. 29, 2009.
Yamanaka, S., "Induction of Pluripotency by Defined Factors", lecture presented on or about Oct. 29, 2009.
Yang et al., Nuclear Reprogramming of Cloned Embryos and Its Implications for Therapeutic Cloning, Nat. Genet. 39(3):295-302, 2007.
Yee et al. Generation of high-titer pseudotyped retroviral vectors with very broad host range. Methods Cell Biol. 1994;43 Pt A:99-112.
Ying et al., BMP Induction of ID Proteins Suppresses Differentiation and Sustains Embryonic Stem Cell Self-Renewal in Collaboration With STAT3, Cell 115:281-92, 2003.
Ying et al., The MicroRNA: Overview of the RNA Gene That Modulates Gene Functions, Methods in Molecular Biology, MicroRNA Protocols, vol. 342, pp. 1-18, Humana Press, 2006.
Yoshida et al. "Hypoxia enhances the generation of induced pluripotent stem cells." Cell Stem Cell. Sep. 4, 2009;5(3):237-41. Epub Aug. 27, 2009.
Yoshida et al., "Recent stem cell advances: induced pluripotent stem cells for disease modeling and stem cell-based regeneration." Circulation. Jul. 6, 2010;122(1):80-7.
Yu et al. Induced pluripotent stem cell lines derived from human somatic cells. Science. Dec. 21, 2007;318(5858):1917-20.
Yu et al., Human Induced Pluripotent Stem Cells Free of Vector and Transgene Sequences, Science 324:797-801, 2009.
Zhan et al. Conservation and variation of gene regulation in embryonic stem cells assessed by comparative genomics. Cell Biochem Biophys. 2005;43(3):379-405.
Zhang et al., MicroRNA: A New Player in Stem Cells, Journal of Cellular Physiology 209:266-269, 2006.
Zhao et al., "Two Supporting Factors Greatly Improve the Efficiency of Human iPSC Generation" Cell Stem Cell 3:475-79, 2008.
Zhou et al., Generation of Induced Pluripotent Stem Cells Using Recombinant Proteins, Cell Stem Cell 4:381-384, 2009.
Ziegler et al., The Cationic Cell-Penetrating Peptide $CPP^{TAT}$ Derived From the HIV-1 Protein TAT is Rapidly Transported into Living Fibroblasts: Optical, Biophysical, and Metabolic Evidence, Biochemistry 44:138-148, published online Dec. 14, 2004.
Bongso, A., et al., Isolation and Culture of Inner Cell Mass Cells From Human Blastocysts, Human Reproduction 9(11):2110-2117, 1994.
Extended European Search Report mailed by the European Patent Office on Feb. 21, 2012 in corresponding European application No. 0976377.2 in 6 pages.
Ebert et al., "Induced Pluripotent Stem Cells from a Spinal Muscular Atrophy Patient", Nature, vol. 457, No. 7227, Jan. 15, 2009, pp. 277-280.
U.S. Appl. No. 12/663,840, filed Dec. 9, 2009, Sakurada et al.
Adewumi, et al. Characterization of human embryonic stem cell lines by the International Stem Cell Initiative. Nat Biotechnol. 2007; 25, 803-816.
Altschul, et al. Gapped BLAST and PSI-BLAST: a new generation of protein database search programs. Nucleic Acids Research. 1997;25(17): 3389-3402.
Amit, et al. Clonally derived human embryonic stem cell lines maintain pluripotency and proliferative potential for prolonged periods of culture. Dev Biol. Nov. 15, 2000;227(2):271-8.
Anderson, et al. Transgenic enrichment of cardiomyocytes from human embryonic stem cells. Mol Ther. Nov. 2007;15(11):2027-36.
Aoi, et al. Generation of Pluripotent Stem Cells from Adult Mouse Liver and Stomach Cells. Science. Published Online Feb. 14, 2008. Science DOI: 10.1126/science.1154884.
Assady, et al. Insulin production by human embryonic stem cells. Diabetes. Aug. 2001;50(8):1691-7.
Bader, et al. Leukemia inhibitory factor modulates cardiogenesis in embryoid bodies in opposite fashions. Circ Res. Apr. 14, 2000;86(7):787-94.
Bendall, et al. IGF and FGF cooperatively establish the regulatory stem cell niche of pluripotent human cells in vitro. Nature. Aug. 30, 2007;448(7157):1015-21.
Blelloch, et al. Generation of Induced Pluripotent Stem Cells in the Absence of Drug Selection. Cell Stem Cell. 2007; 1, 245-247.

Blow, N. Stem cells: in search of common ground. Nature. Feb. 14, 2008;451(7180):855-8.

Bonetta, L. European Stem Cell Patents: Taking the moral High Road? Cell. Feb. 22, 2008; 132(4):514-516.

Brena, et al. Quantitative assessment of DNA methylation: Potential applications for disease diagnosis, classification, and prognosis in clinical setting. J Mol Med. May 2006;84(5):365-77.

Brüstle, et al. Embryonic stem cell-derived glial precursors: a source of myelinating transplants. Science. Jul. 30, 1999;285(5428):754-6.

Burns, et al. Diabetes mellitus: a potential target for stem cell therapy. Curr Stem Cell Res Ther. May 2006;1(2):255-66.

Buttery, et al. Differentiation of osteoblasts and in vitro bone formation from murine embryonic stem cells. Tissue Eng. Feb. 2001;7(1):89-99.

Cai, et al. Directed differentiation of human embryonic stem cells into functional hepatic cells. Hepatology. May 2007;45(5):1229-39.

Chadwick, et al. Cytokines and BMP-4 promote hematopoietic differentiation of human embryonic stem cells. Blood. Aug. 1, 2003;102(3):906-15.

Chen, et al. From stem cells to oligodendrocytes: prospects for brain therapy. Stem Cell Rev. Dec. 2007;3(4):280-8.

Childs, et al. Regression of metastatic renal-cell carcinoma after nonmyeloablative allogeneic peripheral-blood stem-cell transplantation. N Engl J Med. Sep. 14, 2000;343(11):750-8.

Chin, et al. Induced pluripotent stem cells and embryonic stem cells are distinguished by gene expression signatures. Cell Stem Cell. Jul. 2, 2009;5(1):111-23.

Cinalli, et al. Germ Cells are Forever. Cell. Feb. 22, 2008; 132(4):559-562.

CIRM Public Release. $24 Million in New Stem Cell Research Funding Awarded to 25 California Institutions. California Institute for Regenerative Medicine (4 pages). Jun. 27, 2008.

CIRM: Summaries of Review for Applications to RFA 07-05. California Institute for Regenerative Medicine Web site. 2007. Available at: http://www.cirm.ca.gov/RFA/rfa_07-05/. Accessed Jul. 1, 2008.

Coutts, et al. Stem cells for the treatment of spinal cord injury. Exp Neurol. Feb. 2008;209(2):368-77.

Current claims for U.S. Appl. No. 10/861,040, Mar. 16, 2007.

Cyranoski, D. Stem cells: 5 things to know before jumping on the iPS bandwagon. Nature. 2008;452(7186)406-408.

D'Amour, et al. Efficient differentiation of human embryonic stem cells to definitive endoderm. Nat Biotechnol. Dec. 2005;23(12):1534-41.

D'Amour, et al. Production of pancreatic hormone-expressing endocrine cells from human embryonic stem cells. Nat Biotechnol. Nov. 2006;24(11):1392-401.

Daley, et al. Prospects for Stem Cell Based Therapy. Cell. Feb. 22, 2008; 132(4):544-548.

Dani, et al. Differentiation of embryonic stem cells into adipocytes in vitro. J Cell Sci. Jun. 1997;110 ( Pt 11):1279-85.

Denker, H. W. Human embryonic stem cells: the real challenge for research as well as for bioethics is still ahead of us. Cells Tissues Organs. 2008;187(4):250-6.

D'Ippolito, et al. Marrow-isolated adult multilineage inducible (MIAMI) cells, a unique population of postnatal young and old human cells with extensive expansion and differentiation potential. J Cell Sci. Jun. 15, 2004;117(Pt 14):2971-81.

Durcova-Hills, et al. Induced reprogramming of human somatic cells into pluripotency: a new way how to generate pluripotent stem cells. Differentiation. Apr. 2008;76(4):323-5.

Ebert, L. Yamanaka scooped on iPS (stem cell) patent?!. TMCNews reports on Jan. 4, 2009. Available at http://ipbiz.blogspot.com/2009/01/yamanaka-scooped-on-ips-stem-cell.html. Accessed May 19, 2009.

Elefanty, A. Ed. In this Issue . . . Stem Cell Research. 2008; 1:87.

Felgner, et al. Lipofection: a highly efficient, lipid-mediated DNA-transfection procedure. Proc Natl Acad Sci U S A. Nov. 1987;84(21):7413-7.

Hanna, et al. Direct Reprogramming of Terminally Differentiated Mature B Lymphocytes to Pluripotency. Cell. Apr. 18, 2008;133: 250-264. Erratum in: Cell. 2008; 134(2):365.

Hermann, et al. Efficient generation of neural stem cell-like cells from adult human bone marrow stromal cells. J Cell Sci. Sep. 1, 2004;117(Pt 19):4411-22.

Hyun, et al. New advances in iPS cell research do not obviate the need for human embryonic stem cells. Cell Stem Cell. Oct. 11, 2007;1(4):367-8.

Itsykson, et al. Derivation of neural precursors from human embryonic stem cells in the presence of noggin. Mol Cell Neurosci. Sep. 2005;30(1):24-36.

Janssens, et al. Autologous bone marrow-derived stem-cell transfer in patients with ST-segment elevation myocardial infarction: double-blind, randomised controlled trial. Lancet. Jan. 14, 2006;367(9505):113-21.

Jiang, et al. In vitro derivation of functional insulin-producing cells from human embryonic stem cells. Cell Res. Apr. 2007;17(4):333-44.

Kawasaki, et al. Induction of midbrain dopaminergic neurons from ES cells by stromal cell-derived inducing activity. Neuron. Oct. 2000;28(1):31-40.

Kehat, et al. Human embryonic stem cells can differentiate into myocytes with structural and functional properties of cardiomyocytes. J Clin Invest. Aug. 2001;108(3):407-14.

Kitamura, et al. Retrovirus-mediated gene transfer and expression cloning: powerful tools in functional genomics. Exp Hematol. Nov. 2003;31(11):1007-14.

Kitamura, T. New experimental approaches in retrovirus-mediated expression screening. Int J Hematol. Jun. 1998;67(4):351-9.

Kramer, et al. Embryonic stem cell-derived chondrogenic differentiation in vitro: activation by BMP-2 and BMP-4. Mech Dev. Apr. 2000;92(2):193-205.

Krausz, E. High-content siRNA screening. Mol Biosyst. Apr. 2007;3(4):232-40.

Kunath, et al. FGF stimulation of the Erk1/2 signalling cascade triggers transition of pluripotent embryonic stem cells from self-renewal to lineage commitment. Development. Aug. 2007;134(16):2895-902.

Lee, et al. Efficient generation of midbrain and hindbrain neurons from mouse embryonic stem cells. Nat Biotechnol. Jun. 2000;18(6):675-9.

Lieschke, et al. Development of functional macrophages from embryonal stem cells in vitro. Exp Hematol. Apr. 1995;23(4):328-34.

Lowry, et al. Generation of human induced pluripotent stem cells from dermal fibroblasts. Proc Natl Acad Sci U S A. Feb. 26, 2008;105(8):2883-8.

Lumelsky, et al. Differentiation of embryonic stem cells to insulin-secreting structures similar to pancreatic islets. Science. May 18, 2001;292(5520):1389-94.

Mali, et al. Improved efficiency and pace of generating induced pluripotent stem cells from human adult and fetal fibroblasts. Stem Cells. Aug. 2008;26(8):1998-2005.

Marchetto, et al. Transcriptional signature and memory retention of human-induced pluripotent stem cells. PLoS One. Sep. 18, 2009;4(9):e7076.

Morizane, et al. From bench to bed: the potential of stem cells for the treatment of Parkinson's disease. Cell Tissue Res. Jan. 2008;331(1):323-36.

Mummery, et al. Differentiation of human embryonic stem cells to cardiomyocytes: role of coculture with visceral endoderm-like cells. Circulation. Jun. 3, 2003;107(21):2733-40.

Murry, et al. Differentiation of Embryonic Stem Cells to Clinically Relevant Populations: Lessons from Embryonic Development. Cell. Feb. 22, 2008; 132(4):661-680.

Orkin, et al. Hematopoiesis: An Evolving Paradigm for Stem Cell Biology. Cell. Feb. 22, 2008; 132(4):631-644.

Park, A. Stem-cell research: The quest resumes.Time Magazine. Feb. 9, 2009. Available at http://www.time.com/time/health/article/0,8599,1874717,00.html. Accessed Jun. 3, 2009.

Pomp, et al. Generation of peripheral sensory and sympathetic neurons and neural crest cells from human embryonic stem cells. Stem Cells. Aug. 2005;23(7):923-30.

Prelle, et al. Overexpression of insulin-like growth factor-II in mouse embryonic stem cells promotes myogenic differentiation. Biochem Biophys Res Commun. Nov. 2, 2000;277(3):631-8.

Rambhatla, et al. Generation of hepatocyte-like cells from human embryonic stem cells. Cell Transplant. 2003;12(1):1-11.

Reubinoff, et al. Neural progenitors from human embryonic stem cells. Nat Biotechnol. Dec. 2001;19(12):1134-40.

Rubin, L. Stem Cell and Drug Discovery: The Beginning of a New Era? Cell. Feb. 22, 2008; 132(4):549-552.

Schuldiner, et al. Induced neuronal differentiation of human embryonic stem cells. Brain Res. Sep. 21, 2001;913(2):201-5.

Schwenk, et al. Hybrid embryonic stem cell-derived tetraploid mice show apparently normal morphological, physiological, and neurological characteristics. Mol Cell Biol. Jun. 2003;23(11):3982-9.

Science magazine names top 10 breakthroughs of 2008. Available at http://arstechnica.com/old/content/2008/12/isciencei-names-top-10-scientific-breakthroughs-of-2008.ars. Accessed May 19, 2009.

Shah, R. Pharmacogenetics in drug regulation: promise, potential and pitfalls. Philos Trans R Soc Lond B Biol Sci. Aug. 29, 2005; 360(1460): 1617-1638.

Sottile, et al. In vitro osteogenic differentiation of human ES cells. Cloning Stem Cells. 2003;5(2):149-55.

The Japan Times. Bayer team makes stem cells from skin. Apr. 12, 2008. Available at http://search.japantimes.co.jp/cgi-bin/nn20080412a5.html. Accessed May 19, 2009.

Time. The Top 10 Everything of 2008-1. First Neurons Created from ALS Patients. Available at http://www.time.com/time/specials/2008/top10/article/0,30583,1855948_1863993,00.html. Accessed Dec. 15, 2008.

Tsai, et al. In vivo immunological function of mast cells derived from embryonic stem cells: an approach for the rapid analysis of even embryonic lethal mutations in adult mice in vivo. Proc Nati Acad Sci U S A. Aug 1, 2000;97(16):9186-90.

Ulloa-Montoya, et al. Comparative transcriptome analysis of embryonic and adult stem cells with extended and limited differentiation capacity. Genome Biol. 2007;8(8):R163.

Valuer, et al. Activin/Nodal and FGF pathways cooperate to maintain pluripotency of human embryonic stem cells. J Cell Sci. Oct. 1, 2005;118(Pt 19):4495-509.

Vogel, G. Breakthrough of the year. Reprogramming Cells. Science. Dec. 19, 2008;322(5909):1766-7.

Wagner, et al. Mesenchymal stem cell preparations—comparing apples and oranges. Stem Cell Rev. Dec. 2007;3(4):239-48.

Wang, et al. Inhibition of caspase-mediated anoikis is critical for bFGF-sustained culture of human pluripotent stem cells. J Biol Chem. Oct 16, 2009. [Epub ahead of print].

Watanabe, et al. A ROCK inhibitor permits survival of dissociated human embryonic stem cells. Nat Biotechnol. 2007; 25, 681-686.

Werbowetski-Ogilvie, et al. Characterization of human embryonic stem cells with features of neoplastic progression. Nat Biotechnol. Jan. 2009;27(1):91-7.

Wernig, et al. Neurons derived from reprogrammed fibroblasts functionally integrate into the fetal brain and improve symptoms of rats with Parkinson's disease. Proc Natl Acad Sci U S A. Apr. 15, 2008;105(15):5856-61.

What are adult stem Cells? Stem Cell Information. The National Institutes of Health resource for stem cell research. 2007. Available at: http://stemcells.nih.gov/info/basics/basics4.asp. Accessed Jun. 4, 2007.

Wu, et al. Origins and Fates of Cardiovascular Progenitor Cells. Cell. Feb. 22, 2008; 132(4):537-543.

Yamanaka, S. Strategies and new developments in the generation of patient-specific pluripotent stem cells. Cell Stem Cell. Jun. 7, 2007;1(1):39-49.

Yamane, et al. Derivation of melanocytes from embryonic stem cells in culture. Dev. Dyn. 1999;216: 450-458.

Yamashita, et al. Flk1-positive cells derived from embryonic stem cells serve as vascular progenitors. Nature. Nov. 2, 2000;408(6808):92-6.

Yuasa, et al. Transient inhibition of BMP signaling by Noggin induces cardiomyocyte differentiation of mouse embryonic stem cells. Nat Biotechnol. May 2005;23(5):607-11.

Zhang, et al. In vitro differentiation of transplantable neural precursors from human embryonic stem cells. Nat Biotechnol. Dec. 2001;19(12):1129-33.

Zhao, et al. Mechanisms and Functional Implications of Adult Neurogenesis. Cell. Feb. 22, 2008; 132(4):645-660.

Allegrucci, et al. Differences between human embryonic stem cell lines. Hum Reprod Update. Mar.-Apr. 2007;13(2):103-20.

Dimos, et al. Induced pluripotent stem cells generated from patients with ALS can be differentiated into motor neurons. Science. Aug. 29, 2008;321(5893):1218-21.

Hockemeyer, et al. A drug-inducible system for direct reprogramming of human somatic cells to pluripotency. Cell Stem Cell. Sep. 11, 2008;3(3):346-53.

Maherali, et al. A high-efficiency system for the generation and study of human induced pluripotent stem cells. Cell Stem Cell. Sep. 11, 2008;3(3):340-5.

Park, et al. Disease-specific induced pluripotent stem cells. Cell. Sep. 5, 2008;134(5):877-86.

Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.

International Search Report and Written Opinion issued in PCT/JP2011/051685, 2011.

Nakagawa, M., et al., Promotion of Direct Reprogramming by Transformation-Deficient Myc., Proc. Natl. Acad. Sci. USA 107(32):14152-14157, Aug. 2010.

Sarid, J., et al., Evolutionarily Conserved Regions of the Human c-Myc Protein Can Be Uncoupled From Transforming Activity, Proc. Natl. Acad. Sci. USA 84(1):170-173, 1987.

* cited by examiner

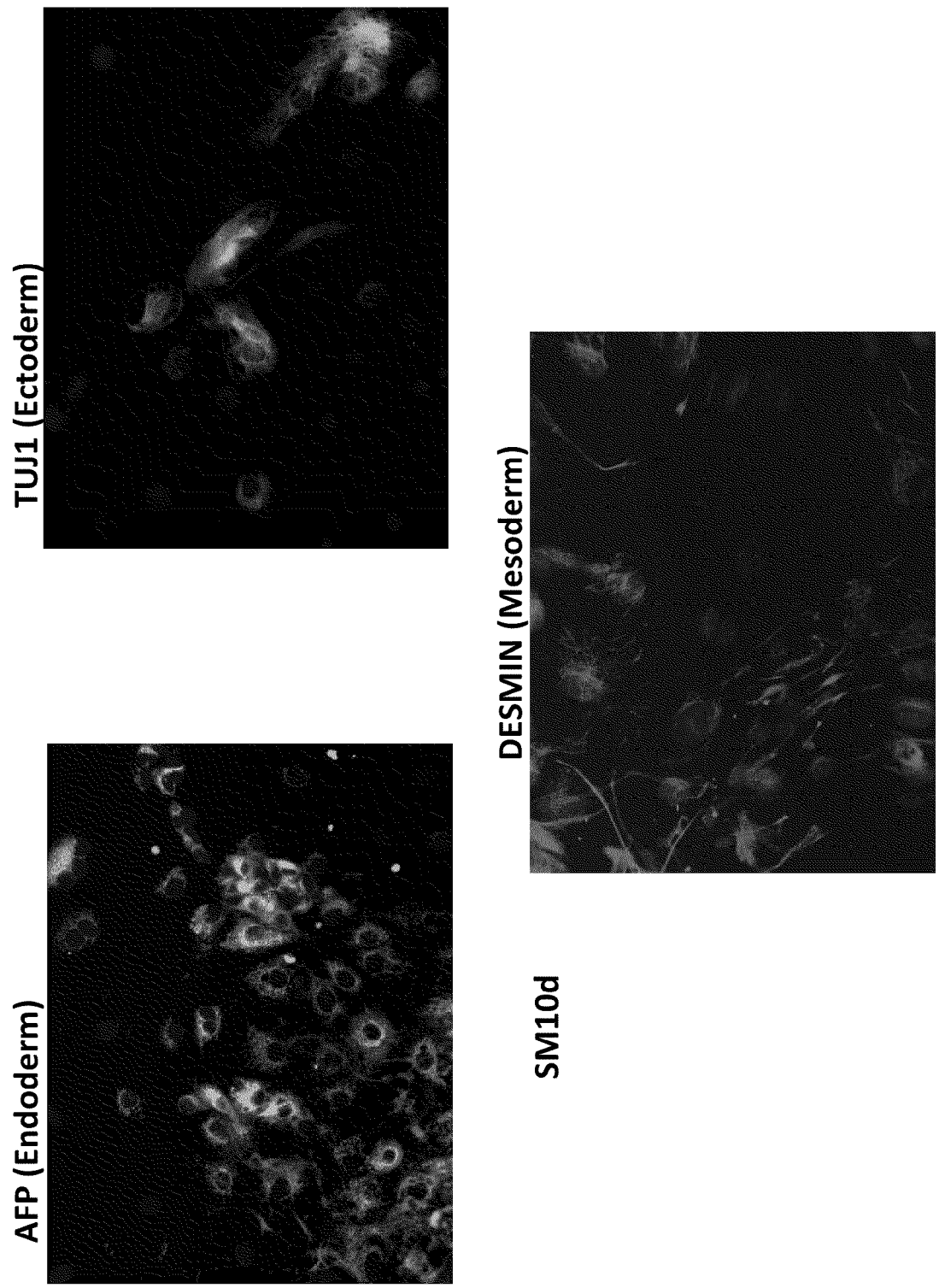

METHODS AND PLATFORMS FOR DRUG DISCOVERY USING INDUCED PLURIPOTENT STEM CELLS

CROSS-REFERENCE

This application is a continuation-in-part of U.S. application Ser. No. 12/157,967, filed Jun. 13, 2008, which claims the benefit of U.S. Provisional Application No. 61/040,646, filed Mar. 28, 2008, and which also claims the benefit of International Application No. PCT/EP2007/010019, filed Nov. 20, 2007, and which also claims the benefit of Japanese Application No. JPO-2007-159382, filed Jun. 15, 2007; this application also claims the benefit of International Application No. PCT/IB2008/002540, filed Jun. 13, 2008, International Application No. PCT/EP2008/005047, filed Jun. 13, 2008, U.S. Provisional Application No. 61/061,592, filed Jun. 13, 2008, and U.S. Provisional Application No. 61/061,594, filed Jun. 13, 2008, all of which are herein incorporated by reference in their entirety.

BACKGROUND OF THE INVENTION

The pharmaceutical industry has expended vast technical and financial resources to develop novel therapeutic agents. Yet, the failure rate (more than 90%) for lead compounds remains persistently high. Often, lead drug compounds that meet expectations in preclinical models, such as inbred animal models, or a small number of cell lines, are toxic or ineffective when administered to a human clinical trial patient population. A fundamental deficiency in most current drug development efforts is that they do not evaluate candidate drug efficacy and toxicity in the context of the extreme genetic diversity of the human patient population. In other words, in the present drug development paradigm, drug efficacy and toxicity are not tested on many, if not most, of the relevant genotype/phenotype combinations present in the human population. Indeed, even after successful trials in a relatively small human clinical trial population, unexpected adverse effects can be revealed once these drugs are administered to a broader human patient population.

SUMMARY OF THE INVENTION

The present invention involves methods for identifying an agent that corrects a phenotype associated with a health condition or a predisposition for a health condition comprising contacting a first population of cells from a human induced pluripotent stem cell line, or cells differentiated from the human induced pluripotent stem cell line, with a candidate agent; contacting a second population of cells from a human induced pluripotent stem cell line, or cells differentiated from the human induced pluripotent stem cell line, with a control agent; wherein the cells in both populations comprise at least one endogenous allele associated with the health condition or predisposition for the health condition; assaying the two populations and identifying candidate agents as correcting the phenotype if the first population is closer to a normal phenotype following treatment than the second population. The condition may be selected from health conditions such as a neurodegenerative disorder, a neurological disorder, a mood disorder, a cardiovascular disease, a metabolic disorder, a respiratory disease, a drug sensitivity condition, an eye disease, an immunological disorder, or a hematological disease. The cells may be differentiated from induced stem cells to neural stem cells, neurons, cardiomyocytes, hepatic stem cells, or hepatocytes. The phenotype described may be apoptosis, intracellular calcium level, calcium flux, protein kinase activity, enzyme activity, cell morphology, receptor activation, protein trafficking, intracellular protein aggregation, organellar composition, motility, intercellular communication, protein expression, or gene expression.

The invention also involves methods for identifying a diagnostic cellular phenotype comprising comparing a set of cells from a subject to cells from a subject free of the health condition wherein both sets of cells were induced pluripotent stem cells, or were cells differentiated from induced pluripotent stem cells, and wherein the comparison is performed on a computer. The cells may be differentiated from induced stem cells to neural stem cells, neurons, cardiomyocytes, hepatic stem cells, or hepatocytes.

The invention also involves methods for determining the risk of a health condition in a subject comprising comparing at least one phenotype determined in a first set of cells derived from the subject to the at least one phenotype determined in a second set of cells derived from subjects free of the health condition and to the at least one phenotype determined in a third set of cells derived from subjects suffering from the health condition; and indicating that the subject is at high risk for the health condition if the at least one phenotype determined in the first set of cells is more similar to the at least one phenotype determined in the third set of cells than the at least one phenotype determined in the second set of cells, wherein the first, second, and third sets of cells were induced pluripotent stem cells, or were cells differentiated from induced pluripotent stem cells, and wherein the comparison is performed on a computer.

The invention also involves methods for reducing the risk of drug toxicity in a human subject, comprising contacting one or more cells differentiated from an induced pluripotent stem cell line generated from the subject with a dose of a pharmacological agent, assaying the contacted one or more differentiated cells for toxicity, and prescribing or administering the pharmacological agent to the subject if, and only if, the assay is negative for toxicity in the contacted cells. The cells differentiated from the induced pluripotent stem cell line may be hepatocytes, cardiomyocytes, or neurons.

The invention also involves methods for identifying a candidate gene that contributes to a human disease, comprising comparing a global gene expression profile of cultured human cells of a differentiated cell type from a plurality of healthy individuals to a global gene expression profile of cultured human cells of the differentiated cell type from a plurality of individuals suffering from the human disease and identifying one or more genes that have different expression levels as candidate genes that contribute to the human disease, wherein the comparison is performed on a computer.

The invention also discloses a human induced pluripotent stem cell line generated from a subject diagnosed as suffering from a health condition, or comprising at least one endogenous allele associated with a health condition or a predisposition for the health condition. The invention also discloses an isolated population of human cells comprising neural stem cells or neurons from a subject having at least one endogenous allele associated with a neurodegenerative disorder, a neurological disorder, or a mood disorder, or from a subject diagnosed with the neurodegenerative disorder, neurological disorder, or mood disorder. The invention also discloses an isolated population of human cells comprising human cardiac progenitor cells or cardiomyocytes from a subject having at least one endogenous allele associated with a cardiovascular disease, or from a subject diagnosed with the cardiovascular disease. The invention also discloses an isolated population of human cells comprising hepatic stem cells or hepatocytes from a subject having at least one endogenous allele associated with a drug sensitivity condition, or from a subject diagnosed with the drug sensitivity condition.

The invention further discloses a panel of genetically diverse human induced pluripotent stem cell lines, comprising human induced pluripotent stem cell lines generated from a plurality of individuals each of which carry at least one polymorphic allele that is unique among the plurality of individuals.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 shows immunofluorescence photomicrographs of staining for ectodermal (TuJ1), mesodermal (Desmin), and endodermal (AFP) lineage markers in cells differentiated from SM10d iPSCs.

DETAILED DESCRIPTION OF THE INVENTION

I. Introduction

Figure 1:
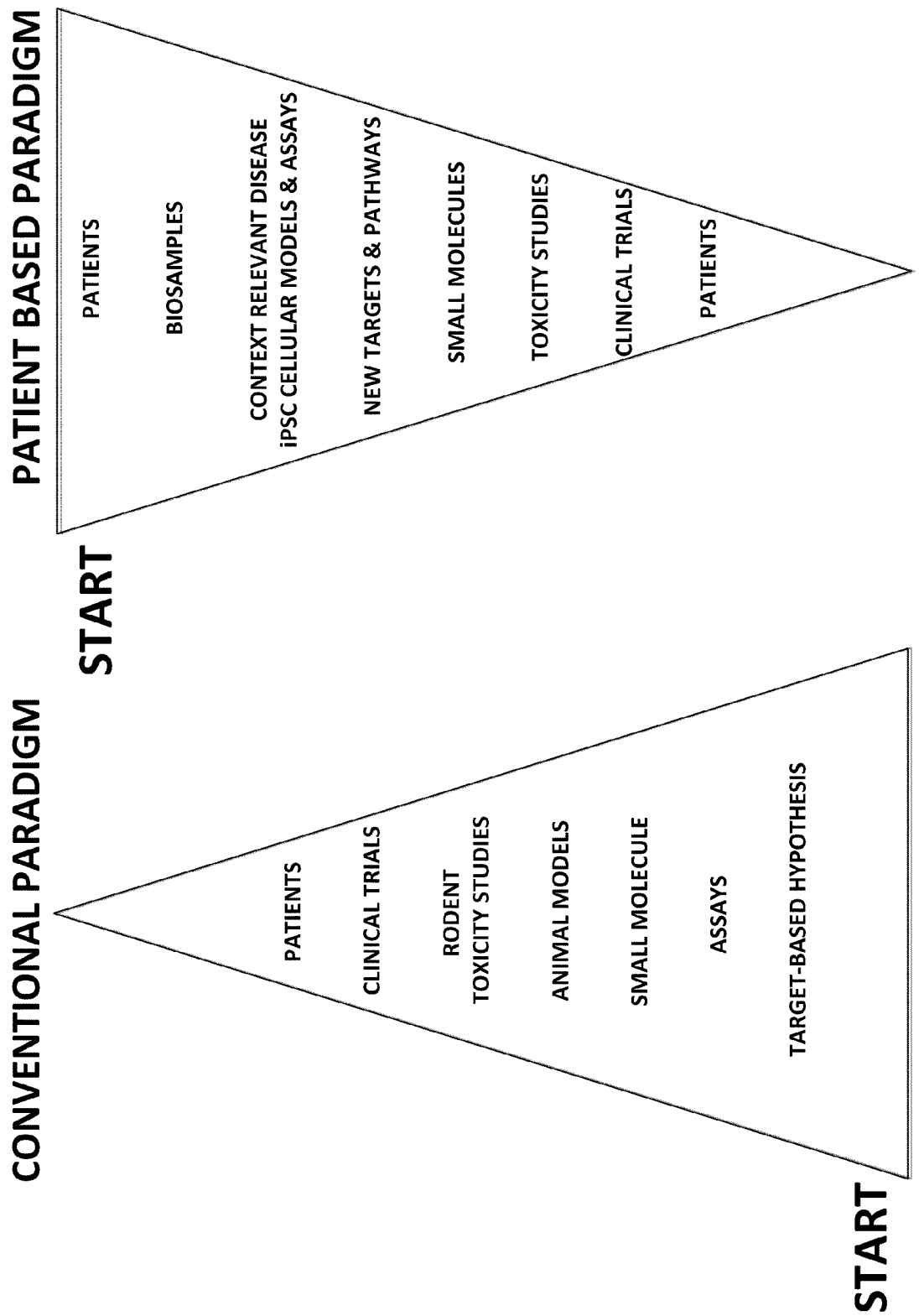
FIG. 1 is a schematic comparison of a traditional drug discovery scheme (left) in which lead compounds are tested against a disease target in heterologous systems (e.g., animal models) prior to testing compound efficacy and safety in patients versus a new drug discovery paradigm (right) in which lead compounds are first identified based on their efficacy in correcting a disease-relevant cellular phenotype in patient-derived, disease-relevant cell types.

Genetic variations (e.g., polymorphic alleles) within and among human patient populations underlie, to a large extent, differences in individual disposition to diseases, disease manifestation, disease severity, and response to treatment (e.g., to drug treatment). The prevalent animal and cellular models for human disease and drug discovery provide a poor representation of the genotypic/phenotypic spectrum extant in the patient populations to be treated. For example, strains of mice and rats commonly used in drug discovery are highly inbred, and thus only represent a very narrow range of possible genotype/phenotype combinations in mice or rats, let alone humans. Likewise, the relatively small number of human cell lines used for drug screening may reflect the genotypic/phenotypic scope of the individuals from which they were derived, but not that of a genetically diverse population. Further, most human cell lines are quite limited in their capacity to generate or phenocopy specific differentiated cell types (e.g., neurons, cardiomyocytes, and hepatocytes) affected by a particular health condition. Also, the cell lines are not representative of cell populations in a subject, since cell lines have been altered to indefinitely replicate. Importantly, in many cases animal models or genetically modified cell models of disease simply fail to adequately recapitulate the cellular disease phenotypes as they actually occur in a human patient's cells. Thus, typical preclinical drug discovery strategies miss many genotype/phenotypes that are present in the human population and will have a direct impact on the therapeutic efficacy and toxicity of a candidate drug compound. A practical consequence of these facts is that more often than not lead compounds fail in human clinical trials despite successful preclinical testing in animal models and transformed cell line models, as mentioned above. Ideally, drug screening and drug target discovery would be performed in biological models that recapitulate the genetic and phenotypic diversity present in a human patient population and the appropriate disease state at the cellular level, well before the clinical trial stage. These drug discovery paradigms are illustrated schematically in FIG. 1. In the traditional drug discovery model (left), candidate therapeutic agents are selected for clinical trials in patients based on their action on specific drug targets and their efficacy/lack of toxicity in animal models. In an alternative drug discovery model (right) the disease-relevant cells derived from patient iPSC lines, as described herein, are the starting point for identification of lead compounds based on their ability to ameliorate a disease-relevant cellular phenotype in patient derived cells.

Accordingly, the present disclosure describes human induced pluripotent stem cell lines from selected individuals (e.g., patients), genetically diverse panels of such cell lines, differentiated cells derived from such cell lines, and methods for their use in disease modeling, drug discovery, diagnostics, and individualized therapy.

II. Definitions

"Candidate drug compound," as used herein, refers to any test compound to be assayed for its ability to affect a functional endpoint. Some examples of such functional endpoints are ligand binding to a receptor, receptor antagonism, receptor agonism, protein-protein interactions, enzymatic activities, transcriptional responses, etc.

"Correcting" a phenotype, as used herein, refers to altering a phenotype such that it more closely approximates a normal phenotype.

"iPSC donor," as used herein, refers to a subject, e.g. a human patient from which one or more induced stem cell lines have been generated. Generally, the genome of an iPSC line corresponds to that of its iPSC donor.

"Phenomic analysis," as used herein, refers to the analysis of phenotypes (e.g., resting calcium level, gene expression profiles, apoptotic index, electrophysiological properties, sensitivity to free radicals, compound uptake and extrusion, kinase activity, second messenger pathway responses) exhibited by a particular type of cell (e.g., cardiomyocytes).

"Phenome," as used herein refers to the set of phenotypes that is subject and cell-type specific. For example, the phenome of hepatocytes and cardiomyocytes from the same individual will be quite distinct even though they share the same genome.

An "endogenous allele," as used herein, refers to a naturally occurring allele that is native to the genome of a cell, i.e., an allele that is not introduced by recombinant methodologies.

An "iPSC-derived cell," as used herein, refers to a cell that is generated from an iPSC either by proliferation of the iPSC to generate more iPSCs, or by differentiation of the iPSC into a different cell type. iPSC-derived cells include cells not differentiated directly from an iPSC, but from an intermediary cell type, e.g., a glial progenitor cell, a neural stem cell, or a cardiac progenitor cell.

A "normal" phenotype, as used herein, refers to a phenotype (e.g., apoptotic rate, resting calcium level, kinase activity, gene expression level) that falls within a range of phenotypes found in healthy individuals or that are not associated with (e.g., predictive of) a health condition.

III. Induced Stem Cell Lines for Drug Screening and Drug Target Discovery

A. Overview

The present disclosure provides human induced pluripotent stem cell (iPSC) lines, panels of stem cell lines, and methods for their use in drug discovery, diagnostic, and therapeutic methods as described in detail below. The induced pluripotent stem cell lines disclosed herein are characterized by long term self renewal, a normal karyotype, and the developmental potential to differentiate into a wide variety of cell types (e.g., neurons, cardiomyocytes, and hepatocytes). Induced pluripotent stem cell lines can be differentiated into cell lineages of all three germ layers, i.e., ectoderm, mesoderm, and endoderm.

Figure 2:
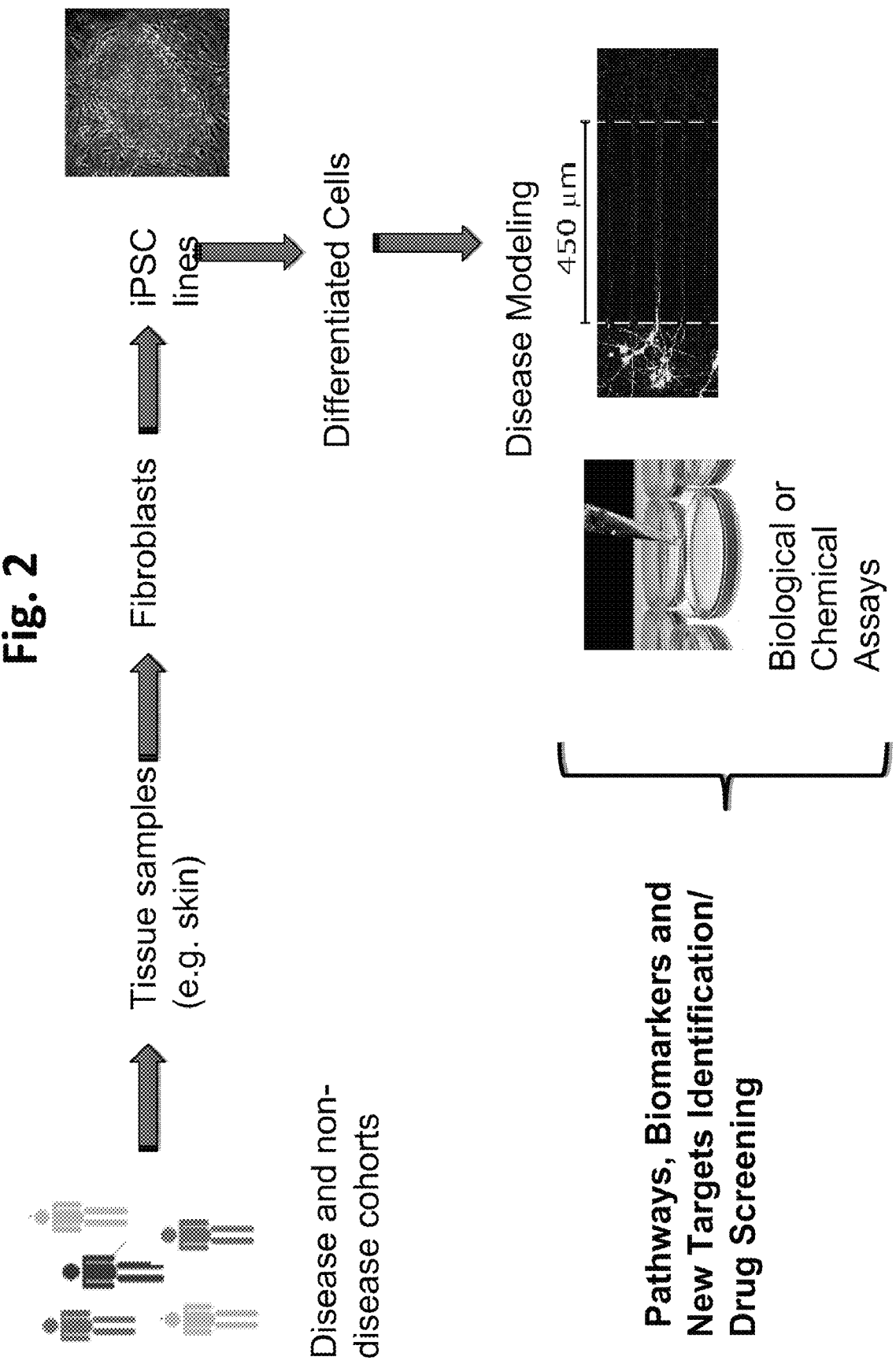
FIG. 2 is an overview of an exemplary, non-limiting, scheme for patient iPSC-based disease modeling and drug discovery.
Figure 3:
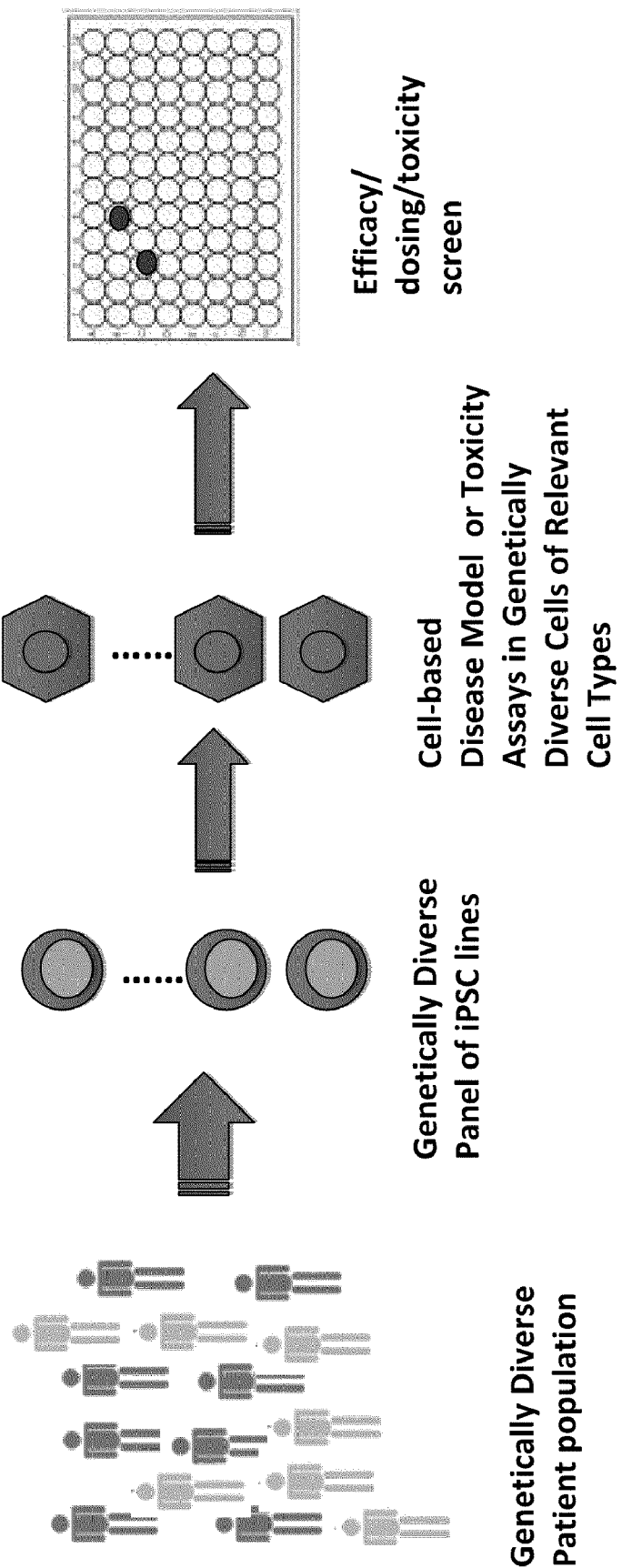
FIG. 3 is an overview of an exemplary, non-limiting, scheme for patient iPSC-based testing of lead drug candidate efficacy and safety in cells from a genetically diverse cohort of patient iPSC lines.

An important nexus exists between a subject (e.g., a patient) and iPSC lines generated from that subject. First, all of the genotypes of iPSC lines and those of the corresponding subject are identical. Thus, genotype-phenotype correlations, uncovered in one are informative for the other, and vice versa. Second, differentiated cells (e.g., neurons) derived ex vivo from an iPSC line will exhibit a complete set of cellular phenotypes (referred to herein as a "phenome") that are very similar, if not identical, to those of differentiated cells in vivo in the corresponding subject. This point is particularly relevant for developing therapeutics targeted to cells that cannot be routinely obtained from patients (e.g., neurons, cardiomyocytes, hepatocytes, or pancreatic cells). For example, in the case of a patient suffering from a neurodegenerative disease (e.g., parkinson's disease), dopaminergic neurons, which are typically affected by this condition, can be obtained non-invasively by differentiating an iPSC line from the subject, and can then be screened in multiple assays. Thus, iPSC lines provide a renewable source of differentiated cells (e.g., inaccessible differentiated cells) in which pathological cellular phenotypes that are associated with a disease, cell type, and individual may be examined and screened against test compounds. An exemplary, non-limiting embodiment of this approach to disease modeling and drug discovery is schematically illustrated in FIG. 2. iPSC lines and iPSC-derived cells (e.g., motor neurons) are also useful for predicting the efficacy and/or adverse side effects of a candidate drug compound in specific individuals or groups of individuals, as schematically illustrated in FIG. 3. For example, test compounds can be tested for toxicity in hepatocytes differentiated from a genetically diverse panel of induced pluripotent stem cells. Toxicity testing in iPSC-derived hepatocytes can reveal both the overall likelihood of toxicity of a test compound in a target patient population, and the likelihood of toxicity in specific patients within that population.

In effect, iPSC lines and iPSC-derived cells (e.g., pancreatic cells) can serve as "cellular avatars," that reveal cellular phenotypes that are disease, cell-type, and subject-specific to the extent the phenotypes are determined or predisposed by the genome. Collectively, panels of patient induced stem cell lines will represent a wide range of genotype/phenotype combinations in a patient population. Thus, they are useful for developing therapeutics that are effective and safe across a wide range of the relevant target population, or for determining which individuals can be treated effectively and safely with a given therapeutic agent.

B. Screening and Selection of Subject Samples

Some of the methods described herein utilize induced stem cell lines or panels of induced stem cell lines derived from subjects that meet one or more pre-determined criteria. In some cases subjects and cellular samples from such subjects may be selected for the generation of induced stem cell lines and panels of induced stem cell lines based on one or more of such pre-determined criteria. These include, but are not limited to, the presence or absence of a health condition in a subject (e.g, spinal muscular atrophy, Parkinson's disease, or amyotrophic lateral sclerosis), one or more positive diagnostic criteria for a health condition, a family medical history indicating a predisposition or recurrence of a health condition, the presence or absence of a genotype associated with a health condition, or the presence of at least one polymorphic allele that is not already represented in a panel of induced stem cell lines.

In some cases, a panel of induced stem cell lines is generated specifically from individuals diagnosed with a health condition, and from subjects that are free of the health condition. Such health conditions include, without limitation, neurodegenerative disorders; neurological disorders such as cognitive impairment, and mood disorders; auditory disease such as deafness; osteoporosis; cardiovascular diseases; diabetes; metabolic disorders; respiratory diseases; drug sensitivity conditions; eye diseases such as macular degeneration; immunological disorders; hematological diseases; kidney diseases; proliferative disorders; genetic disorders, traumatic injury, stroke, organ failure, or loss of limb.

Examples of neurodegenerative disorders include, but are not limited to, Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff's disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis.

Examples of neurological disorders include, stroke, cognitive impairment, and mood disorders.

Examples of immunological disorders include but are not limited to acquired immune deficiency, leukemia, lymphoma, hypersensitivities (allergy), autoimmune diseases, and severe combined immune deficiency.

Examples of autoimmune diseases include but are not limited to acute disseminated encephalomyelitis, addison's disease, ankylosing spondylitis, antiphospholipid antibody syndrome, autoimmune hemolytic anemia, autoimmune hepatitis, bullous pemphigoid, coeliac disease, dermatomyositis, diabetes mellitus type 1, Goodpasture's syndrome, Graves' disease, Guillain-Barré syndrome, Hashimoto's disease, idiopathic thrombocytopenic purpura, lupus erythematosus, multiple sclerosis, myasthenia gravis, pemphigus, pernicious anaemia, polymyositis, primary biliary cirrhosis, rheumatoid arthritis, Sjögren's syndrome, temporal arthritis (also known as "giant cell arthritis"), vasculitis, Wegener's granulomatosis.

Examples of cardiovascular diseases include but are not limited to aneurysm, angina, arrhythmia, atherosclerosis, cardiomyopathy, cerebrovascular accident (stroke), cerebrovascular disease, congenital heart disease, congestive heart failure, myocarditis, valve disease coronary, artery disease dilated, cardiomyopathy, diastolic dysfunction, endocarditis, high blood pressure (hypertension), hypertrophic cardiomyopathy, mitral valve prolapse, myocardial infarction (heart attack), and venous thromboembolism.

Examples of metabolic disorders include but are not limited to acid lipase disease, amyloidosis, Barth Syndrome, biotinidase deficiency, carnitine palmitoyl transferase deficiency type II, central pontine myelinolysis, metabolic diseases of muscle including muscular dystrophy, Farber's Disease, glucose-6-phosphate dehydrogenase deficiency, gangliosidoses, trimethylaminuria, Lesch-Nyhan syndrome, lipid storage diseases, metabolic myopathies, methylmalonic aciduria, mitochondrial myopathies, mucopolysaccharidoses, mucolipidoses, mucolipidoses, mucopolysaccharidoses, multiple CoA carboxylase deficiency, nonketotic hyperglycinemia, Pompe disease, propionic acidemia, type I glycogen storage disease, urea cycle disorders, hyperoxaluria, and oxalosis.

Examples of proliferative disorders include but are not limited to one or more of the following: carcinomas, sarcomas, lymphomas, leukemias, germ cell tumors, blastic tumors, prostate cancer, lung cancer, colorectal cancer, bladder cancer, cutaneous melanoma, breast cancer, endometrial cancer, and ovarian cancer.

Further examples of diseases or disorders may be found in U.S. application Ser. No. 12/157,967; filed on Jun. 13, 2008; First Inventor Kazuhiro Sakurada, 61/061,594; filed on Jun. 13, 2008; First Inventor Kazuhiro Sakurada, and Ser. No. 12/484,152, filed Jun. 12, 2009; First Inventor Kazuhiro Sakurada, which are hereby incorporated by reference. It is also anticipated that the methods of the present invention include marketing and selling products and services for the treatment of diseases and disorders including, but not limited to, those mentioned herein.

Such subjects may be identified in, e.g., gene association studies, clinical studies, and hospitals, preferably after a final diagnosis of a health condition has been made. Preferably, subjects are identified in gene association studies that include non-affected control individuals.

In other cases, iPSC lines are generated from subjects screened for the presence or absence of at least one allele associated with a health condition or a predisposition for a health condition. Such alleles indicate that an individual, though not exhibiting overt symptoms of a health condition, has a high risk of developing the health condition. For example, BRCA1 have been used to indicate a high likelihood of developing breast cancer. Genotyping of subjects may be performed on samples from a number of sources, e.g., blood banks, sperm banks, gene-association studies, hospitals, clinical trials, or any other source as long as a living cellular sample can be obtained from the individual that is genotyped. While not wishing to be bound by theory, it is believed that one or more that cellular phenotypes from individuals carrying alleles associated with health conditions will exhibit abnormalities that can serve as more reliable prognostic indicators of a health condition in combination with a genotype than a genotype alone. Further, identification of specific abnormal cellular phenotypes associated with a health condition may indicate a target pathway for screening of prophylactic and therapeutic agents for the health condition.

There is an ongoing effort to identify associations between polymorphic alleles present in the human population, e.g., single polymorphisms (SNPs) and the occurrence of common health conditions, e.g., neurodegenerative diseases, psychiatric disorders, metabolic disorders, and cardiovascular diseases. Various types of polymorphic alleles can be found in the human genome as summarized in Table 1.

TABLE 1

Types of Interindividual Variation in the Human Genome

| Genetic change/variation | Abbreviation | Description | Frequency in human genome |
|---|---|---|---|
| Single nucleotide polymorphism | SNP | Typically two different nucleotides (biallelic SNPs) at one defined position, but more rarely also triallelic variants occur | 12,000,000 |
| Deletions/Insertions | InDel | Deletions (or insertions, depending on the allele frequencies) of between 1 to 1000 nucleotides. More frequent are deletions of one or three basepairs | >1,000,000 |
| Varying number of tandem recaps | VNTR | Microsatellites also termed short tandem repeat (STR) polymorphisms are typically tandem repeats of two, three or four nucleotides, but repeats up to ten nucleotides in length may also classified in this group.<br>Minisatellites are VNTR polymorphisms in which 10-100 nucleotides are repeated in variable numbers. Repeated segments often do not have exactly identical sequences. | >500,000 |

TABLE 1-continued

Types of Interindividual Variation in the Human Genome

| Genetic change/variation | Abbreviation | Description | Frequency in human genome |
|---|---|---|---|
| Copy number variation | CNV | VNTRs with larger repeat units (100-1000 bp) are termed satellites. Inheritable deletion of multiplication of DNA segments larger than 1 kb. Currently, about 1500 CNVs distributed through all chromosomes are known; estimated to cover 12% of the human genome length. | >1500 loci covering 12% of the genome |

A number of studies have identified alleles associated with a health condition or a predisposition towards a health condition.

Examples of alleles associated with health conditions are known in the art. See, e.g., the databases listed in Table 2.

TABLE 2

List of Publicly Available Databases Containing Alleles Associated with a Health Condition or Predisposition to a Health Condition

| Name of Website | Website URL | Brief Description |
|---|---|---|
| Alzgene | www.alzforum.org/res/com/gen/alzgene | Collection of published genetic association studies performed on Alzheimer Disease phenotypes, from database searches and journals' contents lists. Case and control data presented. |
| Cytokine Gene Polymorphism in Human Disease | www.nanea.dk/cytokinesnps/ | Regularly updated database with Medline-based records from a systematic review of cytokine gene polymorphisms associated with human disease. Data extracted from two publications about the study. |
| HuGE Navigator | hugenavigator.net | HuGE Navigator provides access to a continuously updated knowledge base in human genome epidemiology, including information on population prevalence of genetic variants, gene-disease associations, gene-gene and gene-environment interactions, and evaluation of genetic tests. |
| GenAtlas | www.genatlas.org | Regularly updated database of genes, phenotypes and references. Among numerous databases are brief sections on disorders associated with genes, with lists of citations. May be biased towards statistically significant results. |
| GeneCanvas | genecanvas.idf.inserm.fr | Database of cardiovascular candidate genes and their polymorphisms investigated at INSERM (Paris, France). Data include gene frequencies and linkage disequilibrium statistics. |
| Genetic Association Database | geneticassociationdb.nih.gov | Database of human genetic association studies of complex diseases and disorders, based on Medline records. Data extracted from publications. |

TABLE 2-continued

List of Publicly Available Databases Containing Alleles Associated with a Health Condition or Predisposition to a Health Condition

| Name of Website | Website URL | Brief Description |
|---|---|---|
| Human Obesity Gene Map Database | obesitygene.pbrc.edu | Database of obesity-related genes, including P values for association and references. Biased in favour of statistically significant results. |
| Infevers | fmf.igh.cnrs.fr/infevers | Database of genetic associations in hereditary inflammatory disorders, with voluntarily submitted entries. Submissions are validated by an editorial board member. |
| MedGene | medgene.med.harvard.edu/MEDGENE/ | Automated database of gene disease association studies in Medline. |
| OMIM | www.ncbi.nlm.nih.gov/omim/ | Database of human genes and genetic disorders, containing textual information with links to Medline and sequence records in the Entrez system, and links to additional related resources at NCBI and elsewhere. |
| PharmGKB | www.pharmgkb.org | Database of genomic data and clinical information from participants in pharmacogenetics research studies. Welcomes submission of primary data. |
| T1DBase | t1dbase.org/ | Database of type 1 diabetes data, including information from collaborating laboratories. Some indication given of unpublished data. |

Some examples of health condition-associated alleles and their corresponding studies are provided in Table 3.

TABLE 3

Some Examples of Alleles Associated with a Health Condition

| Disease | Polymorphism(s) identified | References |
|---|---|---|
| Bipolar disorder | rs420259 | The Wellcome Trust Case Control Consortium (2007), *Nature*, 447: 661-678 |
| Coronary artery disease | rs1333049 | The Wellcome Trust Case Control Consortium (2007), *Nature*, 447: 661-678 |
| Crohn's disease | rs17221417 rs11209026 rs10210302 rs9858542 rs17234657 rs1000113 rs10761659 rs10883365 rs17221417 rs2542151 | The Wellcome Trust Case Control Consortium (2007), *Nature*, 447: 661-678 |
| Hypertension | | The Wellcome Trust Case Control Consortium (2007), *Nature*, 447: 661-678 |
| Rheumatoid arthritis | rs6679677 rs6457617 | The Wellcome Trust Case Control Consortium (2007), *Nature*, 447: 661-678 |
| Type 1 Diabetes | rs11761231 rs6679677 rs9272346 rs11171739 rs17696736 rs12708716 | The Wellcome Trust Case Control Consortium (2007), *Nature*, 447: 661-678 |
| Type 2 Diabetes | rs4506565 rs9465871 rs9939609 | The Wellcome Trust Case Control Consortium (2007), *Nature*, 447: 661-678 |
| Gallstone disease | rs1187534 (D19H) | Bush, et al., (2007), *Nat Genet*, 39: 995-999 |
| Myocardial Infarction | rs10757278 | Helgadottir, et al., (2007), *Science*, 316: 1491-1493 |
| Atrial fibrillation | rs2200733 | Gudbjartsson, et al., (2007), *Nature*, 448: 353-357 |
| Type 2 diabetes | rs1801282 rs13266634 rs1111875 rs7903146 rs5219 rs4402960 rs7754840 rs10811661 rs9300039 rs8050136 | Warren, et al., (2007) *Pharmacogenomics*, 7: 180-189 |
| Type 2 diabetes | rs13266634 rs1111875 | Saxena, et al., (2007), *Science*, 316: 1331-1336 |

TABLE 3-continued

Some Examples of Alleles Associated with a Health Condition

| Disease | Polymorphism(s) identified | References |
|---|---|---|
| | rs7903146 | |
| | rs5219 | |
| | rs1801282 | |
| | rs10811661 | |
| | rs4402960 | |
| | rs7754840 | |
| Rheumatoid arthritis | rs3761847 | Plenge, et al., (2007), N Engl J Med, 357: 1199-209 |
| Exfoliation Glaucoma | rs1048661 + rs3825942 | Thorleifsson, et al., (2007), Science, 317: 1397-1400 |
| Breast Cancer | rs2981582 rs12443620 rs8051542 rs889312 rs3817198 rs2107425 rs13281615 | Easton, et al., (2007), Nature, 447: 1087-1093 |
| Colorectal cancer | rs6983267 | Tomlinson, et al., (2007), Nat Genet, 39: 984-988 |

The sequence and other information for any rs-identified SNP can be accessed on the world wide web through the SNP database of the National Center for Biotechnology Information (www.ncbi.nlm.nih.gov/); pulldown menu="SNP."

Subjects may be screened for alleles in genes that affect response to a therapeutic agent or to a class of therapeutic agents. Examples of such alleles include, but are not limited to, alleles of drug metabolizing enzymes, such as Glucose 6 phosphate dehydrogenase (G6PDH), Butyrlcholine esterase, N-acetyltransferase, Cytochrome P450 isoforms (e.g., 2B6, 2D6, C19, 2C9), Thiopurine S-methyltransferase, Dihydropyrimidine dehydrogenase, and Uridin diphospho-glucuronic acid transferase type 1A1. Alleles of Cytochrome P450 enzyme isoforms can be found, e.g., in a database provided under the "Home Page of the Human Cytochrome P450 (CYP) Allele Nomenclature Committee," at "www.cypalleles.ki.se/." Some alleles occur in genes that affect drug transport, including, e.g., multiple drug resistance conferring transporters (MDRs), breast cancer resistance protein (BRCP), multidrug resistance-associated-associated proteins (MRPs), and organic anion-transporting polypeptide (OATP 1B1). Other alleles occur in genes that encode drug targets, including, but not limited to, Vitamin K epoxide reductase, Factor V, G-protein coupled receptors (GPCRs). Of note, GPCRs are one of the most common drug targets. Examples of polymorphic alleles in GPCRs can be found in, e.g., the GPCR Natural Variants ("NaVa") Database, which is accessible on the internet at "nava.liacs.nl/" The GPCR NaVa database describes sequence variants within the family of human G Protein-Coupled Receptors (GPCRs). It includes: rare mutations (frequency<1%); polymorphisms (frequency>1%), including Single Nucleotide Polymorphisms (SNPs); variants without estimates of allele frequency.

Polymorphic alleles of interest may be detected and scored in a nucleic acid sample from a subject by any of a number of methods known in the art. For example, detection of multiple alleles may be performed by conducting a nucleic acid array-based assay on a nucleic acid sample from a subject, where the nucleic acid array comprises allele-specific probes (e.g., SNP-specific probes), which, under high stringency hybridization conditions, selectively hybridize with and discriminate between the nucleic acid sequences of two or more polymorphic alleles of interest, e.g., alleles of G-protein coupled receptors.

The nucleic acid arrays used to detect polymorphisms may be commercially available nucleic acid arrays. For example, the Affymetrix® Genome-Wide SNP Array 6.0 includes probes for more than 906,000 SNPs and more than 946,000 probes for the detection of copy number variation. Alternatively, the nucleic acid arrays may be custom-made to include to a limited subset of alleles of interest. The design of suitable probe arrays for analysis of predetermined polymorphisms and interpretation of the hybridization patterns is described in detail in WO 95/11995; EP 717,113; and WO 97/29212. Such arrays typically contain first and second groups of probes which are designed to be complementary to different allelic forms of the polymorphism. Each group contains a first set of probes, which is subdivided into subsets, one subset for each polymorphism. Each subset contains probes that span a polymorphism and proximate bases and are complementary to one allelic form of the polymorphism. Thus, within the first and second probe groups there are corresponding subsets of probes for each polymorphism. The hybridization patterns of these probes to target samples can be analyzed by footprinting or cluster analysis, as described above. For example, if the first and second probes groups contain subsets of probes respectively complementary to first and second allelic forms of a polymorphic site spanned by the probes, then on hybridization of the array to a sample that is homozygous for the first allelic form all probes in the subset from the first group show specific hybridization, whereas probes in the subset from the second group that span the polymorphism show only mismatch hybridization. The mismatch hybridization is manifested as a footprint of probe intensities in a plot of normalized probe intensity (i.e., target/reference intensity ratio) for the subset of probes in the second group. Conversely, if the target sample is homozygous for the second allelic form, a footprint is observed in the normalized hybridization intensities of probes in the subset from the first probe group. If the target sample is heterozygous for both allelic forms then a footprint is seen in normalized probe intensities from subsets in both probe groups although the depression of intensity ratio within the footprint is less marked than in footprints observed with homozygous alleles. Analysis of the hybridization pattern of a nucleic acid array to a nucleic acid sample indicates which allelic form is present at some or all of the SNP sequences represented on the array. Thus, an individual or an iPSC line generated from an individual can be characterized with a polymorphic profile representing allelic variants of interest, e.g., alleles associated with a health condition.

In other embodiments, an allele is detected using a primer extension reaction or amplification reaction. For example, a nucleic acid sample containing (or suspected of containing) a target nucleic acid molecule can be contacted with an oligonucleotide primer that, upon further contact with a polymerase, can be extended up to and, if desired, beyond the position of the SNP. In addition, the nucleic acid sample can be contacted with an amplification primer pair, comprising a first primer and a second primer, which selectively hybridize to complementary strands of a target nucleic acid molecule and, in the presence of polymerase, allow for generation of an amplification product. For convenience, the primers of an amplification primer pair are referred to as a "first primer" and a "second primer"; however, reference herein to a "first primer" or a "second primer" is not intended to indicate any importance, order of addition, or the like. It will be further recognized that an amplification primer pair requires that the first and second primer comprise what are commonly referred to as a forward primer and a reverse primer.

A primer extension or PCR amplification reaction can be designed such that the presence of a particular nucleotide at an SNP position can be determined by the presence or size of the extension and/or amplification product, in which case the SNP can be determined using a method such as gel electrophoresis, capillary gel electrophoresis, or mass spectrometry; or the amplification product can be sequenced to determine the nucleotide at the SNP position. In addition, the SNP can be detected indirectly, for example, by further contacting the sample with a detector oligonucleotide, which can selectively hybridize to a nucleotide sequence of the first amplification product comprising the SNP position; and detecting selective hybridization of the detector oligonucleotide, as above.

Various other methods useful for genotyping are known to the art and can be applied to the present methods. For example, PCR can be performed using TaqMan® reagents, followed by reading the plates at this endpoint. Molecular beacons, Amplifluor® or TriStar® reagents and methods similarly can be used (Stratagene; Intergen). Amplification products also can be detected using an ELISA format, for example, using a design in which one primer is biotinylated and the other contains digoxygenin. The amplification products are then bound to a streptavidin plate, washed, reacted with an enzyme-conjugated antibody to digoxygenin, and developed with a chromogenic, fluorogenic, or chemiluminescent substrate for the enzyme. Alternatively, a radioactive method can be used to detect generated amplification products, for example, by including a radiolabeled deoxynucleoside triphosphate into the amplification reaction, then blotting the amplification products onto DEAE paper for detection. In addition, if one primer is biotinylated, then streptavidin-coated scintillation proximity assay plates can be used to measure the PCR products. Additional methods of detection can use a chemiluminescent label, for example, a lanthanide chelate such as used in the DELFIA® assay (Pall Corp.), an electrochemiluminescent label such as ruthenium tris-bipyridy (ORI-GEN), or a fluorescent label, for example, using fluorescence correlation spectroscopy.

An assay system that is commercially available and can be used to identify a nucleotide occurrence of one or more SNPs is the SNP-IT® assay system (Orchid BioSciences, Inc.; Princeton N.J.). In general, the SNP-IT® method is a three step primer extension reaction. In the first step a target nucleic acid molecule is isolated from a sample by hybridization to a capture primer, which provides a first level of specificity. In a second step the capture primer is extended from a terminating nucleotide triphosphate at the target SNP site, which provides a second level of specificity. In a third step, the extended nucleotide triphosphate can be detected using a variety of known formats, including, for example, by direct fluorescence, indirect fluorescence, an indirect colorimetric assay, mass spectrometry, or fluorescence polarization. Reactions conveniently can be processed in 384 well format in an automated format using a SNP Stream® instrument (Orchid BioSciences, Inc.).

Various methods for genotyping SNP alleles, selected as described herein, are readily adaptable to high throughput assays. For example, an amplification reaction such as PCR can be performed using inexpensive robotic thermocyclers for a specified number of cycles, then the amplification product generated can be determined at the endpoint of the reaction. Furthermore, the methods can be performed in a multiplex format, for example, using differentially labeled oligonucleotide probes, or performing oligonucleotide ligation assays that result in different sized ligation products, or amplification reactions that result in different sized amplification products. In another example, high-throughput mass spectrometry is used to detect SNP alleles in a target nucleic acid sample. Mass spectrometric methods for SNP genotyping are described in, e.g., U.S. Pat. Nos. 7,132,519, 6,994, 998; and U.S. Patent Application No 20060275789.

Where hybridization-based methods are used, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art; see for example Maniatis et al. (1989), Molecular Cloning: A Laboratory Manual, 2d Edition; and Short Protocols in Molecular Biology, ed. Ausubel, et al. Stringent conditions are sequence-dependent and will be different in different circumstances. Longer sequences hybridize specifically at higher temperatures. An extensive guide to the hybridization of nucleic acids is found in Tijssen (1993), Techniques in Biochemistry and Molecular Biology—Hybridization with Nucleic Acid Probes, "Overview of principles of hybridization and the strategy of nucleic acid assays." Generally, stringent conditions are selected to be about 5-10 C lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g. 10 to 50 nucleotides) and at least about 60 C for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art. See, e.g., Maniatis and Ausubel, supra, and Tijssen, supra.

C. Methods for Inducing Pluripotent Stem Cell Lines iPSC lines may be induced from a wide variety of mammalian cells, e.g., human somatic cells, such as fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, gastric epithelial cells, lung epithelial cells, synovial cells, kidney cells, skin epithelial cells or osteoblasts. Methods for inducing multipotent and pluripotent stem cell lines are further disclosed in U.S. application Ser. No. 12/157,967; filed Jun. 13, 2008; first inventor Kazuhiro Sakurada, 61/061,594; filed on Jun. 13, 2008; First Inventor Kazuhiro Sakurada, and 61/061,565; filed on Jun. 13, 2008; First Inventor Kazuhiro Sakurada, which are hereby incorporated by reference in their entirety.

The cells to be induced can originate from many different types of tissue, e.g., bone marrow, skin (e.g., dermis, epidermis), muscle, adipose tissue, peripheral blood, foreskin, skeletal muscle, or smooth muscle. The cells can also be derived from neonatal tissue, including, but not limited to: umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.).

The cells can be derived from neonatal or post-natal tissue collected from a mammal within the period from birth, including cesarean birth, to death. For example, the tissue may be from a mammal who is >10 minutes old, >1 hour old, >1 day old, >1 month old, >2 months old, >6 months old, 1 year old, >2 years old, >5 years old, >10 years old, >15 years old, >18 years old, >25 years old, >35 years old, 45 years old, >55 years old, >65 years old, <80 years old, <70 years old, <60 years old, <50 years old, <40 years old, <30 years old, <20 years old or <10 years old. In some examples, the tissue is from a human age 18, 20, 21, 23, 24, 25, 28, 29, 31, 33, 34, 35, 37, 38, 40, 41, 42, 43, 44, 47, 51, 55, 61, 63, 65, 70, 77, or 85 years old.

The cells may be from non-embryonic tissue, e.g., at a stage of development later than the embryonic stage. In some cases, the cells may be derived from a fetus. In some cases, the cells are not from a fetus. In some cases, the cells are from an embryo. In some cases, the cells are not from an embryo.

The cells can be obtained from a single cell or a population of cells. The population may be homogenous or heterogeneous. The cells may be a population of cells found in a human cellular sample, e.g., a biopsy or blood sample. In some cases, the cells are a cell line. In some cases, the cells are somatic cells. In some cases, the cells are derived from cells fused to other cells. In some cases, the cells are not derived from cells fused to other cells. In some cases, the cells are not derived from cells artificially fused to other cells. In some cases, the cells are not: a cell that has been fused with an embryonic stem cell, or a cell that has undergone the procedure known as somatic cell nuclear transfer.

The cellular population may include both differentiated and undifferentiated cells. In some cases, the population primarily contains differentiated cells. In other cases, the population primarily contains undifferentiated cells, e.g., undifferentiated stem cells. The undifferentiated cells within the population may be induced to become pluripotent or multipotent. In some cases, differentiated cells within the cellular population are induced to become pluripotent or multipotent.

The cellular population may include undifferentiated cells such as mesenchymal stem cells (MSCs), see, e.g., Pittenger et al. (1999), Science 284 (5411): 143-7, multipotent adult progenitor cells (MAPCs), see, e.g., Jahagirdar et al. (2005), Stem Cell Rev. 1(1): 53-9, and/or marrow-isolated adult multilineage inducible (MIAMI) cells (D'Ippolioto et al., (2004), J. Cell Sci. 117 (Pt 14): 2971-81. MSCs are multipotent cells that arise from the mesenchyme during development. In some cases, the undifferentiated stem cells (e.g., mesenchymal stem cells, MAPCs and MIAMI cells) are stem cells that have not undergone epigenetic inactivating modification by heterochromatin formation due to DNA methylation or histone modification of at least four genes, at least three genes, at least two genes, at least one gene, or none of the following: Nanog, Oct3/4, Sox2 and Tert. Activation, or expression of such genes, e.g., Tert, Nanog, Oct3/4 or Sox2, may occur when human pluripotent stem cells are induced from undifferentiated stem cells present in a human postnatal tissue.

Methods for obtaining human somatic cells are well established, as described in, e.g., Schantz and Ng (2004), A Manual for Primary Human Cell Culture, World Scientific Publishing Co., Pte, Ltd. In some cases, the methods include obtaining a cellular sample, e.g., by a biopsy, blood draw, or alveolar or other pulmonary lavage. Other suitable methods for obtaining various types of human somatic cells include, but are not limited to, the following exemplary methods:

Bone Marrow

The donor is given a general anesthetic and placed in a prone position. From the posterior border of the ilium, a collection needle is inserted directly into the skin and through the iliac surface to the bone marrow, and liquid from the bone marrow is aspirated into a syringe. A mononuclear cell fraction is then prepared from the aspirate by density gradient centrifugation. The collected crude mononuclear cell fraction is then cultured prior to use in the methods described herein for induction pluripotency. For convenience, methods for induction of pluripotency, as described herein, are collectively referred to as "induction."

Postnatal Skin

Skin tissue containing the dermis is harvested, for example, from the back of a knee or buttock. The skin tissue is then incubated for 30 minutes at 37° C. in 0.6% trypsin/DMEM (Dulbecco's Modified Eagle's Medium)/F-12 with 1% antibiotics/antimycotics, with the inner side of the skin facing downward.

After the skin tissue is turned over to scrub slightly the inner side with tweezers, the skin tissue is finely cut into 1 mm2 sections using scissors, which are then centrifuged at 1200 rpm and room temperature for 10 minutes. The supernatant is removed, and to the tissue precipitate is added 25 ml of 0.1% trypsin/DMEM/F-12/1% antibiotics, antimycotics, and stirred using a stirrer at 37° C. and 200-300 rpm for 40 minutes. After confirming that the tissue precipitate is fully digested, 3 ml fetal bovine serum (FBS) (manufactured by JRH) is added, and filtered sequentially with gauze (Type I manufactured by PIP), a 100 μm nylon filter (manufactured by FALCON) and a 40 μm nylon filter (manufactured by FALCON). After centrifuging the resulting filtrate at 1200 rpm and room temperature for 10 minutes to remove the supernatant, DMEM/F-12/1% antibiotics, antimycotics is added to wash the precipitate, and then centrifuged at 1200 rpm and room temperature for 10 minutes. The cell fraction thus obtained is then cultured prior to induction.

Postnatal Skeletal Muscle

After the epidermis of a connective tissue containing muscle such as the lateral head of the biceps brachii muscle or the sartorius muscle of the leg is cut and the muscle tissue is excised, it is sutured. The whole muscle obtained is minced with scissors or a scalpel, and then suspended in DMEM (high glucose) containing 0.06% collagenase type IA and 10% FBS, and incubated at 37° C. for 2 hours.

By centrifugation, cells are collected from the minced muscle, and suspended in DMEM (high glucose) containing 10% FBS. After passing the suspension through a microfilter with a pore size of 40 μm and then a microfilter with a pore size of 20 μm, the cell fraction obtained may be cultured according to the method described in 6. below as crude purified cells containing undifferentiated stem cells, and used for the induction of human pluripotent stem cells of the present invention.

Postnatal Adipose Tissue

Cells derived from adipose tissue for use in the present invention may be isolated by various methods known to a person skilled in the art. For example, such a method is described in U.S. Pat. No. 6,153,432, which is incorporated herein in its entirety. A preferred source of adipose tissue is omental adipose tissue. In humans, adipose cells are typically isolated by fat aspiration.

In one method of isolating cells derived from adipose cells, adipose tissue is treated with 0.01% to 0.5%, preferably 0.04% to 0.2%, and most preferably about 0.1% collagenase, 0.01% to 0.5%, preferably 0.04%, and most preferably about 0.2% trypsin and/or 0.5 ng/ml to 10 ng/ml dispase, or an effective amount of hyaluronidase or DNase (DNA digesting enzyme), and about 0.01 to about 2.0 mM, preferably about 0.1 to about 1.0 mM, most preferably 0.53 mM concentration of ethylenediaminetetraacetic acid (EDTA) at 25 to 50° C., preferably 33 to 40° C., and most preferably 37° C. for 10 minutes to 3 hours, preferably 30 minutes to 1 hour, and most preferably 45 minutes.

Cells are passed through nylon or a cheese cloth mesh filter of 20 microns to 800 microns, more preferably 40 microns to 400 microns, and most preferably 70 microns. Then the cells in the culture medium are subjected to differential centrifugation directly or using Ficoll or Percoll or another particle gradient. The cells are centrifuged at 100 to 3000×g, more preferably 200 to 1500×g, most preferably 500×g for 1 minute to 1 hours, more preferably 2 to 15 minutes and most preferably 5 minutes, at 4 to 50° C., preferably 20 to 40° C. and more preferably about 25° C.

The adipose tissue-derived cell fraction thus obtained may be cultured according to the method described herein as crude purified cells containing undifferentiated stem cells, and used for the induction of human pluripotent or multipotent stem cells.

Blood

About 50 ml to about 500 ml vein blood or cord blood is collected, and a mononuclear cell fraction is obtained by the Ficoll-Hypaque method, as described in, e.g., Kanof et al. (1993), Current Protocols in Immunology (J. E. Coligan, A. M. Kruisbeek, D. H. Margulies, E. M. Shevack, and W. Strober, eds.), ch. 7.1.1.-7.1.5, John Wiley & Sons, New York).

After isolation of the mononuclear cell fraction, approximately $1 \times 10^7$ to $1 \times 10^8$ human peripheral blood mononuclear cells are suspended in a RPMI 1640 medium containing 10% fetal bovine serum, 100 μg/ml streptomycin and 100 units/ml penicillin, and after washing twice, the cells are recovered. The recovered cells are resuspended in RPMI 1640 medium and then plated in a 100 mm plastic petri dish at a density of about $1 \times 10^7$ cells/dish, and incubated in a 37° C. incubator at 8% $CO_2$. After 10 min remaining in suspension are removed and adherent cells are harvested by pipetting. The resulting adherent mononuclear cell fraction is then cultured prior to the induction period as described herein. In some cases, the peripheral blood-derived or cord blood-derived adherent cell fraction thus obtained may be cultured according to the method described herein as crude purified cells containing undifferentiated stem cells, and used for the induction of human pluripotent stem cells of the present invention.

Induction

During the induction process, forced expression of certain polypeptides is carried out in cultured cells for a period of time, after which the iPSCs are screened for a number of morphological and gene expression properties that characterize multipotent and pluripotent stem cells. Induced cells that meet these screening criteria may then be subcloned and expanded. In some cases, the cells to be induced may be cultured for a period of time prior to the induction procedure. Alternatively, the cells to be induced may be used directly in the induction process without a prior culture period. In some embodiments, the type of cell culture medium used is the same or very similar before, during, and after the induction process. In other cases, different cell culture media are used at different points. For example, one type of culture medium may be used directly before the induction process, while a second type of media is used during the induction process. At times, a third type of culture medium is used during the induction process.

Cells may be cultured in medium supplemented with a particular serum. In some embodiments, the serum is fetal bovine serum (FBS). The serum can also be fetal calf serum (FCS). In some cases, the serum may be Human AB serum. Mixtures of serum may also be used, e.g. mixture of FBS and Human AB, FBS and FCS, or FCS and Human AB.

Culture of cells may be carried out under a low serum culture conditions prior to, during, or following induction. A "low serum culture condition" refers to the use of a cell culture medium containing a concentration of serum ranging from 0% (v/v) (i.e., serum-free) to about 5% (v/v), e.g., 0% to 2%, 0% to 2.5%, 0% to 3%, 0% to 4%, 0% to 5%, 0.1% to 2%, 0.1% to 5%, 0.1%, 0.5%, 1%, 1.2%, 1.5%, 2%, 2.5%, 3%, 3.5%, or 4%. In some embodiments, the serum concentration is from about 0% to about 2%. In some cases, the serum concentration is about 2%. In some cases, the serum concentration is preferably 2% or less. In other embodiments, cells are cultured under a "high serum condition," i.e., greater than 5% serum to about 20% serum, e.g., 6%, 7%, 8%, 10%, 12%, 15%, or 20%. Culturing under high serum conditions may occur prior to, during, and/or after induction.

Some representative media that the cells can be cultured in include: MAPC, FBM, ES, MEF-conditioned ES (MC-ES), and mTeSR™ (available, e.g., from StemCell Technologies, Vancouver, Canada), See Ludwig et al (2006), Nat Biotechnol, 24(2): 185-187. In other cases, alternative culture conditions for growth of human ES cells are used, as described in, e.g., Skottman et al (2006), Reproduction, 132(5):691-698. In some embodiments, the cells are cultured in MAPC, FBM, MC-ES, or mTeSR™ prior to and/or during the introduction of induction factors to the cells; and the cells are cultured in MC-ES or mTeSR™ medium later in the induction process.

MAPC (2% FBS) Medium may comprise: 60% Dulbecco's Modified Eagle's Medium-low glucose, 40% MCDB 201, Insulin Transferrin Selenium supplement, (0.01 mg/ml insulin; 0.0055 mg/ml transferrin; 0.005 μg/ml sodium selenite), 1× linolenic acid albumin (1 mg/mL albumin; 2 moles linoneic acid/mole albumin), 1 nM dexamethasone, 2% fetal bovine serum, 1 nM dexamethasone, 10-4 M ascorbic acid, and 10 μg/ml gentamycin.

FBM (2% FBS) Medium may comprise: MCDB202 modified medium, 2% fetal bovine serum, 5 μg/ml insulin, 50 mg/ml gentamycin, and 50 ng/ml amphotericin-B.

ES Medium may comprise: 40% Dulbecco's Modified Eagle's Medium (DMEM) 40% F12 medium, 2 mM L-glutamine, 1× non-essential amino acids (Sigma, Inc., St. Louis, Mo.), 20% Knockout Serum Replacement™ (Invitrogen, Inc., Carlsbad, Calif.), and 10 μg/ml gentamycin.

MC-ES medium may be prepared as follows. ES medium is conditioned on mitomycin C-treated murine embryonic fibroblasts (MEFs), harvested, filtered through a 0.45-μM filter, and supplemented with about 0.1 mM β mercaptoethanol, about 10 ng/ml bFGF or FGF-2, and, optionally, about 10 ng/ml activin A. In some cases, irradiated MEFs are used in place of the mitomycin C-treated MEFs.

When either low or high serum conditions are used for culturing the cells, one or more growth factors such as fibroblast growth factor (FGF)-2; basic FGF (bFGF); platelet-derived growth factor (PDGF), epidermal growth factor (EGF); insulin-like growth factor (IGF); or insulin can be included in the culture medium. Other growth factors that can be used to supplement cell culture media include, but are not limited to one or more: Transforming Growth Factor β-1 (TGF β-1), Activin A, Noggin, Brain-derived Neurotrophic Factor (BDNF), Nerve Growth Factor (NGF), Neurotrophin (NT)-1, NT-2, or NT 3. In some cases, one or more of such factors is used in place of the bFGF or FGF-2 in the MC-ES medium or other cell culture medium.

In some cases, the concentration of growth factors in the culture media described herein (e.g., MAPC, FBM, MC-ES, mTeSR™) is from about 2 ng/ml to about 20 ng/ml, e.g., about 2 ng/ml, 3 ng/ml, 4 ng/ml, 5 ng/ml, 6 ng/ml, 7 ng/ml, 8 ng/ml, 10 ng/ml, 12 ng/ml, 14 ng/ml, 15 ng/ml, 17 ng/ml, or 20 ng/ml. In some embodiments, the concentration of bFGF or FGF2 is from about 2 ng/ml to about 5 ng/ml; from about 5 ng/ml to about 8 ng/ml; from about 9 ng/ml to about 11 ng/ml; from about 11 ng/ml to about 15 ng/ml; or from about 15 ng/ml to about 20 ng/ml.

The growth factors may be used alone or in combination. For example, FGF-2 may be added alone to the medium; in another example, both PDGF and EGF are added to the culture medium.

In some examples, following initiation of the forced expression of genes or polypeptides (e.g., immediately after a retroviral infection period) in cells, the "iPSCs" are maintained in MC-ES medium as described herein.

In some embodiments, cells are maintained in the presence of a rho, or rho-associated, protein kinase (ROCK) inhibitor to reduce apoptosis. In some cases, an inhibitor of Rho associated kinase is added to the culture medium. For example, the addition of Y-27632 (Calbiochem; water soluble) or Fasudil (HA1077: Calbiochem), an inhibitor of Rho associated kinase (Rho associated coiled coil-containing protein kinase) may be used to culture the human pluripotent stem cells of the present invention. In some cases the concentration of Y-27632 or Fasudil, is from about 5 µM to about 20 µM, e.g., about 5 µM, 10 µM, 15 µM, or 20 µM.

The cells may be cultured for about 1 to about 12 days e.g., 2 days, 3 days, 4.5 days, 5 days, 6.5 days, 7 days, 8 days, 9 days, 10 days, or any other number of days from about 1 day to about 12 days prior to undergoing the induction methods described herein.

In some cases, the iPSCs are cultured in complete ES medium in a 37° C., 5% $CO_2$ incubator, with medium changes about every 1 to 2 days. In some embodiments, induced the iPSCs are cultured and observed for about 14 days to about 40 days, e.g., 15, 16, 17, 18, 19, 20, 23, 24, 27, 28, 29, 30, 31, 33, 34, 35, 36, 37, 38 days, or any other period from about 14 days to about 40 days prior to identifying and selecting clones comprising "iPSCs" based on morphological characteristics. Morphological characteristics for identifying iPSC clones include, but are not limited to, a small cell size with a high nucleus-to-cytoplasm ratio; formation of small monolayer colonies within the space between parental cells (e.g., between fibroblasts).

The cells may be plated at a cell density of about $1\times10^3$ cells/cm$^2$ to about $1\times10^4$ cells/cm$^2$, e.g., $2\times10^3$ cells/cm$^2$, $3.5\times10^3$ cells/cm$^2$, $6\times10^3$ cells/cm$^2$, $7\times10^3$ cells/cm$^2$, $9\times10^3$ cells/cm$^2$, or any other cell density from about $1\times10^3$ cells/cm$^2$ to about $1\times10^4$ cells/cm$^2$.

The cells can be plated and cultured directly on tissue culture-grade plastic. Alternatively, cells are plated and cultured on a coated substrate, e.g., a substrate coated with fibronectin, gelatin, Matrigel™, collagen, or laminin. Suitable cell culture vessels include, e.g., 35 mm, 60 mm, 100 mm, and 150 mm cell culture dishes, 6-well cell culture plates, and other size-equivalent cell culture vessels. In some cases, the cells are cultured with feeder cells. For example, the cells may be cultured on a layer, or carpet, of MEFs.

Media with low concentrations of serum may be particularly useful to enrich for undifferentiated stem cells. The undifferentiated cells cultured under low serum conditions may or may not share certain properties with MSCs, MAPCs, and/or MIAMI cells. Differences in phenotype may be due, in part, to culture methods used to obtain MSCs, MAPCs and MIAMI cells. For example, MSCs are often obtained by isolating the non-hematopoeitic cells (e.g., interstitial cells) adhering to a plastic culture dish when tissue, e.g., bone marrow, fat, muscle, or skin etc., is cultured in a culture medium containing a high-concentration serum (5% or more). However, even under these culture conditions, a very small number of undifferentiated cells can be maintained, especially if the cells were passaged under certain culture conditions (e.g., low passage number or low-density culturing).

In some embodiments, in order to culture and grow human pluripotent stem cells induced from the undifferentiated stem cells of the present invention present in a human postnatal tissue, it is preferred that the cells are subcultured every 5 to 7 days in a culture medium containing the additives described herein on a MEF-covered plastic culture dish or a matrigel-coated plastic culture dish. In some cases, the cells may be cultured at a low density, which may be accomplished by splitting the cells from about 1:6 to 1:3 or by plating the cells at $10^3$ cells/cm$^2$ to $3\times10^4$ cells/cm$^2$.

Primary culture ordinarily occurs immediately after the cells are isolated from a donor, e.g., human. The primary cells can be subjected to a second subculture, a third subculture, a fourth subculture, and greater than four subcultures. A "second" subculture describes primary culture cells subcultured once, a "third" subculture describes primary cultures subcultured twice, a "fourth" subculture describes primary cells subcultured three times, etc. The culture techniques described herein may generally include culturing from the period between the primary culture and the fourth subculture, but other culture periods may also be employed. Preferably, cells are cultured from primary culture to second subculture.

Inducing a cell to become pluripotent can be accomplished in numerous ways. In some embodiments, the methods for induction of pluripotency in one or more cells include forcing expression of a set of induction factors (IFs). In some cases, the set of IFs includes one or more: an Oct3/4 polypeptide, a Sox2 polypeptide, a Klf4 polypeptide, or a c-Myc polypeptide. In some cases, the set does not include a c-Myc polypeptide. For example, the set of IFs can include: an Oct3/4 polypeptide, a Sox2 polypeptide, and a Klf4 polypeptide, but not a c-Myc polypeptide. In some cases, the set of IFs does not include polypeptides that might increase the risk of cell transformation.

In some cases, the set may include a c-Myc polypeptide. In certain cases, the c-Myc polypeptide is a constitutively active variant of c-Myc. In some instances, the set includes a c-Myc polypeptide capable of inducible activity, e.g., a c-Myc-ER polypeptide, see, e.g., Littlewood, et al. (1995) Nucleic Acid Res. 23(10):1686-90.

In other cases, the set of IFs may include: an Oct3/4 polypeptide, a Sox2 polypeptide, and a Klf4 polypeptide, but not a TERT polypeptide, a SV40 Large T antigen polypeptide, HPV16 E6 polypeptide, a HPV16 E7 polypeptide, or a Bmi1 polypeptide. In some cases, the set of IFs does not include a TERT polypeptide. In some cases, the set of IFs does not include a SV40 Large T antigen. In other cases, the set of IFS does not include a HPV16 E6 polypeptide or a HPV16 E7 polypeptide.

In some cases, the set of IFs includes three IFs, wherein two of the three IFs are an Oct3/4 polypeptide and a Sox2 polypeptide. In other cases, the set of IFs includes two IFs, wherein the two polypeptides are a c-Myc polypeptide and a Sox2 polypeptide In some cases, the set of induction factors is limited to Oct 3/4, Sox2, and Klf4 polypeptides. In other cases, the set of induction factors may be limited to a set of four IFs: an Oct3/4 polypeptide, a Sox2 polypeptide, a Klf4 polypeptide, and a c-Myc polypeptide.

A set of IFs may include IFs in addition to an Oct 3/4, a Sox2, and a Klf4 polypeptide. Such additional IFs include, but are not limited to Nanog, TERT, LIN28, CYP26A1, GDF3, FoxD3, Zfp42, Dnmt3b, Ecat1, and Tcl1 polypeptides. In some cases, the set of additional IFs does not include a c Myc polypeptide. In some cases, the set of additional IFs does not include polypeptides that might increase the risk of cell transformation.

Forced expression of IFs may be maintained for a period of at least about 7 days to at least about 40 days, e.g., 8 days, 9 days, 10 days, 11 days, 12 days, 13 days, 14 days, 15 days, 16 days, 17 days, 18 days, 19 days, 20 days, 21 days, 25 days, 30 days, 33 days, or 37 days.

The efficiency of inducing pluripotency in cells of a human population of cells is from at least about 0.001% to at least about 0.01% of the total number of cells to be induced, e.g., 0.002%, 0.0034%, 0.004%, 0.005%, 0.0065%, 0.007%, 0.008%, or 0.0085%.

D. HDAC Inhibitor

Induction of the cells may be accomplished by combining histone deacetylase (HDAC) inhibitor treatment with forced expression of sets of IFs. The cells to be induced may be undifferentiated stem cells present in a human postnatal tissue. In other cases, the cells to be induced are differentiated cells or are a mixture of differentiated or undifferentiated cells.

The HDAC may be combined with the forced expression of a specific set of IFs, e.g., Oct 3/4, a Sox2, and a Klf4. For example, a human somatic cell is induced to become pluripotent after HDAC inhibitor treatment is combined with forced expression of Oct3/4, Sox2 and Klf4 or forced expression of Oct3/4, Sox2, Klf4, and c-Myc. In some cases, human pluripotent stem cells can be induced by introducing three genes of Oct3/4, Sox2 and Klf4 or three genes of Oct3/4, Sox2 and Klf4 plus the c-Myc gene or a HDAC inhibitor into undifferentiated stem cells present in a human postnatal tissue in which each gene of Tert, Nanog, Oct3/4 and Sox2 has not undergone epigenetic inactivation. In still other cases, human pluripotent stem cells are induced by introducing three genes of Oct3/4, Sox2 and Klf4 or three genes of Oct3/4, Sox2 and Klf4 plus the c-Myc gene or a histone deacetylase inhibitor into undifferentiated stem cells after the undifferentiated stem cells were amplified by a primary culture or a second subculture, or a subculture in a low density and subculturing in a culture medium comprising a low-concentration serum.

Cells may be treated with one or more HDACs for about 2 hours to about 5 days, e.g., 3 hours, 6 hours, 12 hours, 14 hours, 18 hours, 1 day, 2 days, 3 days, or 4 days. Treatment with HDAC inhibitor may be initiated prior to beginning forced expression of IFs in the cells. In some cases, HDAC inhibitor treatment begins during or after forced expression of IFs in the cells. In other cases, HDAC inhibitor treatment begins prior to forced expression and is maintained during forced expression.

Suitable concentrations of an HDAC inhibitor range from about 0.001 nM to about 10 mM, depending on the particular HDAC inhibitor to be used, but are selected so as to not significantly decrease cell survival in the treated cells. The HDAC concentration may range from 0.01 nM, to 1000 nM. In some embodiments, the HDAC concentration ranges from about 0.01 nM to about 1000 nM, e.g., about 0.05 nM, 0.1 nM, 0.5 nM, 0.75 nM, 1.0 nM, 1.5 nM, 10 nM, 20 nM, 40 nM, 50 nM, 100 nM, 200 nM, 300 nM, 500 nM, 600 nM, 700 nM, 800 nM, or other concentration from about 0.01 nM to about 1000 nM. Cells are exposed for 1 to 5 days or 1 to 3 days. For example, cells are exposed 1 day, 2 days, 3 days, 4 days or 5 days.

Multiple varieties of HDAC inhibitors can be used for the induction experiments. In a preferred embodiment, the HDAC inhibitor MS-275 is used. Examples of suitable HDAC inhibitors include, but are not limited to, any the following:

A. Trichostatin A and its analogs, for example: trichostatin A (TSA); and trichostatin C (Koghe et al. 1998, Biochem. Pharmacol. 56: 1359-1364).

B. Peptides, for example: oxamflatin [(2E)-5-[3-[(phenylsulfonyl)aminophenyl]-pent-2-ene-4-inohydroxamic acid (Kim et al., Oncogene 18: 2461-2470 (1999)); Trapoxin A (cylco-(L-phenylalanyl-L-phenylalanyl-D-pipecolinyl-L-2-amino-8-oxo-9,10-epoxy-decanoyl) (Kijima et al., J. Biol. Chem. 268: 22429-22435 (1993)); FR901228, depsipeptide (Nakajima et al., Ex. Cell RES. 241: 126-133 (1998)); FR225497, cyclic tetrapeptide (H. Mori et al., PCT International Patent Publication WO 00/08048 (Feb. 17, 2000)); apicidin, cyclic tetrapeptide [cyclo-(N—O-metyl-L-tryptophanyl-L-isoleucinyl-D-pipecolinyl-L-2-amino-8-oxodecanoyl)] (Darkin-Rattray et al., Proc. Natl. Acad. Sci. U.S.A. 93: 13143-13147 (1996); apicidin Ia, apicidin Ib, apicidin Ic, apicidin IIa, and apicidin IIb (P. Dulski et al., PCT International Patent Publication WO 97/11366); HC-toxin, cyclic tetrapeptide (Bosch et al., Plant Cell 7: 1941-1950 (1995)); WF27082, cyclic tetrapeptide (PCT International Patent Publication WO 98/48825); and chlamydocin (Bosch et al., supra).

C. Hybrid polar compounds (HPC) based on hydroxamic acid, for example: salicyl hydroxamic acid (SBHA) (Andrews et al., International J. Parasitology 30: 761-8 (2000)); suberoylanilide hydroxamic acid (SAHA) (Richon et al., Proc. Natl. Acad. Sci. U.S.A. 95: 3003-7 (1998)); azelaic bishydroxamic acid (ABHA) (Andrews et al., supra); azelaic-1-hydroxamate-9-anilide (AAHA) (Qiu et al., Mol. Biol. Cell 11: 2069-83 (2000)); M-carboxy cinnamic acid bishydroxamide (CBHA) (Ricon et al., supra); 6-(3-chlorophenylureido) carpoic hydroxamic acid, 3-Cl-UCHA) (Richon et al., supra); MW2796 (Andrews et al., supra); and MW2996 (Andrews et al., supra).

D. Short chain fatty acid (SCFA) compounds, for example: sodium butyrate (Cousens et al., J. Biol. Chem. 254: 1716-23 (1979)); isovalerate (McBain et al., Biochem. Pharm. 53: 1357-68 (1997)); valproic acid; valerate (McBain et al., supra); 4-phenyl butyric acid (4-PBA) (Lea and Tulsyan, Anticancer RESearch 15: 879-3 (1995)); phenyl butyric acid (PB) (Wang et al., Cancer RESearch 59: 2766-99 (1999)); propinate (McBain et al., supra); butylamide (Lea and Tulsyan, supra); isobutylamide (Lea and Tulsyan, supra); phenyl acetate (Lea and Tulsyan, supra); 3-bromopropionate (Lea and Tulsyan, supra); tributyrin (Guan et al., Cancer RESearch 60: 749-55 (2000)); arginine butyrate; isobutyl amide; and valproate.

E. Benzamide derivatives, for example: MS-275 [N-(2-aminophenyl)-4-[N-(pyridine-3-yl-methoxycarbonyl)aminomethyl]benzamide] (Saito et al., Proc. Natl. Acad. Sci. U.S.A. 96: 4592-7 (1999)); and a 3'-amino derivative of MS-275 (Saito et al., supra); and CI-994.

A histone deacetylase inhibitor treatment may be carried out, for example, as follows. The concentration of the HDAC inhibitor may depend on a particular inhibitor, but is preferably 0.001 nM to about 10 mM, and more preferably about 0.01 nM to about 1000 nM. The effective amount or the dosage of a histone deacetylase inhibitor is defined as the amount of the histone deacetylase inhibitor that does not significantly decrease the survival rate of cells, specifically undifferentiated stem cells. Cells are exposed for 1 to 5 days or 1 to 3 days. The exposure period may be less than one day. In a specific embodiment, cells are cultured for about 1 to 5 days, and then exposed to an effective amount of a histone deacetylase inhibitor. However, the histone deacetylase inhibitor may be added at the start of culturing. Within such a time frame, a gene-carrying vehicle such as a vector containing a nucleic acid encoding three genes (Oct3/4, Sox2 and Klf4) is introduced into cultured cells by a known method.

E. IF Expression Vectors

Forced expression of the IFs may comprise introducing one or more mammalian expression vectors encoding an Oct 3/4, a Sox2, and a Klf4 polypeptide to a population of cells. The IFs may be introduced into the cells as exogenous genes. In some cases, the exogenous genes are integrated into the genome of a host cell and its progeny. In other cases, the exogenous genes persist in an episomal state in the host cell and its progeny. Exogenous genes are genes that are introduced to the cell from an external source. A gene as used herein is a nucleic acid that includes an open reading frame encoding a polypeptide of interest, e.g., an IF. The gene preferably includes a promoter operably linked to an open reading frame. In some cases, a natural version of the gene may already exist in the cell but an additional "exogenous gene" is added to the cell to induce polypeptide expression.

The one or more mammalian expression vectors may be introduced into greater than 20% of the total population of cells, e.g., 25%, 30%, 35%, 40%, 44%, 50%, 57%, 62%, 70%, 74%, 75%, 80%, 90%, or other percent of cells greater than 20%. A single mammalian expression vector may contain two or more of the just-mentioned IFs. In other cases, one or more expression vectors encoding an Oct 3/4, Sox2, Klf4, and c Myc polypeptide are used. In some embodiments, each of the IFs to be expressed is encoded on a separate mammalian expression vector.

In some cases, the IFs are genetically fused in frame with a transport protein amino acid sequence, e.g., that of a VP22 polypeptide as described in, e.g., U.S. Pat. Nos. 6,521,455, 6,251,398, and 6,017,735. Such VP22 sequences confer intercellular transport of VP22 fusion polypeptides from cells that have been transfected with a VP22 fusion polypeptide expression vector to neighboring cells that have not been transfected or transduced. See, e.g., Lemken et al (2007), Mol Ther, 15(2):310-319. Accordingly, the use of IF-VP22 fusion polypeptides can significantly increase the functional efficiency of transfected mammalian expression vectors in the induction methods described herein.

Examples of suitable mammalian expression vectors include, but are not limited to: recombinant viruses, nucleic acid vectors, such as plasmids, bacterial artificial chromosomes, yeast artificial chromosomes, human artificial chromosomes, cDNA, cRNA, and PCR product expression cassettes. Examples of suitable promoters for driving expression of IFs in include retroviral LTR elements; constitutive promoters such as CMV, HSV1-TK, SV40, EF-1α, β actin; PGK, and inducible promoters, such as those containing Tet-operator elements. In some cases, one or more of the mammalian expression vectors encodes, in addition to an IF, a marker gene that facilitates identification or selection of cells that have been transfected or infected. Examples of marker genes include, but are not limited to, fluorescent protein genes, e.g., for EGFP, DS-Red, YFP, and CFP; proteins conferring resistance to a selection agent, e.g., the neoR gene, and the blasticidin resistance gene.

1. Recombinant Viruses

Forced expression of an IF may be accomplished by introducing a recombinant virus carrying DNA or RNA encoding an IF to one or more cells. Additionally, the recombinant virus may carry DNA or RNA encoding more than 1 IF. This includes multiple copies of a single IF or multiple IFs contained within a single virus. For ease of reference, at times a virus will be referred to herein by the IF it is encoding. For example, a virus encoding an Oct3/4 polypeptide, may be described as an "Oct3/4 virus." In certain cases, a virus may encode more than one copy of an IF or may encode more than one IF, e.g., two IFs, at a time.

Different combinations or sets of recombinant viruses may be introduced to the cells. The set of recombinant viruses may include combinations included in any set of IFs described herein. The set of recombinant viruses may include at least: an Oct3/4 virus, a Sox2 virus, and a Klf4 virus. The set of recombinant viruses may be limited to a set of four recombinant viruses: an Oct3/4 virus, a Sox2 virus, a Klf4 virus, and a c-Myc virus. In some cases, the set of recombinant viruses is limited to a set of at least: an Oct3/4 virus, a Sox2 virus, a Klf4 virus, and a c-Myc virus. In some cases, the set of recombinant viruses is limited to Oct 3/4, Sox2, and Klf4 viruses. The set of recombinant viruses may be limited a set of at least: an Oct3/4 virus, a Sox2 virus, and a Klf4 virus. In some cases, the set of recombinant viruses includes three recombinant viruses, wherein two of the three recombinant viruses are an Oct3/4 virus and a Sox2 virus. In still other cases, the set of recombinant viruses may be limited to a Sox2 virus and a c-Myc virus.

In some cases, the set of recombinant viruses does not include a recombinant virus that encodes a polypeptide that might increase the risk of cell transformation, e.g., a c-Myc polypeptide. For example, the set of recombinant viruses can include: an Oct3/4 virus, a Sox2 virus, and a Klf4 virus but not a c-Myc virus.

In other cases, the set of recombinant viruses includes a c-Myc virus. The c-Myc polypeptide encoded by the c-Myc virus may be wild-type c-Myc or a constitutively active variant of c-Myc. In some instances, the set includes a virus encoding c-Myc polypeptide capable of inducible activity, e.g., a c-Myc-ER polypeptide, see, e.g., Littlewood, et al. (1995) Nucleic Acid Res. 23(10):1686-90.

The set of recombinant viruses may include: an Oct3/4 virus, a Sox2 virus, and a Klf4 virus, but not a TERT virus, a SV40 Large T antigen virus, HPV16 E6 virus, a HPV16 E7 virus, or a Bmi1 virus. At times, the set of recombinant viruses does not include a TERT virus. In some cases, the set of recombinant viruses does not include a SV40 virus. In other cases, the set of recombinant viruses does not include a HPV16 E6 virus or a HPV16 E7 virus.

A set of recombinant viruses may include viruses in addition to an Oct 3/4, a Sox2, and a Klf4 virus. Such additional recombinant viruses include, but are not limited to Nanog, TERT, CYP26A1, GDF3, FoxD3, Zfp42, Dnmt3b, Ecat1, and Tcl1 viruses. In some cases, the set of recombinant viruses includes any IF variant described herein.

Individual viruses may be added to the cells sequentially in time or simultaneously. In some cases, at least one virus, e.g., an Oct3/4 virus, a Sox2 virus, a Klf4 virus, or a c-Myc virus, is added to the cells at a time different from the time when one or more other viruses are added. In some examples, the Oct3/4 virus, Sox2 virus and KlF4 virus are added to the cells simultaneously, or very close in time, and the c-Myc virus is added at a time different from the time when the other viruses are added.

At least two recombinant viruses may be added to the cells simultaneously or very close in time. In some examples, Oct3/4 virus and Sox2 virus are added simultaneously, or very close in time, and the Klf4 virus or c-Myc virus is added at a different time. In some examples, Oct3/4 virus and Sox2 virus; Oct3/4 virus and Klf4 virus; Oct3/4 virus and c-Myc virus; Sox2 virus and Klf4 virus; Sox2 virus and c-Myc virus; or Klf4 and c-Myc virus are added simultaneously or very close in time.

In some cases, at least three viruses, e.g., an Oct3/4 virus, a Sox2 virus, and a Klf4 virus, are added to the cells simultaneously or very close in time. In other instances, at least four viruses, e.g., Oct3/4 virus, Sox2 virus, Klf4 virus, and c-Myc virus are added to the cells simultaneously or very close in time.

At times, the efficiency of viral infection can be improved by repetitive treatment with the same virus. In some cases, one or more Oct3/4 virus, Sox2 virus, Klf4 virus, or c-Myc virus is added to the cells at least two, at least three, or at least four separate times.

Examples of recombinant viruses include, but are not limited, to retroviruses (including lentiviruses); adenoviruses; and adeno-associated viruses. Often, the recombinant retrovirus is murine moloney leukemia virus (MMLV), but other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus, see, e.g., U.S. Pat. No. 6,333,195.

In other cases, the recombinant retrovirus is a lentivirus (e.g., Human Immunodeficiency Virus-1 (HIV-1); Simian Immunodeficiency Virus (SIV); or Feline Immunodeficiency Virus (FIV)), See, e.g., Johnston et al (1999), Journal of Virology 73(6)"4991-5000 (FIV); Nègre D et al (2002) Current Topics in Microbiology and Immunology 261:53-74 (SIV); .Naldini et al (1996) Science. 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, that aids entry into cells derived from multiple species, including cells outside of the original host species. See, e.g., id. The viral polypeptide may be a xenotropic viral polypeptide that aids entry into cells outside of the original host species. See, e.g., id. In some embodiments, the viral polypeptide is an ecotropic viral polypeptide, e.g., ecotropic env, that aids entry into cells of the original host species. See, e.g., id.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al (1994), Methods Cell Biol. Pt A:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env, lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. As packaging cells, any cells may be used that can supply a lacking protein of a recombinant virus vector plasmid deficient in at least one gene encoding a protein required for virus packaging. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al (2000) Gene Therapy 7:1063-1066; Onishi et al (1996) Experimental Hematology 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1α, β actin; retroviral LTR promoters, and inducible promoters. The retroviral construct may also comprise a packaging signal (e.g., a packaging signal derived from the MFG vector; a psi packaging signal). Examples of retroviral constructs known in the art include but are not limited to: pMX, pBabeX or derivatives thereof. See e.g., Onishi et al (1996) Experimental Hematology 24:324-329. In some cases, the retroviral construct is a self-inactivating lentiviral vector (SIN) vector, see, e.g., Miyoshi et al., (1998) J Virol. 72(10): 8150-8157. In some cases, the retroviral construct is LL-CG, LS-CG, CL-CG, CS-CG, CLG or MFG. Miyoshi et al., (1998) J Virol. 72(10): 8150-8157; Onishi et al (1996) Experimental Hematology 24:324-329; Riviere et al. (1995) PNAS 92: 6733-6737. Virus vector plasmids (or constructs), include: pMXs, pMXs-IB, pMXs-puro, pMXs-neo (pMXs-IB is a vector carrying the blasticidin-resistant gene in stead of the puromycin-resistant gene of pMXs-puro) [Experimental Hematology, 2003, 31 (11): 1007-14], MFG [Proc. Natl. Acad. Sci. U.S.A. 92, 6733-6737 (1995)], pBabePuro [Nucleic Acids Research 18, 3587-3596 (1990)], LL-CG, CL-CG, CS-CG, CLG [Journal of Virology 72: 8150-8157 (1998)] and the like as the retrovirus system, and pAdex1 [Nucleic Acids Res. 23: 3816-3821 (1995)] and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al. (1990) Nucleic Acids Research 18: 3587-3596.

The retroviral construct may encode one or more IFs. In an exemplary embodiment, pMX vectors encoding Oct3/4, Sox2, Klf4, or c-Myc polypeptides, or variants thereof, are generated or obtained. For example, Oct3/4 is inserted into pMXs-puro to create pMX-Oct3/4; Sox2 is inserted into pMXs-neo to create pMX-Sox2; Klf4 is inserted into pMXs-IB to create pMX-Klf4; and c-Myc is inserted into pMXs-IB to create pMX-c-Myc.

Methods of producing recombinant viruses from packaging cells and their uses are well-established, see, e.g., U.S. Pat. Nos. 5,834,256; 6,910,434; 5,591,624; 5,817,491; 7,070,994; and 6,995,009, incorporated herein by reference. Many methods begin with the introduction of a viral construct into a packaging cell line. The viral construct may be introduced by any method known in the art, including but not limited to: the calcium phosphate method [Kokai (Japanese Unexamined Patent Publication) No. 2-227075], the lipofection method [Proc. Natl. Acad. Sci. U.S.A. 84: 7413 (1987)], the electroporation method, microinjection, Fugene transfection, and the like, and any method described herein.

In one example, pMX-Oct3/4, pMX-Sox2, pMX-Klf4 or pMX-c-Myc is introduced into PlatE cells by Fugene HD (Roche) transfection. The cell culture medium may be replaced with fresh medium comprising FBM (Lonza) supplemented with FGM-2 Single Quots (Lonza). In some embodiments, the medium is replaced from about 12 to about 60 hours following the introduction of the viral construct, e.g., from about 12 to about 18 hours; about 18 to about 24; about 24 to about 30; about 30 to about 36; about 36 to about 42; about 42 to about 48; about 48 to about 54; or about 54 to about 60 hours following introduction of the viral construct to the producer cells. The medium may be replaced from about 24 to about 48 hours after introduction of the viral construct to the producer cells. The supernatant can be recovered from about 4 to about 24 hours following the addition of fresh media, e.g., about 4 hours. In some cases, the supernatant may be recovered about every 4 hours following the addition of fresh media. The recovered supernatant may be passed through a 0.45 uM filter (Millipore). In some cases, the recovered supernatant comprises retrovirus derived from one or more: pMX-Oct3/4, pMX-Sox2, pMX-Klf4 or pMX-c-Myc.

Adenoviral transduction may be used to force expression of the sets of IFs. Methods for generating adenoviruses and their use are well established as described in, e.g., Straus, The Adenovirus, Plenum Press (NY 1984), 451 496; Rosenfeld, et al, Science, 252:431-434 (1991); U.S. Pat. Nos. 6,203,975, 5,707,618, and 5,637,456. In other cases, adenoviral-associated viral transduction is used to force expression of the sets of IFs. Methods for preparing adeno-associated viruses and their use are well established as described in, e.g., U.S. Pat. Nos. 6,660,514 and 6,146,874.

In an exemplary embodiment, an adenoviral construct is obtained or generated, wherein the adenoviral construct, e.g., Adeno-X, comprises DNA encoding Oct3/4, Sox2, Klf4, or c-Myc. An adenoviral construct may be introduced by any method known in the art, e.g., Lipofectamine 2000 (Invitrogen) or Fugene HD (Roche), into HEK 293 cells. In some cases, the method further comprises (1) collecting the cells when they exhibit a cytopathic effect (CPE), such effect occurring from about 10 to about 20 days, e.g., about 11, 13, 14, 15, 18, or 20 days after transfection (2) subjecting the cells to from about 2 to about 5 freeze-thaw cycles, e.g., about 3, (3) collecting the resulting virus-containing liquid; (4) purifying the virus using an adenovirus purification kit (Clontech) and (5) storing the virus at −80° C. In some cases, the titer, or plaque-forming unit (PFU), of the adenoviral stocks is determined using an Adeno-X rapid titer kit (Clontech), as described herein.

The cells may be infected with a recombinant retrovirus that naturally targets a different cell type or cells originating from a different host. To aid infection efficiency, an exogenous receptor may be first introduced into the human cells. For example, an exogenous mouse receptor may be added to human cells, e.g., postnatal dermal fibroblasts, in order help entry of murine moloney leukemia virus (MMLV). The exogenous receptor may improve infection efficiency by facilitating viral entry, especially if the receptor recognizes a viral polypeptide, e.g., MMLV env, or HIV env. Examples of exogenous receptors include but are not limited to any receptor recognized by a specific retrovirus or lentivirus known in the art. For example, a murine receptor, mCAT1, GenBank Accession No NM_007513 protein is used in order to aid MMLV infection of a human target cell. In another example, a CXCR4 or CCR5 receptor is used to aid HIV-1 infection of a target cell.

The exogenous receptor may be introduced by methods described herein. Methods of introducing the exogenous receptor include but are not limited to: calcium phosphate transfection, Lipofectamine transfection, Fugene transfection, microinjection, or electroporation. In exemplary embodiments, a virus, e.g., recombinant adenovirus or retrovirus (including lentivirus), is used to introduce the exogenous receptor to the target cell. In a further exemplary embodiment, a recombinant adenovirus is used to introduce MCAT1 to human cells and then a recombinant retrovirus, e.g., MMLV, is used to introduce the IF genes, e.g., Oct 3/4, a Sox2, a Klf4, or c-Myc, to the cells.

In some cases, a solution of adenovirus comprising DNA encoding the mCAT1 protein, e.g., an adenovirus generated by using a pADEX-mCAT1 construct, is generated or obtained. The adenovirus solution can comprise Hanks' balanced salt solution. In exemplary embodiments, infection of cells is accomplished by: (1) contacting the p-ADEX-mCAT1 adenovirus solution with cells, e.g., human, non-embryonic fibroblasts, at a multiplicity of infection (m.o.i.) from about 1:5 to about 1:50, e.g., about 1:5, about 1:7; about 1:10; about 1:15, about 1:20, about 1:25; about 1:30, about 1:35; about 1:40; about 1:45, or about 1:50; (2) incubating the cells with the adenovirus solution at room temperature from about 15 minutes to about 2 hours, e.g., about 15 minutes, about 30 minutes, about 45 minutes, about 1 hour, about 1.25 hours, about 1.5 hours, about 1.75 hours, or about 2 hours; and (3) culturing the somatic cell population in culture medium from about 24 hours to about 60 hours, e.g., about 24 hours, about 30 hours, about 36 hours, about 42 hours, about 48 hours, about 54 hours, or about 60 hours.

The cells can be infected using a wide variety of methods. In some cases, the infection of cells occurs by (1) combining one or more, two or more, three or more, or all four: pMX-Oct3/4 retrovirus, pMX-Sox2 retrovirus, pMX-Klf4, or pMX-c-Myc to obtain a retrovirus solution (2) supplementing the retrovirus solution with from about 2 ug/ml to about 15 ug/ml Polybrene, e.g., about 2 ug/ml, about 3 ug/ml, about 5 ug/ml, about 7 ug/ml, about 10 ug/ml, about 12 ug/ml, or about 15 ug/ml Polybrene; (3) contacting the retroviral solution with the somatic cells, at a m.o.i. of from about 1:100 to about 1:500, e.g., about 1:100, about 1:150, about 1:200, about 1:250, about 1:300, about 1:350, about 1:400, about 1:450, or about 1:500 m.o.i.; (4) allowing the contacting of step (3) to continue at 37° C. from about 2 hours to about 24 hours, e.g., about 2 hours, about 3 hours, about 4 hours, about 5 hours, about 6 hours, about 7 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours; (5) soon after the contacting of step (4), changing the medium to MC-ES medium, as described herein; and (6) changing the MC-ES medium with fresh medium every 1 to 2 days. In some cases, infection of somatic cells occurs by following steps (1) through (6) described herein, with the added step of pre-incubating the somatic cells for a length of time, e.g., about 48 hours, prior to contacting the cells with the retroviral solution. Such pre-incubation may be necessary when the somatic cell expresses an exogenous receptor that was introduced by viral transduction, transfection, or other method. Thus, in some embodiments, if an adenovirus or lentivirus is used to introduce an exogenous receptor, e.g., mCAT1, to the somatic cell; such cells may need to be cultured for a length of time from at least about 30 hours to at least about 60 hours, e.g., about 30, about 35, about 40, about 48, about 52, about 55, or about 60 hours.

The infection of cells may be accomplished by any method known in the art. e.g., Palsson, B., et al. WO95/10619. Apr. 20, 1995; Morling, F. J. et al. (1995). Gene Therapy. 2: 504-508; Gopp et al. (2006) Methods Enzymol. 420:64-81. For example, the infection may be accomplished by spin-infection or "spinoculation" methods that involve subjecting the cells to centrifugation during the period closely following the addition of virus to the cells. In some cases, virus may be concentrated prior to the infection, e.g., by ultracentrifugation. In some cases, other technologies may be used to aid or improve entry of retroviruses into the target cell. For example, the retrovirus may be contacted with a liposome or immuno-liposome to aid or direct entry into a specific cell type. See, e.g., Tan et al. (2007) Mol Med. 13(3-4): 216-226.

The methods of infecting cells described herein may be used to infect cells expressing an exogenous receptor, e.g., MCAT1 or other exogenous receptor described herein. Depending on how the exogenous receptor was introduced, the preincubation period of the cells prior to infection may need to be varied. In some cases, cells that do not express an exogenous receptor are used. Some recombinant retroviruses, e.g., VSV-G pseudotyped recombinant retroviruses, may not need the aid of an exogenous receptor in order to efficiently enter cells. In some examples, VSV-G pseudotyped recombinant retrovirus is introduced to cells following the method described herein, except that the timing of the preculturing of the cells may vary.

2. Nucleic Acid Vectors

Nucleic acid vector transfection (e.g., transient transfection) methods may be used to introduce IFs into human cells. Methods for preparation of transfection-grade nucleic acid expression vectors are well established. See, e.g., Sambrook and Russell (2001), "Molecular Cloning: A Laboratory Manual," 3rd ed, (CSHL Press). Examples of high efficiency transfection efficiency methods include "nucleofection," as described in, e.g., Trompeter (2003), J Immunol Methods, 274(1-2):245-256, and in international patent application publications WO2002086134, WO200200871, and WO2002086129, transfection with lipid-based transfection reagents such as Fugene® 6 and Fugene® HD (Roche), DOTAP, and Lipofectamine™ LTX in combination with the PLUS™ (Invitrogen, Carlsbad, Calif.), Dreamfect™ (OZ Biosciences, Marseille, France), GeneJuice™ (Novagen, Madison, Wis.), polyethylenimine (see, e.g., Lungwitz et al (2005), Eur J Pharm Biopharm, 60(2):247-266), and Gene-Jammer™ (Stratagene, La Jolla, Calif.), and nanoparticle transfection reagents as described in, e.g., U.S. patent application Ser. No. 11/195,066.

3. Protein Transduction

The induction methods may use protein transduction to introduce at least one of the IFs directly into cells. In some cases, protein transduction method includes contacting cells with a composition containing a carrier agent and at least one purified polypeptide comprising the amino acid sequence of one of the above-mentioned IFs. Examples of suitable carrier agents and methods for their use include, but are not limited to, commercially available reagents such as Chariot™ (Active Motif, Inc., Carlsbad, Calif.) described in U.S. Pat. No. 6,841,535; Bioport® (Gene Therapy Systems, Inc., San Diego, Calif.), GenomeONE (Cosmo Bio Co., Ltd., Tokyo, Japan), and ProteoJuice™ (Novagen, Madison, Wis.), or nanoparticle protein transduction reagents as described in, e.g., in U.S. patent application Ser. No. 11/138,593.

The protein transduction method may comprise contacting a cells with at least one purified polypeptide comprising the amino acid sequence of one of the above-mentioned TAs fused to a protein transduction domain (PTD) sequence (IF-PTD fusion polypeptide). The PTD domain may be fused to the amino terminal of an IF sequence; or, the PTD domain may be fused to the carboxy terminal of an IF sequence. In some cases, the IF-PTD fusion polypeptide is added to cells as a denatured polypeptide, which may facilitate its transport into cells where it is then renatured. Generation of PTD fusion proteins and methods for their use are established in the art as described in, e.g., U.S. Pat. Nos. 5,674,980, 5,652,122, and 6,881,825. See also, Becker-Hapak et al (2003), Curr Protocols in Cell Biol, John Wiley & Sons, Inc. Exemplary PTD domain amino acid sequences include, but are not limited to, any of the following:

```
YGRKKRRQRRR;        (SEQ ID NO: 1)

RKKRRQRR;           (SEQ ID NO: 2)

YARAAARQARA;        (SEQ ID NO: 3)

THRLPRRRRR;         (SEQ ID NO: 4)
and

GGRRARRRRRR.        (SEQ ID NO: 5)
```

In some cases, individual purified IF polypeptides are added to cells sequentially at different times. In other embodiments, a set of at least three purified IF polypeptides, but not a purified c-Myc polypeptide, e.g., an Oct3/4 polypeptide, a Sox2 polypeptide, and a Klf4 polypeptide are added to cells. In some embodiments, a set of four purified IF polypeptides, e.g., purified Oct3/4, Sox2, Klf4, and c-Myc polypeptides are added to cells. In some embodiments, the purified IF polypeptides are added to cells as one composition (i.e., a composition containing a mixture of the IF polypeptides). In some embodiments, cells are incubated in the presence of a purified IF polypeptide for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. In some embodiments, protein transduction of cells is repeated with a frequency of about every day to about every 4 days, e.g., every 1.5 days, every 2 days, every 3 days, or any other frequency from about every day to about every four days Forced expression of IFs may also be achieved by using nucleic acid-free IF-containing protein transducing nanoparticles (PTN). Details of methods for generating and using PTNs are found in, e.g., Link et al (2006), *Nuc Acids Res*, 34(2):e16.

In some cases, the methods described herein utilize protein transduction and expression vector transduction/transfection in any combination to force expression of a set of IFs as described herein. In some embodiments, retroviral expression vectors are used to force expression of Oct 3/4, a Sox2, and a Klf4 polypeptides in cells, and purified c-Myc purified polypeptide is introduced into cells by protein transduction as described herein. HDAC inhibitor treatment can be used in addition to the purified IF polypeptide. In some cases, a set of at least three purified IF polypeptides, but not a purified c-Myc polypeptide, e.g., an Oct3/4 polypeptide, a Sox2 polypeptide, and a Klf4 polypeptide are added to cells which are also subjected to HDAC inhibitor treatment.

F. Subcloning Induced Cell Colonies

Cell colonies may be subcloned by any method known in the art. In some cases, the iPSCs are cultured and observed for about 14 days to about 40 days, e.g., 15, 16, 17, 18, 19, 20, 23, 24, 27, 28, 29, 30, 31, 33, 34, 35, 36, 37, 38 days, or any other period from about 14 days to about 40 days prior to identifying and selecting clones comprising "iPSCs" based on morphological characteristics. Morphological characteristics for identifying iPSC clones include, but are not limited to, a small cell size with a high nucleus-to-cytoplasm ratio; formation of small monolayer colonies within the space between parental cells (e.g., between fibroblasts).

After washing cell cultures with a physiological buffer, e.g., Hank's balanced salt solution, colonies displaying the morphological characteristics of interest are surrounded by a cloning ring to the bottom of which silicone grease has been applied. About 100 μl (or 50 μl to 150 μl) of "Detachment Medium For Primate ES Cells" (manufactured by Repro-CELL, Tokyo Japan) is then added to the cloning ring and incubated at 37° C. for about 20 minutes to form a cell suspension. The cell suspension in the ring containing the detached colonies is then added to about 2 ml of MC ES medium (or other medium described herein), and plated in one well of a MEF-coated 24-well plate or other cell culture vessel of equivalent surface area. After culturing the colony-derived cells in a 5% $CO_2$ cell culture incubator at 37° C. for about 14 hours, the medium is replaced. Subsequently, the medium is replaced about every two days until about 8 days later when a second subculture is carried out.

In some embodiments, in the first subculture, the medium is removed, the cells are washed with Hank's balanced salt solution, and Detachment Medium For Primate ES Cells (ReproCell, Tokyo, Japan) is then added to the cells and incubated at 37° C. for 10 minutes. After the incubation, MC-ES medium (2 ml) is added to the resulting cell suspension to quench the activity of the Detachment Medium. The cell suspension is then transferred to a centrifuge tube, and centrifuged at 200×g at 4° C. for 5 minutes. The supernatant is removed, the cell pellet is resuspended in MC ES medium, and the resuspended cells are plated on four wells of a MEF-coated 24-well plate and cultured for about seven days until a second subculture is prepared.

In the second subculture, prepared by the method described above, cells are plated on a 60 mm cell culture dish coated with matrigel at a concentration of 20 μg/cm$^2$. About eight days later (approximately 5 weeks after initiating forced expression of IFs), a third subculture is prepared in which cells are plated on two matrigel-coated 60 mm cell culture dishes, one of which can subsequently be used for gene expression analysis and the other for continued passaging as described below. One of the subcultures is used for gene expression analysis, as described herein, and the other is passaged as needed to maintain a cell line derived from the iPSC clone.

G. Passaging and Maintaining Induced Cells

After subcloning, the iPSCs may be subcultured about every 5 to 7 days. In some cases, the cells are washed with Hank's balanced salt solution, and dispase or Detachment Medium For Primate ES Cells is added, and incubated at 37° C. for 5 to 10 minutes. When approximately more than half of the colonies are detached, MC-ES medium is added to quench enzymatic activity of the detachment medium, and the resulting cell/colony suspension is transferred to a centrifuge tube. Colonies in the suspension are allowed to settle on the bottom of the tube, the supernatant is carefully removed, and MC-ES medium is then added to resuspend the colonies. After examining the size of the colonies, any extremely large ones are broken up into smaller sizes by slow up and down pipetting. Appropriately sized colonies are plated on a matrigel-coated plastic culture dish with a base area of about 3 to 6 times that before subculture.

Examples of culture media useful for culturing human pluripotent stem cells induced from undifferentiated stem cells present in a human postnatal tissue of the present invention include, but are not limited to, the ES medium, and a culture medium suitable for culturing human ES cells such as MEF-conditioned ES medium (MC-ES) or other medium described herein, e.g., mTeSR™. In some examples, the cells are maintained in the presence of a ROCK inhibitor, as described herein.

IV. Analysis of Induced Cells

Cell colonies subcultured from those initially identified on the basis of morphological characteristics may be assayed for any of a number of properties associated with pluripotent stem cells, including, but not limited to, expression of alkaline phosphatase activity, expression of ES cell marker genes, expression of protein markers, hypomethylation of Oct3/4 and Nanog promoters relative to a parental cells, long term self-renewal, normal diploid karyotype, and the ability to form a teratoma comprising ectodermal, mesodermal, and endodermal tissues.

A number of assays and reagents for detecting alkaline phosphatase activity in cells (e.g., in fixed cells or in living cells) are known in the art. In an exemplary embodiment, colonies to be analyzed are fixed with a 10% formalin neutral buffer solution at room temperature for about 5 minutes, e.g., for 2 to 5 minutes, and then washed with PBS. A chromogenic substrate of alkaline phosphatase, 1 step BCIP (5-Bromo-4-Chloro-3'-Indolyphosphate p-Toluidine Salt) and NBT (Nitro-Blue Tetrazolium Chloride) manufactured by Pierce (Rockford, Ill.) is then added and reacted at room temperature for 20 to 30 minutes. Cells having alkaline phosphatase activity are stained blue-violet.

Putative iPS cell colonies tested for alkaline phosphatase activity may be then assayed for expression of a series of human embryonic stem cell marker (ESCM) genes including, but not limited to, Nanog, TDGF1, Dnmt3b, Zfp42, FoxD3, GDF3, CYP26A1, TERT, Oct 3/4, Sox2, Sal14, and HPRT. See, e.g., Assou et al (2007), Stem Cells, 25:961-973. Many methods for gene expression analysis are known in the art. See, e.g., Lorkowski et al (2003), Analysing Gene Expression, A Handbook of Methods: Possibilities and Pitfalls, Wiley-VCH. Examples of suitable nucleic acid-based gene expression assays include, but are not limited to, quantitative RT-PCR (qRT-PCR), microarray hybridization, dot blotting, RNA blotting, RNAse protection, and SAGE.

In some embodiments, levels of ESCM gene mRNA expression levels in putative iPS cell colonies are determined by qRT-PCR. Putative iPS cell colonies are harvested, and total RNA is extracted using the "Recoverall total nucleic acid isolation kit for formaldehyde- or paraformaldehyde-fixed, paraffin-embedded (FFPE) tissues" (manufactured by Ambion, Austin, Tex.). In some instances, the colonies used for RNA extraction are fixed colonies, e.g., colonies that have been tested for alkaline phosphatase activity. The colonies can be used directly for RNA extraction, i.e., without prior fixation. In an exemplary embodiment, after synthesizing cDNA from the extracted RNA, the target gene is amplified using the TaqMan® PreAmp mastermix (manufactured by Applied Biosystems, Foster City, Calif.). Real-time quantitative PCR is performed using an ABI Prism 7900HT using the following PCR primer sets (from Applied Biosystems) for detecting mRNA of the above-mentioned ESCM genes: Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1).

Putative iPS cell colonies may be assayed by an immunocytochemistry method for expression of protein markers including, but not limited to, SSEA-3, SSEA-4, TRA-1-60, TRA-1-81, CD9, CD24, Thy-1, and Nanog. A wide range of immunocytochemistry assays, e.g., fluorescence immunocytochemistry assays, are known as described in, e.g., Harlow et al (1988), Antibodies: A Laboratory Manual, Cold Spring Harbor Laboratory, Cold Spring Harbor, N.Y., 353-355, and see also, The Handbook—A Guide to Fluorescent Probes and Labeling Technologies, Molecular Probes, Inc., Eugene, Oreg., (2004).

In an exemplary embodiment, expression of one or more of the above-mentioned protein markers in putative iPS cell colonies is assayed as follows. Cultured cells are fixed with 10% formaldehyde for 10 min and blocked with 0.1% gelatin/PBS at room temperature for about an hour. The cells are incubated overnight at 4° C. with primary antibodies against SSEA-3 (MC-631; Chemicon), SSEA-4 (MC813-70; Chemicon), TRA-1-60 (ab16288; abcam), TRA-1-81 (ab16289; abcam), CD9 (M-L13; R&D systems), CD24 (ALB9; abcam), Thy1 (5E10; BD Bioscience), or Nanog (MAB1997; R&D Systems). For Nanog staining, cells are permeabilized with 0.1% Triton X-100/PBS before blocking. The cell colonies are washed with PBS three times, then incubated with AlexaFluor 488-conjugated secondary antibodies (Molecular Probes) and Hoechst 33258 (Nacalai) at room temperature for 1 h. After further washing, fluorescence is detected with a fluorescence microscope, e.g., Axiovert 200M microscope (Carl Zeiss).

Expression of embryonic stem cell (ESC) marker genes in iPSC colonies may be assayed in live cells, which increases the efficiency of identifying iPSC colonies following an induction method as described herein. Examples of ESC marker genes useful for identifying induced stem cell colonies include, e.g., Oct3/4, Nanog, Klf4, Lin28, Sox2, c-Myc, or TERT. In some embodiments, mRNA for one or more of these genes is detected in live cells. In other embodiments, mRNAs for two or more of the ESC marker genes is detected. In one approach, cells are contacted with one or more molecular beacon probes that hybridize to and signal the presence of one or more stem cell marker genes. Molecular beacons (MBs) are single-stranded oligonucleotide hybridization probes that form a stem-and-loop structure. The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. MBs do not fluoresce when they are free in solution. However, when they hybridize to a target sequence they undergo a conformational change that enables them to fluoresce brightly. The probe sequence may range in length from about 15 to about 30 nucleotides depending on the GC content of the target probe sequence. Generally, the GC content of the target probe sequence should be from about 40 to about 60%. The flanking stem sequences may range from about 5 to about 7 nucleotides with a GC content of about 75 to about 100 percent. The design of MBs and their use to detect mRNA expression in living cells is known in the art, as described in, e.g., Rhee et al (2008), *Nuc Acid Res,* 36(5):e30. Useful algorithms for determining melting temperatures of an MB duplex and an MB/target duplex are known in the art. See, e.g., the "Mfold" algorithm described in Zucker (2003), *Nuc Acids Res* 31(13): 3406-3415, which is public available on a web server: frontend.bioinfo.rpi.edu/applications/mfold/cgi-bin/dna-form1.cgi. See also the Hyther Server at: ozone3.chem.wayne.edu/. Typical parameters for use in these algorithms are 200 nM concentration for beacons and nucleic acid target, a folding temperature of 37° C., and ionic condition of 10 mM KCl and 5 mM MgCl2. The iPSC colonies to be evaluated may be contacted about 14 days to about 50 days after initiating induction, e.g., 14 days to 21 days, 14 days to 28 days, 20 days to 45 days, 25 days to 40 days, 30 days to 35 days, 30 days to 50 days after induction. Preferably, cells are contacted with as low a concentration of an MB and as short a period as compatible with reliably detecting a signal. In some embodiments, the concentration of an MB of about 0.1 μM to about 5 μM (for each MB), e.g., 0.1 μM to 0.5 μM, 0.2 μM to 1 μM, 0.5 μM to 2 μM, or 3 μM to 5 μM. Incubation periods with a MB may range from about 5 minutes to about two hours, e.g., 15 minutes to 30 minutes, 20 minutes to one hour, 30 minutes to 1.5 hours, 45 minutes to 2 hours, or any other time period form about 5 minutes to two hours. In some cases, MBs are introduced into the cells without the use of a transfection reagent. In other cases, a transfection reagent optimized for oligonucleotide transfection is utilized, e.g., TransIT® oligo transfection reagent kit or any other transfection reagents known in the art. In other cases, streptolysin-O is used to transiently permealize cells to allow entry of the MBs into the cells. This method is described in, e.g., Rhee et al supra and Santangelo et al (2004), *Nuc Acids Res,* 32(6): e57.

In some cases, MBs are added to adherent cell cultures and cell colonies found to be positive for expression of one or more ESC marker genes are picked off the substrate as described above. In other cases, MBs are added to iPSCs in suspension and ESC-positive cells are selected by FACS or any other fluorescence based sorting method. Alternatively, MBs are added to adherent iPSCs, which are then dispersed prior to FACS selection. Use of FACS for selection of iPSCs is particularly useful for high throughput generation of iPSC lines and panels of iPSC lines.

A. Methylation Analysis

In some embodiments, a characteristic of the iPSCs is reduced methylation of the genomic promoters of Oct3/4 and Nanog relative to those of their parental cells. Suitable Oct3/4 promoter regions to be analyzed include, but are not limited to, the Oct3/4 proximal promoter including conserved region 1 (CR1) and the Oct3/4 promoter distal enhancer including CR4. Suitable Nanog promoter regions to be analyzed include, but are not limited to, the Nanog proximal promoter including the Oct3/4 and Sox2 binding sites. See, e.g., Rodda et al (2005), J Biol Chem, 280:24731-24737 and Yang et al (2005), J Cell Biochem, 96:821-830. A number of methods for the quantitative analysis of genomic DNA are known as described in, e.g., Brena et al (2006), J Mol Med, 84(5):365-377. In an exemplary embodiment, genomic DNA isolated from putative iPSCs and cells used for a comparison is isolated and treated with bisulfite. Bisulfite-treated genomic DNA is then PCR-amplified with primers containing a T7 promoter sequence. Afterwards, RNA transcripts are generated using T7 polymerase and then treated with RNAse A to generate methylation-specific cleavage products. Methylation of individual CpG sites is assessed by MALDI-TOF mass spectrometry of the cleavage products. A detailed description of the method is provided in, e.g., Ehich et al (2005), Proc Natl Acad Sci USA, 102: 15785-15790.

B. Self-Renewal Assay

One of the characteristics of stem cells is their ability to proliferate continuously without undergoing senescence. Accordingly, iPSCs are assessed for their ability to be passaged continuously in vitro. In some cases, the iPSCs are assayed for their ability to be passaged for at least about 30 to at least about 100 times in vitro, e.g., about 33, 35, 40, 45, 51, 56, 60, 68, 75, 80, 90, 93, 100, or any other number of passages from at least about 30 to at least about 100 passages.

In another evaluation, iPSCs are assayed for their ability to proliferate for a period of about 30 days to about 500 days from initiation of forced expression of IFs in parental cells, e.g., 40 days, 50 days, 60 days, 70 days, 80 days, 100 days, 150 days, 180 days, 200 days, 250 days, 300 days, 400 days, 450 days or any other period from about 30 days to about 500 days from initiation of forced expression of IFs in the parental cells. In some embodiments, long-term self-renewal of iPSCs is determined when the cells are passaged in a defined medium (e.g., mTeSR1 medium) and in the absence of feeder cells, e.g., mTeSR1 medium as described herein. In other embodiments, cells are passaged in MC-ES medium as described herein.

C. Karyotype Analysis

As another possible analysis, iPSCs are assessed for diploidy and a normal, stable karyotype, e.g., stable after the cells of have been passaged for at least one year in vitro. A number of karotype analysis methods are known in the art. In some embodiments, the karyotype analysis method is multicolor FISH as described in, e.g., Bayani et al (2004), Curr Protoc Cell Biol, Chapter 22:Unit 22.5. In other embodiments, the karyotype analysis includes a molecular karyotype analysis as described in, e.g., Vermeesch et al (2007), Eur J Hum Genet, 15(11):1105-1114. In an exemplary embodiment, iPSCs are pretreated with 0.02 µg/ml colecemid for about 2 to about 3 hours, incubated with about 0.06 to about 0.075M KCl for about 20 minutes, and then fixed with Carnoy's fixative. Afterwards, for multicolor FISH analysis, cells are hybridized with multicolor FISH probes, e.g., those in the Star*FISH© Human Multicolour FISH (M-FISH) Kit from Cambio, Ltd (Cambridge, UK).

D. Teratoma Analysis

It is generally believed that pluripotent stem cells have the ability to form a teratoma, comprising ectodermal, mesodermal, and endodermal tissues, when injected into an immunocompromised animal. Induced cells or induced pluripotent stem cells (iPS) or ES cell-like pluripotent stem cells may refer to cells having an in vitro long-term self-renewal ability and the pluripotency of differentiating into three germ layers, and said pluripotent stem cells may form a teratoma when transplanted into a test animal such as mouse.

The iPSCs may be assessed for pluripotency in a teratoma formation assay in an immunocompromised animal model. The immunocompromised animal may be a rodent that is administered an immunosuppressive agent, e.g., cyclosporin or FK-506. For example, the immunocompromised animal model may be a SCID mouse. About $0.5 \times 10^6$ to about $2.0 \times 10^6$, e.g., $0.6 \times 10^6$, $0.8 \times 10^6$, $1.0 \times 10^6$, $1.2 \times 10^6$, $1.5 \times 10^6$, $1.7 \times 10^6$, or other number of iPSCs from about $0.5 \times 10^6$ to about $2.0 \times 10^6$ iPSCs/mouse may be injected into the medulla of a testis of a 7- to 8-week-old immunocompromised animal. After about 6 to about 8 weeks, the teratomas are excised after perfusing the animal with PBS followed by 10% buffered formalin. The excised teratomas are then subjected to immunohistological analysis. One method of distinguishing human teratoma tissue from host (e.g., rodent) tissue includes immunostaining for the human-specific nuclear marker HuNu. Immunohistological analysis includes determining the presence of ectodermal (e.g., neuroectodermal), mesodermal, and endodermal tissues. Protein markers for ectodermal tissue include, but are not limited to, nestin, GFAP, and integrin β1. Protein markers for mesodermal tissue include, but are not limited to, collagen II, Brachyury, and osteocalcin. Protein markers for endodermal tissue include, but are not limited to, α-fetoprotein (αFP) and HNF3beta.

E. Global Gene Expression

In some embodiments, global gene expression analysis is performed on putative iPS cell colonies. Such global gene expression analysis may include a comparison of gene expression profiles from a putative iPS cell colony with those of one or more cell types, including but not limited to, (i) parental cells, i.e., one or more cells from which the putative iPS cell colony was induced; (ii) a human ES cell line; or (iii) an established iPS cell line. As known in the art, gene expression data for human ES cell lines are available through public sources, e.g., on the world wide web in the NCBI "Gene Expression Omnibus" database. See, e.g., Barrett et al (2007), Nuc Acids Res, D760-D765. Thus, in some embodiments, comparison of gene expression profiles from a putative iPS colony to those of an ES cell line entails comparison experimentally obtained data from a putative iPS cell colony with gene expression data available through public databases. Examples of human ES cell lines for which gene expression data are publicly available include, but are not limited to, hE14 (GEO data set accession numbers GSM151739 and GSM151741), Sheff4 (GEO Accession Nos GSM194307, GSM194308, and GSM193409), h_ES 01 (GEO Accession No. GSM194390), h_ES H9 (GEO Accession No. GSM194392), and h_ES BG03 (GEO Accession No. GSM194391).

It is also possible to accomplish global gene expression by analyzing the total RNA isolated from one or more iPS cell lines by a nucleic acid microarray hybridization assay. Examples of suitable microarray platforms for global gene expression analysis include, but are not limited to, the Human Genome U133 plus 2.0 microarray (Affymetrix) and the Whole Human Genome Oligo Micoarray (Agilent). A number of analytical methods for comparison of gene expression profiles are known as described in, e.g., Suarez-Farinas et al (2007), Methods Mol Biol, 377:139-152, Hardin et al (2007), BMC Bioinformatics, 8:220, Troyanskaya et al (2002), Bioinformatics, 18(11):1454-1461, and Knudsen (2002), A Biologist's Guide to Analysis of DNA Microarray Data, John Wiley & Sons. In some embodiments, gene expression data from cells produced by the methods described herein are compared to those obtained from other cell types including, but not limited to, human ES cell lines, parental cells, and multipotent stem cell lines. Suitable statistical analytical metrics and methods include, but are not limited to, the Pearson Correlation, Euclidean Distance, Hierarchical Clustering (See, e.g., Eisen et al (1998), Proc Natl Acad Sci USA, 95(25): 14863-14868), and Self Organizing Maps (See, e.g., Tamayo et al (1999), Proc Natl Acad Sci USA, 96(6):2907-2912.

F. Methods for Differentiating Induced Stem Cell Lines iPSC lines may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the iPSCs may be terminally differentiated cells, or they may be capable of giving rise to cells of a specific lineage. For example, iPSCs can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes. Methods for differentiating iPSCs are further disclosed in U.S. application Ser. No. 12/157,967; filed Jun. 13, 2008; first inventor Kazuhiro Sakurada, 61/061,594; filed on Jun. 13, 2008; First Inventor Kazuhiro Sakurada, and 61/061,565; filed on Jun. 13, 2008; First Inventor Kazuhiro Sakurada, which are hereby incorporated by reference in their entirety.

There are numerous methods of differentiating the iPSCs into a more specialized cell type. Methods of differentiating iPSCs may be similar to those used to differentiate other stem cells, particularly ES cells, MSCs, MAPCs, MIAMI, hematopoietic stem cells (HSCs). In some cases, the differentiation occurs ex vivo; in some cases the differentiation occurs in vivo.

Any known method of generating neural stem cells from ES cells may be used to generate neural stem cells from iPSCs, See, e.g., Reubinoff et al. (2001) Nat Biotechnol. 19(12):1134-40. For example, neural stem cells may be generated by culturing the iPSCs as floating aggregates in the presence of noggin, or other bone morphogenetic protein antagonist, see e.g., Itsykson et al. (2005) Mol Cell Neurosci. 30(1):24-36. In another example, neural stem cells may be generated by culturing the iPSCs in suspension to form aggregates in the presence of growth factors, e.g., FGF-2, Zhang et al. (2001), Nat. Biotech. (19) 1129-1133. In some cases, the aggregates are cultured in serum-free medium containing FGF-2. In another example, the iPSCs are co-cultured with a mouse stromal cell line, e.g., PA6 in the presence of serum-free medium comprising FGF-2. In yet another example, the iPSCs are directly transferred to serum-free medium containing FGF-2 to directly induce differentiation.

Neural stems derived from the iPSCs may be differentiated into neurons, oligodendrocytes, or astrocytes. Dopaminergic neurons play a central role in Parkinson's Disease and are thus of particular interest. In order to promote differentiation into dopaminergic neurons, iPSCs may be co-cultured with a PA6 mouse stromal cell line under serum-free conditions, see, e.g., Kawasaki et al. (2000) Neuron 28(1):31-40. Other methods have also been described, see, e.g., Pomp et al. (2005), Stem Cells 23(7):923-30; U.S. Pat. No. 6,395,546.

Oligodendrocytes may also be generated from the iPSCs. For example, oligodendrocytes may be generated by co-culturing iPSCs or neural stem cells with stromal cells, e.g., Lee et al. (2000) Nature Biotechnol 18:675-679. In another example, oligodendrocytes may be generated by culturing the iPSCs or neural stem cells in the presence of a fusion protein, in which the Interleukin (IL)-6 receptor, or derivative, is linked to the IL-6 cyotkine, or derivative thereof.

Astrocytes may also be produced from the iPSCs. Astrocytes may be generated by culturing iPSCs or neural stem cells in the presence of neurogenic medium with bFGF and EGF, see e.g., Brustle et al. (1999) Science 285:754-756.

Induced cells may be differentiated into pancreatic beta cells by methods known in the art, e.g., Lumelsky et al. (2001) Science 292:1389-1394; Assady et al., (2001) Diabetes 50:1691-1697; D'Amour et al (2006) Nat Biotechnol:1392-1401' D'Amouret al. (2005) Nat Biotechnol 23:1534-1541. The method may comprise culturing the iPSCs in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al. (2007) Cell Res 4:333-444. In other examples, the method comprises culturing the iPSCs in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, 4 days; followed by culturing in the presence of 2% FBS, FGF-10, and KAAD-cyclopamine (keto-N-aminoethylaminocaproyl dihydro cinnamoylcyclopamine and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the iPSCs. For example, culturing the iPSCs in the presence of sodium butyrate may generate hepatocytes, see e.g., Rambhatla et al. (2003) Cell Transplant 12:1-11. In another example, hepatocytes may be produced by culturing the iPSCs in serum-free medium in the presence of Activin A, followed by culturing the cells in fibroblast growth factor-4 and bone morphogenetic protein-2, e.g., Cai et al. (2007) Hepatology 45(5):1229-39. In an exemplary embodiment, the iPSCs are differentiated into hepatic cells or hepatic stem cells by culturing the iPSCs in the presence of Activin A from about 2 to about 6 days, e.g., about 2, about 3, about 4, about 5, or about 6 days, and then culturing the iPSCs in the presence of hepatocyte growth factor (HGF) for from about 5 days to about 10 days, e.g., about 5, about 6, about 7, about 8, about 9, or about 10 days.

The method may also comprise differentiating iPSCs into cardiac muscle cells. In an exemplary embodiment, the method comprises culturing the iPSCs in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the iPSCs may in the presence of LIF, or by subjecting them to other methods in the art to generate cardiomyocytes from ES cells, e.g., Bader et al. (2000) Circ Res 86:787-794, Kehat et al. (2001) J Clin Invest 108:407-414;; Mummery et al. (2003) Circulation 107:2733-2740.

Examples of methods to generate other cell-types from iPSCs include: (1) culturing iPSCs in the presence of retinoic acid, leukemia inhibitory factor (LIF), thyroid hormone (T3), and insulin in order to generate adipoctyes, e.g., Dani et al.

(1997) J. Cell Sci 110:1279-1285; (2) culturing iPSCs in the presence of BMP-2 or BMP-4 to generate chondrocytes, e.g., Kramer et al. (2000) Mech Dev 92:193-205; (3) culturing the iPSCs under conditions to generate smooth muscle, e.g., Yamashita et al. (2000) Nature 408: 92-96; (4) culturing the iPSCs in the presence of beta-mercaptoethanol to generate keratinocytes, e.g., Bagutti et al. (1996) Dev Biol 179: 184-196; Green et al. (2003) Proc Natl Acad Sci USA 100: 15625-15630; (5) culturing the iPSCs in the presence of Interleukin-3 (IL-3) and macrophage colony stimulating factor to generate macrophages, e.g., Lieschke and Dunn (1995) Exp Hemat 23:328-334; (6) culturing the iPSCs in the presence of IL-3 and stem cell factor to generate mast cells, e.g., Tsai et al. (2000) Proc Natl Acad Sci USA 97:9186-9190; (7) culturing the iPSCs in the presence of dexamethasone and stromal cell layer, steel factor to generate melanocytes, e.g., Yamane et al. (1999) Dev Dyn 216:450-458; (8) co-culturing the iPSCs with fetal mouse osteoblasts in the presence of dexamethasone, retinoic acid, ascorbic acid, beta-glycerophosphate to generate osteoblasts, e.g., Buttery et al. (2001) Tissue Eng 7:89-99; (9) culturing the iPSCs in the presence of osteogenic factors to generate osteoblasts, e.g., Sottile et al. (2003) Cloning Stem Cells 5:149-155; (10) overexpressing insulin-like growth factor-2 in the iPSCs and culturing the cells in the presence of dimethyl sulfoxide to generate skeletal muscle cells, e.g., Prelle et al. (2000) Biochem Biophys Res Commun 277:631-638; (11) subjecting the iPSCs to conditions for generating white blood cells, e.g., Rathjen et al. (1998) Reprod Fertil Dev 10:31-47; or (12) culturing the iPSCs in the presence of BMP4 and one or more: SCF, FLT3, IL-3, IL-6, and GCSF to generate hematopoietic progenitor cells, e.g., Chadwick et al. (2003) Blood 102:906-915.

In some cases, sub-populations of differentiated cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

In a specific embodiment, the hygromycin B phosphotransferase-EGFP fusion protein is expressed in a cell type specific manner. The method of purifying comprises sorting the cells to select green fluorescent cells and reiterating the sorting as necessary, in order to obtain a population of cells enriched for cells expressing the construct (e.g., hygromycin B phosphotransferase-EGFP) in a cell-type-dependent manner. Selection of desired sub-populations of cells may also be accomplished by negative selection of proliferating cells with the herpes simplex virus thymidine kinase/ganciclovir (HS-Vtk/GCV) suicide gene system or by positive selection of cells expressing a bicistronic reporter, e.g., Anderson et al. (2007) Mol Ther. (11):2027-2036.

G. Panels of Induced Stem Cell Lines

In some cases, the methods described herein utilize a panel of iPSC lines or a panel of cells differentiated from iPSC lines. A panel of iPSC lines comprises multiple iPSC lines, e.g., iPSC lines, that meet certain selection criteria. Also provided herein are panels of cells differentiated from iPSC lines as described herein. Such panels of differentiated cells include, but are not limited to, panels of neural stem cells, neurons, retinal cells, glial progenitor cells, glial cells, cardiac progenitor cells, cardiomyocytes, pancreatic progenitor cells, pancreatic beta cells, hepatic stem cells, hepatocytes or lung progenitor cells. In some cases, the selection criteria for inclusion of an iPSC line in a panel of iPSC lines are determined prior to generating the iPSC lines that will constitute the panel. In other cases, the selection criteria are applied to iPSC lines generated before hand, e.g., a bank of iPSC lines. Selection criteria include, but are not limited to, the presence or absence of a particular health condition in an iPSC donor, a positive drug response in an iPSC donor, negative, positive, or adverse drug responses in an iPSC donor, the presence or absence of a particular phenotype in an iPSC line or in cells differentiated from the iPSC line, and the presence or absence of one or more polymorphic alleles in the cell lines or their corresponding donors.

In some embodiments, where selection criteria include the presence or absence of one or more polymorphic alleles, the panel includes genetically diverse human iPSC lines in which each iPSC line carries at least one polymorphic allele that is unique among the iPSCs to be included in the panel, e.g., 5 to 10, 20 to 50, 50 to 200, 200 to 500, 500 to 1000, 1000 to 5000, 5000 to 20000, or 20000 to 50000 polymorphic alleles that are unique within the panel of iPSC lines. Such polymorphic alleles may include, e.g., a SNP allele, a promoter allele, or a protein-encoding allele. Polymorphic alles can be screened and scored for by genotyping using any of a number of known genotyping assays. In some cases, the genotyping assay is a multiplexed genotyping assay, e.g., a nucleic acid microarray assay platform such as a "SNP chip." In some cases, the one or more polymorphic alleles are pre-selected. In some embodiments, the one or more preselected alleles are polymorphic alleles associated with a health condition or a predisposition to a health condition. Examples of polymorphic alleles associated with a health condition or a predisposition to a health condition, include, but are not limited to, polymorphic alleles associated with a neurodegenerative disorder, a neurological disorder, an eye disease, a mood disorder, a respiratory disease, a cardiovascular disease, an immunological disorder, a hematological disease, a metabolic disorder, or a drug sensitivity condition. Some examples of polymorphic alleles associated with a health condition are provided in Table 3 above. Polymorphic alleles may include polymorphic alleles in an encoded protein or a regulatory sequence affecting the expression of the encoded protein. In some cases, the encoded protein is a drug target. Examples of drug target proteins include, but are not limited to, GPCRs, ion channels, kinases, enzymes, and transcription factors.

In other embodiments, the one or more polymorphic alleles are pre-selected based on the presence of a high degree of surrounding linkage disequilibrium in the genome, which has been proposed as a signature of genomic loci that are likely to impact many common health conditions. Methods for identifying SNPs having a high surrounding linkage disequilibrium and genes near such SNPs are described in, e.g., Wang et al (2006), *Proc Natl Acad Sci USA,* 103(1):135-140.

In some cases, a panel of iPSC lines includes iPSC lines generated from subjects that are diagnosed as suffering from one or more health conditions. The one or more health conditions may be one or more health conditions that are common to all of the iPSC donors, or they may be health conditions that are different between the iPSC donors.

In certain cases, a panel of iPSC lines includes iPSC lines generated from subjects that are both diagnosed as suffering from a health condition and carry a polymorphic allele associated with a health condition, e.g., a polymorphic allele associated with the diagnosed health condition.

A panel of iPSC lines may include iPSC lines from at least about 10 individuals to at least about 50,000 individuals, e.g., 10 to 50, 20 to 100, 50 to 250, 100 to 1000, 250, to 2000, 500 to 5000, 1000 to 10,000, 2500 to 20,000, 10,000, to 30,000, 20,000 to 40,000, or 30,000 to 50,000 individuals.

A panel of iPSC lines may include iPSC lines from at least two ethnic groups, e.g., 3, 4, 5, 6, 7, 8, 9, 10, 12, 15, 20, 25, 30, or 50 ethnic groups. Examples of ethnic groups include, but are not limited to, Europeans, Japanese, Chinese, and the Yoruba of Nigeria, and ethnic groups listed in Table 4.

TABLE 4

Exemplary Ethnic Groups

Africa

Bantu
Biaka
Mandenka
Mbuti pygmy
Mozabite
San
Yoruba
Native America

Colombian
Karitiana
Maya
Pima
Surui
Asia
Ctrl/South

Balochi
Brahui
Burusho
Hazara
Kalash
Makrani
Pathan
Sindhi
Uyghur
Western Asia

Bedouin
Druze
Eastern Asia

Cambodian
Dai
Daur
Han (N. China)
Han (S. China)
Hezhen
Japanese
Lahu
Miao
Mongola
Naxi
Oroqen
She
Tu
Tujia
Xibo
Yakut
Yi
Europe Adygei
Basque
French
North Italian
Orcadian
Russian
Sardinian
Tuscan
Oceania Melanesian
Papuan IV. Methods for Use of Induced Stem Cell Lines and Panels of Induced Stem Cell Lines A. Overview The iPSC lines and panels of iPSC lines described herein are useful in a number of methods relating to drug discovery and development. Typically, a drug candidate compound will be evaluated in a biochemical assay (e.g., a receptor binding assay) that evaluates only a single or very few sequence variants of the drug target expressed in a patient population. Thus, such assays provide little information as to how effective the drug candidate compound is likely to be in patients that express a drug target allele that differs from the particular drug target allele that was originally screened. Along the same lines, drug candidate compounds often undergo functional cellular screens in one or few cell lines engineered to express a specific allele of the drug target, again ignoring the genetic diversity of a human patient population not only with respect to the drug target itself, but also to that of the various downstream signal transduction proteins that play a role in the response endpoint of cells to a drug. Likewise, adverse effects of candidate drug compounds (e.g., liver toxicity) are generally evaluated in inbred animal models, which are likely to be uninformative for a variable fraction of a human patient population. In contrast, drug screening in panels of genetically diverse iPSC lines, as described herein, addresses the lack of genetic diversity in the prevailing drug screening models.

The panels of genetically diverse iPSC lines described herein (e.g., human iPSC lines) or cells differentiated from panels of genetically diverse iPSC lines, as described herein, may be used to identify test compounds that act on a drug target of interest. In some embodiments, the panels of iPSCs cell lines include a sufficient number of iPSC lines such that at least two, e.g., at least 3, 5, 10, 20, 50, 100, or 200 polymorphic alleles of a drug target (e.g., a GPCR, ion channel, or kinase) are represented in the panel. In some embodiments, panels of iPSC lines are derived from subjects diagnosed as suffering from a health condition or identified as having a predisposition to the health condition. In other embodiments, the iPSC line panels comprise iPSC lines each of which that has at least one polymorphic allele associated with a health condition or a predisposition to the health condition.

Drug targets for many health conditions are known. Such drug targets may include, but are not limited to, receptors, GPCRs, growth factor receptors, neurotransmitter receptors, ion channels, enzymes, protein kinases, proteases, cytoskeletal proteins, and transcription factors. Test compounds can be assayed for their effect on a drug target by a number of assays known in the art. Such assays include cell-based assays including, but not limited to, assays for determining second messenger levels, e.g., intracellular calcium, cAMP, cGMP, arachidonic acid, and inositol phosphates; channel currents; apoptosis; proliferation; morphological changes; changes in adhesion. Examples of cell-based assays include, but are not limited to those described in, U.S. Pat. Nos. 7,319,009, 7,288,368, and 7,238,213, Cell based assays may also include determining the cellular localization of one or more proteins (e.g., protein kinases, receptors, and transcription factors) in cells in the presence or absence of a test compound. Test compounds may also be screened for their ability to alter a gene expression profile by any gene expression profiling method known in the art. In some cases, the cells to be screened may be genetically modified to express one or more reporter proteins that can indicate activation of a signaling pathway. For example protein-protein interactions between fusion proteins introduced into cells may be detected by a number of methods known in the art, e.g., by fluorescence resonance energy transfer (FRET) or enzyme fragment complementation.

In some cases, the mechanistic basis of a sporadic form of a disease is a combination of genetically-determined cell type-specific phenotype and epigenetic factors (e.g., oxidative stress). In other words, iPSC-derived differentiated cells from a patient with a sporadic form of a disease (e.g., Parkinson's) may bear a genetic predisposition to a pathological or pre-pathological cellular phenotype (e.g., apoptosis), but the phenotype may only manifest in vitro in the presence of an appropriate "stressor" that recapitulates environmental epigenetic factors associated with the sporadic disease or a cellular phenotypes that precede a clinical manifestation of the disease (e.g., mitochondrial dysfunction, oxdidative stress, or nitrosylative stress). Accordingly, in some cases disease-relevant cellular phenotypes are induced by a stressor. Examples of stressors include, but are not limited to cellular oxidative stress, nitrosylative stress, proteasome inhibition, inhibition of mitochondrial electron transport, translation inhibition, decreased calcium buffering, high osmolarity, heat shock, heavy metals (e.g., Zn, Mn, Fe, Cd, Al, or Pb), protein misfolding. Examples of agents that induce, increase, or result from oxidative stress include, but are not limited to, $H_2O_2$, ascorbic acid/$FeSO_4$, 4-hydroxynonenal, glutamate, kainate, NMDA, dopamine, okadaic acid, $A\beta^{1-42}$ and isocyanate. Proteasome inhibitors include, but are not limited to lactacystin, ziram, MG 132, and carbobenzoxy-L-isoleucyl-gamma-t-butyl-L-glutamyl-L-alanyl-L-leucinal (PSI). Mitochondrial stressors include, but are not limited to, rotenone, 3-nitropropionic acid (NPA), 1-methyl-4-phenylpyridinium (MPP+), antimycin, paraquat, methylglycoxal, and cyanide. Nitrosylative stressors include, but are not limited to, ($\pm$)-S-nitroso-N-acetylpenicillamine, sodium nitroprussiate, and peroxynitrite.

In some cases, the stressor is provided by expressing or overexpressing an exogenous wild type or mutated gene and/or protein. Examples of such genes include, $\alpha$-synuclein, amyloid beta, $A\beta^{1-42}$, Parkin, Pink1, Leucine-rich repeat kinase 2 (LRRK2), superoxide dismutase (SOD).

Assays of drug candidate compounds in an iPSC line or a panel of iPSC lines can include determining a dose-response. In some embodiments, the dose response of an iPSC line or that of one or more types of cells differentiated from the iPSC line provides an indication that of the likely efficacy of the compound in the corresponding iPSC donor. In some embodiments, the fraction of iPSC lines in a panel of iPSC lines that exhibit an acceptable dose-response to a test compound indicates an expected probability of an acceptable dose-response relationship in the target patient population of interest. In some cases, cell-based assays of drug candidate include a comparison of responses obtained in a panel of iPSC lines or iPSC-derived cells to one or more reference iPSC lines or cells that serve as a positive or negative control for the effect of a drug candidate compound. The reference iPSC lines or cells may be from a healthy iPSC donor, from an iPSC donor diagnosed as suffering from a health condition, or an iPSC donor carrying a polymorphic allele associated with a health condition. In other embodiments, assays of drug candidate compounds in an iPSC line or a panel of iPSC lines can include determining effective concentrations, maximum tolerated dose and minimum effective concentration. Additional methods and assays are disclosed in U.S. application No. 61/061,594; filed Jun. 13, 2008; First Inventor Kazuhiro Sakurada, hereby incorporated by reference.

In some cases, the drug screening may be conducted on cells differentiated from iPSCs. Examples of such differentiated cells are described herein (e.g., hepatic cells, neural stem cells, neurons, pancreatic beta cells, cardiomyocytes, hepatic stem cells, oligodendrocytes). The drugs may be targeted to treat a specific disease or condition, e.g., a disease or condition described herein. For example, the iPSCs may be differentiated into dopaminergic neurons, which are used to screen drugs for Parkinson's disease. In other cases, neurons or neural stem cells differentiated from iPSCs may be used to screen drugs for treating Alzheimer's disease, multiple sclerosis, or other neurological disorders. In some cases the In other cases, the iPSCs may be transplanted directly into an immunocompromised animal, e.g., SCID mouse, which is then used to establish in vitro or in vivo assay systems that mimic physiologic conditions in humans or other animals. The in vitro or in vivo assay systems may be used to screen for drugs, e.g., drugs for Parkinson's disease, or as a means to identify biological mechanisms.

Screening of test compounds may also be conducted in iPSC-derived cells when an abnormal cellular phenotype (e.g., abnormal cell morphology, gene expression, or signaling), associated with a health condition or a predisposition to the health condition is known, but a drug target has not yet been identified. Such assays may include contacting a test population of iPSC-derived cells from one or more iPSC donors with a test compound and contacting with a negative control compound a negative control population of iPSC-derived cells from the same one or more iPSC donors. The assayed cellular phenotype associated with the health condition of interest in the test and negative control populations can then be compared to a normal cellular phenotype. Where the assayed cellular phenotype in the test population is determined as being closer to a normal cellular phenotype than that exhibited by the negative control population, the drug candidate compound is identified as normalizing the phenotype. A normal cellular phenotype with respect to a particular health condition or a predisposition for a health condition may be established in iPSC-derived cells from iPSC donors that do not suffer from the health condition or a predisposition for the health condition.

Test compounds identified as lead compounds, may be tested on a panel of iPSC-derived cells in a manner analogous to a clinical trial. In some cases, the efficacy of the lead compound versus a negative control compound, e.g., a placebo compound is determined in a panel of iPSC-derived cells from patients suffering from the same health condition. Preferably, such a panel of iPSC-derived cells is from subjects that are genetically diverse. For example, such patients may be carry at least one polymorphic allele that is unique among the iPSC-derived cells to be included in the panel, e.g., 5 to 10, 20 to 50, 50 to 200, 200 to 500, 500 to 1000, 1000 to 5000, 5000 to 20000, or 20000 to 50000 polymorphic alleles that are unique within the panel of iPSC lines. A number of methods for quantifying the genetic diversity of a population are known in the art, e.g., the analysis of molecular variance (AMOVA) and generalized analysis of molecular variance (GAMOVA). See, e.g., Excoffier et al (1992), *Genetics*, 131: 479-491; Nievergelt et al (2008), *PLOS Genetics*, 3(4):e51. Various clinical experimental designs known in the art may be used for comparing the effect of a lead compound versus a negative control compound. See, e.g., Chow et al (2004) "Design and Analysis of Clinical Trials: Concepts and Methodologies," John Wiley & Sons, Inc., Hoboken, N.J.

The efficacy of the lead compound in iPSC-derived cells may be determined based on any cellular response endpoint, e.g., a response obtained in any of the cell-based assays or gene expression profiling assays mentioned herein.

In some cases, potential adverse effects of a lead compound are tested on a panel of iPSC-derived cells. The iPSC-derived cells may include any cell type that hepatocytes, cardiomyocytes, neurons, Drug candidate compounds may be individual small molecules of choice (e.g., a lead compound from a previous drug screen) or in some cases, the drug candidate compounds to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al. (1994), *J. Med. Chem* 37(9), 1233. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al. (1993), *Proc. Natl Acad. Sci. U.S.A.* 90, 6909; analogous organic syntheses of small compound libraries, as described in Chen et al. (1994), *J. Amer. Chem. Soc.,* 116: 2661; Oligocarbamates, as described in Cho, et al. (1993), *Science* 261, 1303; peptidyl phosphonates, as described in Campbell et al. (1994), *J. Org. Chem.,* 59: 658; and small organic molecule libraries containing, e.g., thiazolidinones and metathiazanones (U.S. Pat. No. 5,549,974), pyrrolidines (U.S. Pat. Nos. 5,525,735 and 5,519, 134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

B. Individualized Drug Therapy and Failed Drug "Rescue"

iPSC cell lines and iPSC-derived cells generated from a subject (e.g., a human subject) can be used to determine the likelihood that a particular drug will have sufficient efficacy in that subject and, if so, an appropriate dose range for that subject. This process is illustrated schematically in FIG. 3. iPSC-derived cells from a subject, e.g., differentiated iPSC-derived cells may be exposed ex vivo to a drug to be tested, and then assayed for their phenotypic response to the drug as described herein. The response of the iPSC-derived cells may be compared to a reference response obtained in iPSC-derived cells from one or more individuals in which the drug has been shown to be effective and/or a reference response in iPSC-derived cells from subjects in which the drug was found to be ineffective. In some cases, the subject to be tested is a subject suffering from a health condition or a predisposition to the health condition. For example, where the subject is suffering from a health condition, and multiple drugs are available to treat the health condition, the efficacies and adverse effects of the multiple drugs may be evaluated iPSC-derived cells from that individual. Preferably, the iPSC-derived cells used to test drug efficacy include cells that express at least one drug target (e.g., a neurotransmitter receptor). In other cases, the subject is not suffering from a health condition. In one embodiment, drugs for various health conditions are tested preemptively in iPSC-derived cells from a healthy subject to establish a pharmaco-phenomic profile for that subject. The pharmaco-phenomic profile may subsequently be used as needed for selecting optimal drugs and drug dosing for treatment of the particular subject.

C. Disease Pathway and Target Discovery

For many diseases, especially those that have primarily a sporadic form (e.g., Parkinson's disease), the underlying cellular phenotype(s) that precede and eventually result in pathology are unknown. In fact, for progressive degenerative conditions, it is likely that a causative or predictive cellular phenotype occurs well before the first manifestation of symptoms. However, for many types of diseases the relevant cells (e.g., neurons, cardiomyocytes, and pancreatic cells) are not directly accessible for analysis. Thus, depending on the cell type affected by a particular disease, it has not been possible to compare live cells from patients to those of normal subjects in order to identify disease-relevant, cellular phenotypes that cause or predispose for a disease. Identification of reproducible cellular phenotype differences between patient iPSC-derived and normal subject iPSC-derived cells allows the development of screening assays to identify candidate therapeutic agents. Candidate therapeutic agents are those that normalize a disease-associated cellular phenotype, i.e., alter the relevant cellular phenotype in the patient-derived cells so that it is closer to the corresponding cellular phenotype in cells derived from normal subjects under the same conditions. Alternatively, the therapeutic agent may alter a cellular phenotype of patient-derived iPSCs so as to protect them from a stressor, as described herein.

Sets of data representing various cellular phenotypes (e.g., mitochondrial ROS production, expression profiles, protein aggregation) in patient iPSC-derived cells versus normal subject iPSC-derived cells constitute vectors in a multidimensional space, amenable to analysis by means of multivariate and univariate statistical and machine learning techniques. Thus cellular phenotypes distinguishing patient versus normal subject can be identified, for example, by means of univariate statistical methods, such as t-test, ANOVA, regression, as well as their non-parametric analogs. In some embodiments, cellular phenotype data are further filtered using various statistical criteria, e.g., p-value of significance (Type1 error), effect size, etc. Sets of cellular phenotypes which differ significantly between disease and normal states are further scrutinized by biological pathways analysis. In many cases, a pathway enrichment analysis is performed to further narrow the set of cellular phenotypes which are the most disease-informative. A number of statistical procedures such as Hypergeometric statistic, Kolmogorov-Smirnoff test, etc, can be used to perform pathway enrichment analysis.

In some cases, cellular phenotypes that are found to differ significantly in patient versus normal subjects (i.e., disease-relevant cellular phenotypes) need to be validated by means of orthogonal assays. In other cases, the identified disease-relevant cellular phenotypes are confirmed by performing validation/cross-validation analysis on the independent data sets from the same type of cellular phenotype assays. In some embodiments, disease-relevant cellular phenotypes are determined by first assaying and analyzing only a portion of the available patient and normal iPSC lines, and then validating disease-relevant cellular phenotypes in the remaining iPSC lines. In other embodiments, where it is not feasible to utilize independent sets of iPSC lines for disease-relevant cellular phenotype discovery versus validation, other statistical approaches, such as k-fold cross-validation techniques, are used instead. In some cases, one or more validated cellular phenotypes is then used to assess test agents for their ability to convert one or more cellular phenotypes reflecting a disease condition to cellular phenotypes reflecting a normal condition.

Where the disease under study is a progressive condition with a potentially late onset (e.g., age 60 and over), selection of "normal" control subjects is non-trivial, as it is usually not possible to know, prospectively, who will develop a progressive degenerative disorder. In other words, subjects that are apparently normal at a given age/time point (e.g., when a biopsy is obtained for iPSC derivation) may eventually develop the disease for which an associated cellular phenotype is sought. Thus, cells derived from such a subject would not be a valid "normal" control. Accordingly, in some embodiments, rather than selecting an age-matched normal control subject, a "wellderly" subject is selected for normal control iPSC derivation. As used herein, a "wellderly" subject refers to any subject that is at least 80 years old and has not suffered from any major chronic diseases. Selection of wellderly individuals as normal control subjects makes it statistically less likely that such individuals will go on to develop a degenerative condition. Thus, iPSCs derived from such individuals are less likely to exhibit a cellular phenotype that is associated or predictive of the disease being analyzed, and therefore provide a more reliable "normal control" phenotype for purposes of comparison to patient-derived iPSCs and iPSC-derived cells. In other embodiments, elderly individuals are selected for control iPSC generation that while not having suffered from a degenerative disease under study, may have suffered other unrelated degenerative diseases. In other cases, age-matched subjects free of the disease to be analyzed are used to generate normal control subject iPSCs.

Figure 4:
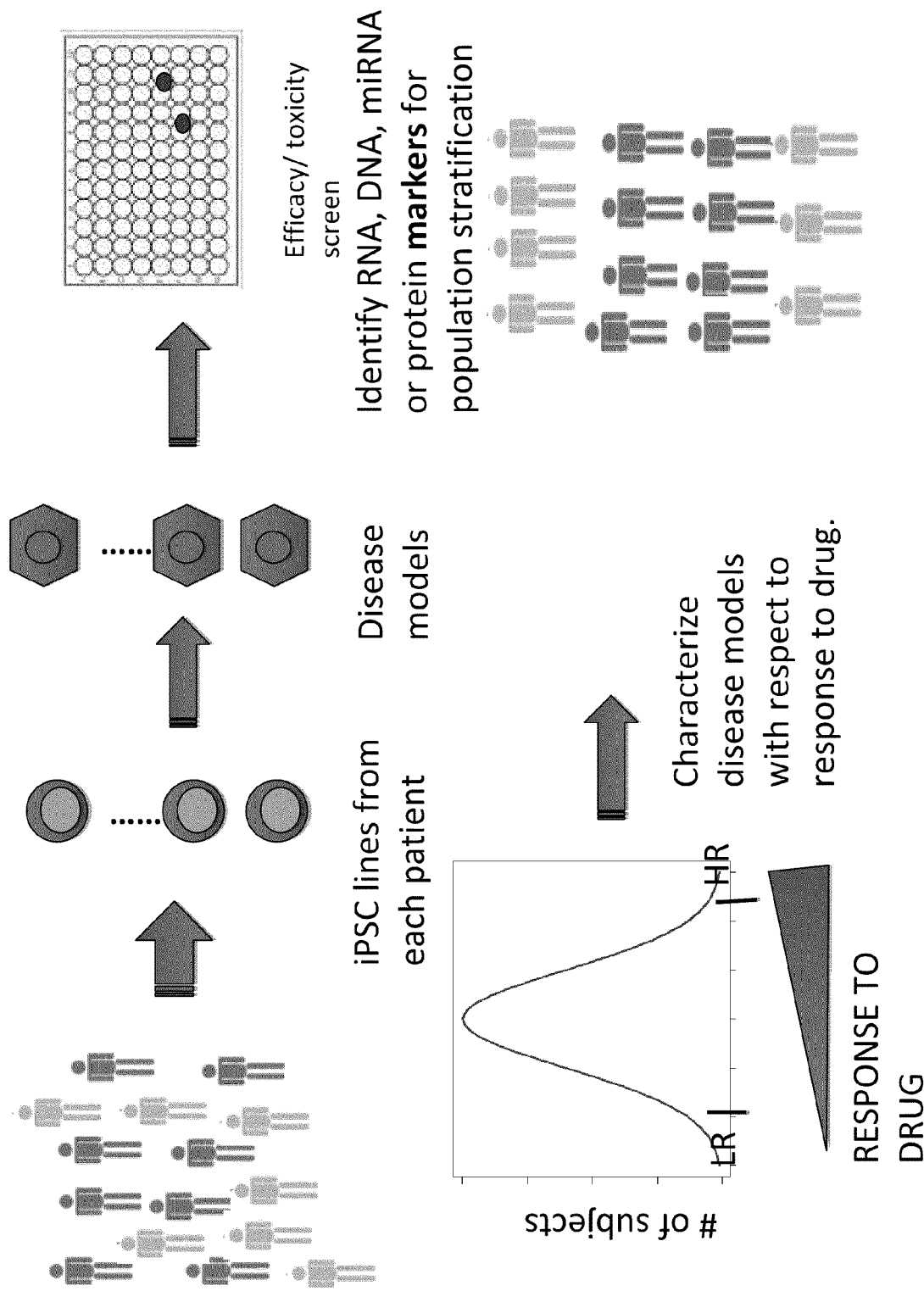
FIG. 4 is an overview of an exemplary, non-limiting, scheme for patient iPSC-based identification of predictive biomarkers for drug efficacy and toxicity. Such biomarkers are used in, e.g., patient stratification for clinical trials of drug candidates, and also for optimal dosing and safety of approved therapeutics in specific patients or patient populations, which is sometimes referred to as "personalized medicine."

In some cases, once a candidate therapeutic agent has been identified as effectively normalizing a cellular phenotype in a small number of patient iPSC lines and cells derived therefrom, efficacy is tested in larger panels of patient iPSC-derived cells to identify potential variation in efficacy or toxicity of the candidate therapeutic agent. In some cases, efficacy is tested in iPSCs or iPSC-derived cells from at least about 20 to about 500 patients, e.g., at least about 25, 30, 40, 50, 60, 70, 100, 200, 250, 300, 400, or another number of patients from at least about 20 to about 500 patients. In some embodiments, biomarkers associated with responsiveness to a candidate therapeutic agent or lack of responsiveness to a candidate therapeutic agent are identified and used to stratify a patient population into, e.g., "high responders" (HR) and "low responders" (LR), as schematized in FIG. 4. In some cases, biomarkers are used to identify suitable patients for clinical trials of a candidate therapeutic agent. In other cases, biomarkers are used to predict the responsiveness or potential toxicity of a therapeutic agent for particular patients. In some cases, biomarkers include genomic biomarkers (e.g., SNPs, CNVs, or other genetic polymorphisms). In other cases, the biomarkers include an expression profile signature (e.g., an mRNA expression profile). The biomarkers may include a protein expression profile or even a single protein expression level. In some cases, where the biomarkers are expression profile biomarkers, these may be determined directly from a patient sample (e.g., blood, urine, sputum, hair, skin, or other biological sample taken directly from the patient). In other embodiments, expression profile biomarkers, are specific to patient iPSCs or iPSC-derived cells in which the candidate therapeutic agent or therapeutic agent is tested.

Thus, in some embodiments, iPSCs are derived from patients and control subjects, and the iPSCs are differentiated into disease-relevant cell types thereby allowing a comparison of cellular phenotypes in patient-derived cells versus normal subject derived cells. For example, the cellular phenotype that is compared may include a mitochondrial phenotype, e.g., ATP synthesis, ATP/ADP ratio, mitochondrial potential, calcium buffering, production of reactive oxygen species, mitochondrial fusion and fission, mitochondrial morphology, and mitochondrial movement. In other cases, the cellular phenotype that is compared is the fraction and rate at which a particular cell type is undergoing apoptosis in the presence of a stressor. In some embodiments, the cellular phenotype is protein aggregation (e.g., the formation of lewy bodies). In other embodiments, gene expression (e.g., microRNA expression) is compared between patient-derived cells and normal subjects.

In some cases, relational databases are constructed that integrate multiple data streams relating to each patient and control iPSC line. These data include, but are not limited to, one or more of the following: patient medical history and family medical history, patient medical data (e.g., blood pressure, liver enzyme levels), patient adverse drug reactions, patient drug responsiveness, partial or complete genomic sequence, sequence of all genes with known disease-associated alleles, comprehensive SNP genotypes (e.g., genotypes for all SNPs with known disease associations), gene copy number variation (CNV) polymorphisms, expression profiles for iPSCs and for cells differentiated from the iPSCs (e.g., dopaminergic neurons, cortical neurons, motor neurons, pancreatic cells, hepatocytes, cardiomyocytes, and vascular epithelial cells) under resting and under various stimulus paradigms (e.g., in the presence of a stressor), all cellular phenotype assay data used for initial pathway discovery and for drug screening, including, e.g., cellular phenotype data in the presence or absence of test compounds and compounds with known pharmacological properties (e.g., a cholinesterase inhibitor, a receptor ligand, a kinase inhibitor etc.). In some embodiments, a user can query such a database based on any set of criteria with user define limits. For example, a user may wish to identify polymorphisms associated with patients whose iPSC-derived dopaminergic neurons did or did not respond to a candidate therapeutic agent. In another example, a user may wish to identify a common gene expression profile that distinguishes motor neurons that showed a severe apoptotic response to a stressor versus a mild apoptotic response, etc. Such databases are very useful for data mining and establishing robustly predictive signatures for specific disease states and their response to candidate therapeutic agents.

EXAMPLES

Example 1

Generation of iPSC Lines from Patients Suffering from Spinal Muscular Atrophy

Spinal Muscular Atrophy (SMA) is a neuromuscular disease characterized by degeneration of motor neurons that is among the leading causes of childhood paralysis and mortality. The disease exhibits a wide range of severity affecting infants through adults, and is subdivided into types I-IV based on the age of onset and severity of symptoms: Type I "Infantile" onset at ages 0-6 months and generally fatal); Type II "Intermediate," onset at ages 7-15 months; inability to stand or walk, but some ability to maintain a sitting position; Type III "Juvenile" onset at ages 18 months to 17 years, with some ability to walk, though potentially transient; Type IV "Adult," some muscle weakness, but no genetic basis is known.

The molecular basis of SMA is linked to the Survival Motor Neuron (SMN) gene. The region of chromosome 5 that contains the SMN (survival motor neuron) gene has a large duplication. A large sequence that contains several genes occurs twice—i.e. once in each of the adjacent segments. The two copies of the gene—known as SMN1 and SMN2—differ by only a few base pairs. The SMN2 gene contains a mutation that occurs at the splice junction of intron 6 to exon 7 resulting in about 90% of SMN2 pre-mRNA transcripts being spliced into a form that excludes exon 7. This shorter mRNA transcript codes for a truncated SMN protein, which is rapidly degraded. About 10% of pre-mRNA transcript from SMN2 is spliced into the full length transcript that codes for the fully functional SMN protein. This splicing defect occurs in multiple cell types, although, for unknown reasons, the survival of motor neurons appear to be particularly affected.

SMA results from the loss of the SMN1 gene from both chromosomes, and its severity, ranging from SMA 1 to SMA 3, largely depends on whether the level of $SMN2^{E7}$ transcript can make up for low levels or absence of exon 7-inclusive SMN 1 transcript. The mutations that cause the loss of SMN 1 are of two types. Deletion mutations, in which both copies of the SMN1 are missing. The other type of mutation is a conversion mutation in which both copies of the SMN1 gene have a point mutation resulting in the same splicing pattern as the SMN2 gene. As an initial step towards developing an in vitro assay for identifying molecules that can increase levels of exon 7-inclusive SMN2 ($SMN2^{E7}$) transcript, we generated several iPSC lines from Coriell fibroblast lines established from three $SMN1^{-/-}$ SMA patients and from two healthy $SMN1^{-/+}$ subjects.

Induction of iPSCs was initiated by transduction of $SMN1^{-/-}$ and $SMN1^{-/+}$ fibroblast cultures with four MoMLV VSV-G-pseudotyped viruses for expression of human OCT4, SOX2, KLF4, and c-MYC, each at an MOI of about 10. Five days after viral transduction, fibroblasts were switched from human fibroblast medium into human ES cell supportive medium and monitored daily for the appearance of putative iPSC colonies based on morphological criteria.

Figure 5:
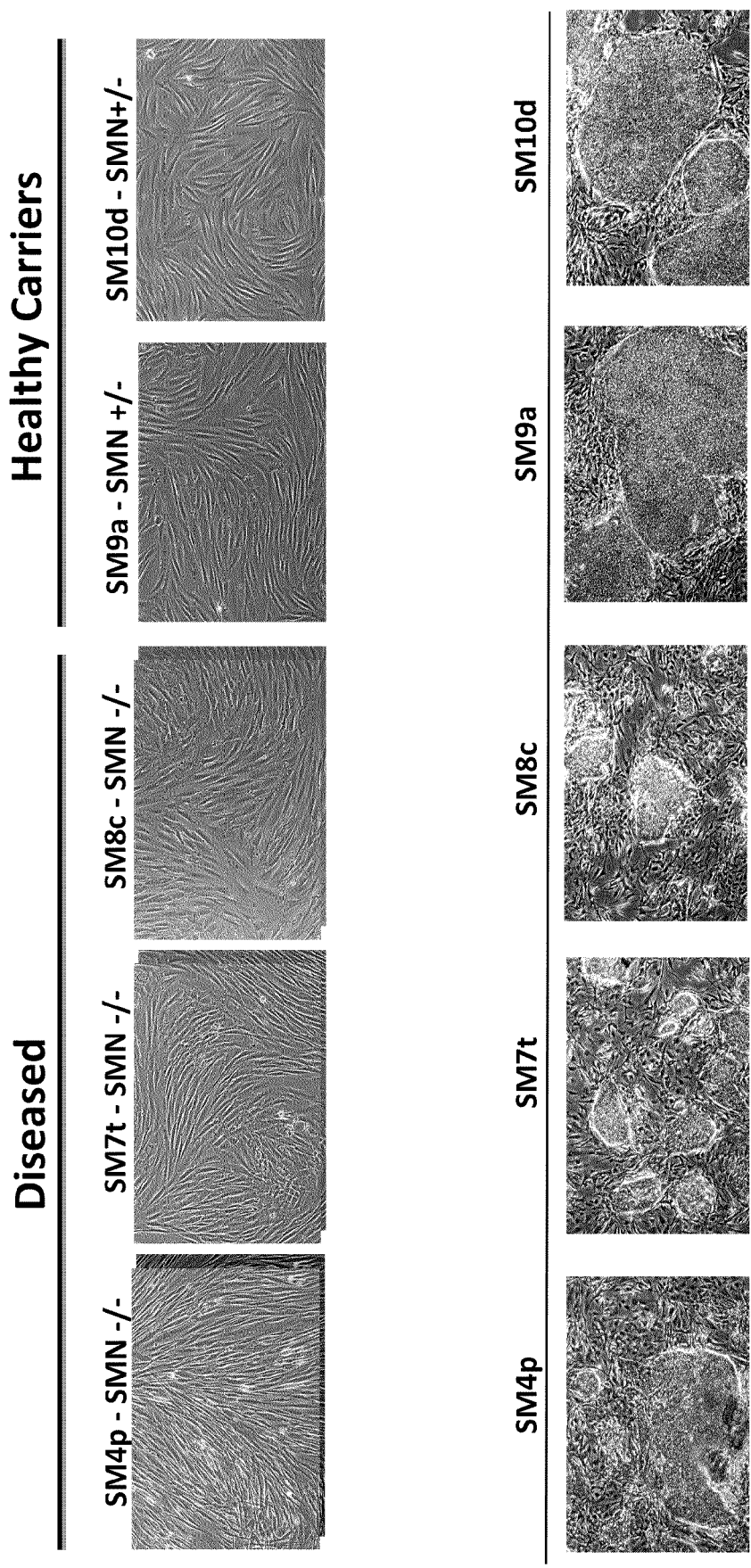
FIG. 5 (Top Panel) shows photomicrographs of fibroblasts from three SMN1$^{-/-}$ SMA patients and two SMN1$^{-/+}$ healthy control subjects; (Bottom Panel) shows photomicrographs of iPSC colonies derived from the corresponding SMA case and control subject fibroblasts illustrated in the top panel.
Figure 6:
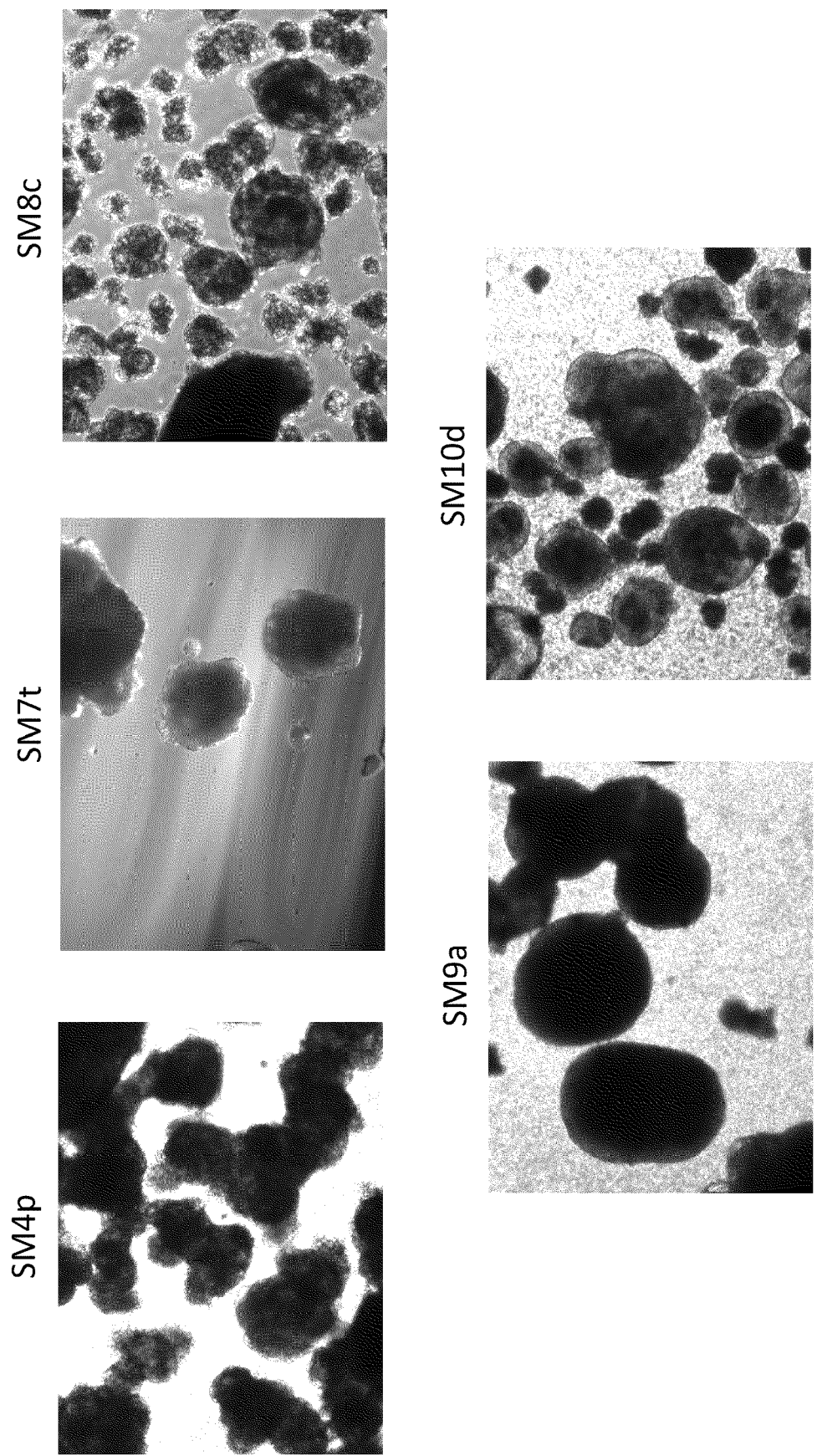
FIG. 6 shows photomicrographs of embryoid bodies obtained from the SMA case and control iPSC lines shown in FIG. 5.

Initial putative SMA-iPSC colonies were picked after approximately three weeks and propagated clonally in the presence the presence of the ROCK inhibitor Y-27632 (10 µM) Calbiochem) to derive the $SMN1^{-/-}$ iPSC lines SM4p, SM7t, and SM8c, and the $SMN1^{-/+}$ iPSC lines SM9a and SM10d, as shown in FIG. 5. Each of the iPSCs expressed the pluripotency associated markers, Nanog, Oct4, SSEA3, SSEA4, TRA1-60, and TRA1-81 (data not shown) as determined by immunocytochemistry. Q-PCR analysis showed that these iPSC lines expressed endogenous Oct 4, Sox2, and Klf4, but not the exogenous Oct4, Sox2, and Klf4 introduced by viral transduction. In addition, Q-PCR analysis also demonstrated expression of Nanog, SSEA-3, SSEA-4, TRA1-60, TRA1-81, DNMT3B, FOXD3, LIN28, ZNF206, LEFT2, TDGF1, and TDGF2 in all of the iPSC lines (data not shown). Importantly, all of the SMA iPSC lines were able to form embryoid bodies (EBs) as shown in FIG. 6, which indicated that these lines had good potential for differentiation as is expected for iPSCs. Indeed, the ability of the SM8c line to differentiate into ectodermal, mesodermal, and endodermal lineages in vitro was confirmed by immunostaining for the ectodermal marker TuJ1, the mesodermal marker Desmin, and the endodermal marker AFP, as shown in FIG. 7. Further, the SM8c iPSC line was shown to differentiate into mature motor neurons as shown by double immunolabeling for Islet and Neuro-N (data not shown).

Based on these results, we concluded that iPSCs can be generated from SMA patients and differentiated into motor neurons, as required for the screening assay described in Example 2.

Example 2

Assay for Identification of Molecules that Improve Molecular and Cellular Disease Phenotypes in Motor Neurons from Patients Suffering from Spinal Muscular Atrophy We seek to identify molecules that increase the level of $SMN2^{E7}$ transcript in motor neurons derived from patients suffering from SMA. In principle, increased levels of $SMN2^{E7}$ transcript can be increased by boosting SMN2 transcription, reducing degradation of SMN2 mRNA, or by increasing the fraction of SMN2 pre-mRNA that is spliced into $SMN2^{E7}$ mRNA. SMA patient-specific motor neurons are obtained by first generating panels of iPS cell lines from Type I, Type II, and Type III SMA patients, as described in Example 1, and subsequently differentiating iPSCs into motor neurons. Prior to motor neuron differentiation SMA patient SMN2 minigene reporter iPSC lines are established to provide a convenient readout for the level of $SMN2^{E7}$ transcript in motor neurons.

Following parental informed consent, standard dermal punch biopsies 2-4 mm in diameter and thickness are obtained from approximately 30 Type I, 30 Type II, and 30 Type III SMA patients, all of whom have an $SMA1^{-/-}$ genotype, and 10 healthy, age-matched control subjects that have an $SMA1^{-/+}$ genotype. For each SMA-iPSC line to be generated, the following corresponding patient information is collected and annotated in an iPSC line database: disease severity ranking (i.e., Type I, II, or III), age of disease onset, patient medical history, family medical history including incidence of ALS, blood level of SMN protein, SMN1 and SMN2 genotypes, MUNE Motor Unit Number Estimation, Hammersmith SMA Functional Motor Scale ranking, breathing test evaluation (only for children>5 yrs), symptom progression evaluation (e.g., how outcome of motor tests has changed over time), muscle mass index, description of therapeutic interventions to date, and therapy response. Additional data may be added to each record as they are acquired, including, e.g., SMN protein levels and $SMN2^{E7}$ transcript levels under various experimental conditions (e.g., in the presence or absence of a candidate therapeutic compound), informative SNP genotypes, genomic sequence, and tissue/cell-type specific expression profiles.

Biopsy samples are stored for up to 5-7 days at 4° C. in a "biopsy medium" containing KO-DMEM and supplemented with 10% fetal bovine serum (FBS), Earl's Salts, nucleosides, beta-mercaptoethanol (BME), non-essential amino acids, glutamine, and penicillin/streptomycin. Biopsies are minced into 4-5 pieces, and the pieces are then transferred to a 60 mm dish. The pieces are then "sandwiched" under an acid-washed coverslip and cultured in biopsy medium for five days. Subsequently, the sandwiched biopsy explants are cultured in human fibroblast ("hFib") medium containing KO-DMEM, Earl's Salts, 10% FBS, glutamine, penicillin/streptomycin, and medium is replaced every 3-4 days until the coverslip is confluent. SMA iPSCs are generated, as described in Example 1, from fibroblasts obtained from each biopsy.

An SMN2 splicing minigene reporter construct is generated that incorporates exons 6, 7, and 8, and utilizing the SMN2 promoter is generated essentially as described in Zhang et al (2001), *Gene Ther.*, 8:1532-1538 and Wilson et al, *Stem Cells and Development*, 16:1027-1041. The SMN2 reporter construct will incorporate the DD-AmCyan1 fluorescent protein reporter to maximize the signal to noise ratio in a compound screening reporter gene assay. The DD-AmCyan1 protein contains a degradation ("DD") domain that conditionally destabilizes the protein thereby keeping "background" levels of the reporter protein prior to a test compound screening assay very low. However, upon addition of the cell-permeable "Shield1" ligand (Invitrogen), which selectively binds to the DD domain, the reporter protein is stabilized and can therefore accumulate. Thus, potential differences in DD-AmCyan1 reporter levels in the presence or absence of test compounds are maximized by measuring almost exclusively reporter protein produced after the beginning of the screening assay, i.e., after the addition of the Shield1 ligand and test compound. Additional reporter constructs will include AmCyan1 or luciferase as the reporter. Other constructs will include the CMV promoter to drive SMN2 minigene expression. The SMN2 reporter construct is then stably transfected into type I, type II, and type III SMA-iPSCs and healthy control (SMN1$^{WT/WT}$) iPSCs to generate SMN2-reporter SMA-iPSC lines of varying disease severity backgrounds, and SMN2 reporter control iPSC lines, respectively. Primary screening of test compounds for the ability to increase properly spliced SMN2 transcript levels is conducted initially in motor neurons derived from Type I SMA reporter iPSCs.

On day 0, confluent 10 cm plates of SMN2 reporter SMA-iPSCs are trypsinized and then washed/resuspended in embryoid body (EB) medium containing KO DMEM (Invitrogen, catalog #10829-018), Knockout Serum Replacement (Invitrogen, catalog #A1099202), Plasmanate (Talecris), Glutamax (Invitrogen, catalog #35050079), non-essential amino acids (Invitrogen, cat #11140050). After washing and resuspension, the cells are plated in ultra-low attachment (ULF) 6-well plates and grown into EBs over the next 4-5 days. On day 5, EBs are washed, gently resuspended in EB medium, and replated in a new ULA 6-well plate, and the wash/replate procedure is repeated on day 8 or 9. On day 11, EBs are collected and resuspended in N2 base medium (DMEM/F12, Glutamax (Invitrogen, catalog #10565), N-2 Supplement (Invitrogen, catalog #17502-048), D-Glucose (Sigma, catalog #G8769), Ascorbic Acid (Sigma, catalog #A4403-100 mG)) supplemented with 1 µM Retinoic Acid (RA) and 100 nM Purmorphamine. (PM). On day 14, EBs are transferred to in N2 Base medium+1 µM RA+1 µM Purmorphamine and replated (3 ml of EB suspension/well) on ULA 6 well plates. N2 base The RA (1 µM)/PM (1 µM)-supplemented EB medium is replaced every 3-5 days, as needed, until approximately day 28. Afterwards, EBs are dissociated by dilute papain treatment and gentle trituration, and then replated on new ULF 6-well plates followed by gentle trituration every 10 minutes over a period of 45 minutes. After dissociation, the resulting cell suspension is collected and transferred to a 50 ml conical tube containing motor neuron maturation medium (DMEM/F12, Glutamax, N-2 Supplement (Invitrogen, catalog #17502-048), B-27 Supplement (Invitrogen, catalog #17504-044), D-Glucose, Ascorbic Acid (Sigma, catalog #A4403-100 mG), 2 ng/mL each GDNF (R&D, catalog #212-GD), BDNF (R&D, catalog #248-BD), and CNTF (R&D, catalog #257-NT/CF). The cell suspension is pelleted by centrifugation at 1000 RPM for five minutes, and is then resuspended in motor neuron maturation medium at a cell concentration of approximately $1.6 \times 10^6$ cells/ml. Aliquots (50 µl) of cell suspension are then plated on laminin-coated wells of optical grade 96 well plates. Beginning on day 31, half-medium changes are conducted every other day or every day depending on how quickly the medium becomes spent. The differentiated cultures are maintained in motor neuron differentiation medium for another four weeks prior to beginning SMN2-reporter assays to allow expansion and maturation of the motor neuron population.

At the beginning of the screening assay, all wells of 96-well plate mature motor neuron (MMN) cultures are incubated in the presence of Shield1 at a final concentration of 1 µM. Test wells are incubated in the presence of test compounds from the NIH Clinical Collection Library (available from BioFocus DPI) at a final concentration of 50 µM. Negative control wells receive no addition or are incubated with a vehicle compound (e.g., DMSO) at a concentration equivalent to that present in some of the test compound solutions. Positive control wells are incubated in the presence of sodium vanadate (50 µM), which has previously been shown to significantly increase levels of SMN2$^{E7}$ transcript (Zhang et al (2001), *Gene Therapy*, 8, 1532-1538). After incubation for 24 hours, cultures are fixed and processed for immunofluorescence detection of Islet 1/2 (mature motor neurons) and Olig2 (motor neuron progenitors) and DD-AmCyan1 fluorescence levels are imaged and quantified in Islet 1/2$^+$ and Olig2$^+$ cells. Compounds that increase SMN2 reporter levels ("candidate therapeutic" compounds) are screened in secondary assays for their ability to increase SMN2$^{E7}$ transcript levels and for their ability to promote SMA motor neuron survival over a period of about two weeks. Candidate therapeutic compounds are then tested on motor neurons derived from additional type I SMA SMN2-reporter iPSC lines, and from type II and type III iPSC lines to validate the effect of the therapeutic candidate compounds on motor neurons from diverse genetic backgrounds extant in the SMA patient population.

It is expected that identification of compounds that increase the net level SMN2$^{E7}$ transcript in patient-derived motor neurons is likely to be more relevant for identification of therapeutic drug candidates for SMA than a similar assay in cell types relatively unaffected or less affected by loss of SMN1 (e.g., fibroblasts) or heterologous cell lines.

Example 3

Generation of iPSC Lines iPSCs from Patients with Idiopathic Parkinson's Disease and Defined Mutations in Genes Associated with Parkinson's Disease Parkinson's Disease (PD) is one of the most common neurodegenerative diseases of aging, affecting 1-2% of the population over 65 years of age. Clinical symptoms include rest tremor, bradykinesia, and rigidity. We seek to generate a PD patient iPSC model to identify candidate therapeutic agents that slow, halt, or reverse PD progression.

iPSC lines are generated from skin biopsies obtained from 10 healthy control subjects with no known family history of PD, 10 patients with sporadic PD, patients each with mutations in the genes that encode α-synuclein (PARK1), parkin (PARK2), PINK 1 (PARK6), or LRRK2 (PARK8) for a total of 10 patients for each mutation. iPSCs are generated as described in Example 1. Afterwards, dopaminergic neurons are derived by differentiating each of the patient iPSC lines and control subject iPSCs. A dopaminergic phenotype is established by immunocytochemical staining for tyrosine hydroxylase positivity, and assaying the differentiated cells for the ability to synthesize and release dopamine. Dopaminergic neurons are obtained by differentiating the iPSCs according to the method of Perrier et al (2004), *Proc Natl Acad Sci USA* 101, 12543-12548. After validating the dopaminergic phenotype of neurons differentiated from each of the above iPSC lines, cultures of the patient iPSC-derived dopaminergic neurons are tested in a battery of cellular phenotype assays and compared to control subject dopaminergic neurons. These are: assays for aggregation of α-synuclein, dopaminergic neuron apoptosis (TUNEL, caspase activation) and necrosis (CytoTox-Glo), oxidative stress indicators (glutathione levels, ROS, and 4-HNE), and mitochondrial dysfunction (ATP content, membrane potential, morphology, and calcium buffering). It is expected that sporadic forms of PD and PD caused by the above-mentioned mutations will exhibit very similar dopaminergic cellular phenotypes in at least some of these assays. Once this is established, one of more of the PD-associated cellular phenotypes is used as the basis of a screen for candidate therapeutic agents that can reverse or ameliorate these cellular phenotypes. Further, it is expected that as the PD cellular phenotypes are identified in disease relevant cells (dopaminergic neurons) from human PD patients, their predictive value and reliability for the development of therapeutic agents will be more robust than those based on heterologous assay models.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying an agent that corrects a phenotype associated with a health condition or a predisposition for the health condition, comprising:
   (i) contacting a first population of isolated cells differentiated from a human induced pluripotent stem cell line, wherein said cells exhibit a phenotype associated with the health condition or predisposition for the health condition, with a candidate agent;
   (ii) contacting a second population of isolated cells differentiated from the human induced pluripotent stem cell line, wherein said cells exhibit a phenotype associated with the health condition or predisposition for the health condition, with a negative control agent;
   (iii) assaying a phenotype in the first population and second population after the contacting steps; and
   (iv) identifying the candidate agent as correcting the phenotype if the assayed phenotype of the first population after the contacting step is closer to a normal phenotype than the phenotype of the second population after the contacting step;
       wherein one or more cells differentiated from the induced pluripotent stem cell line comprise an exogenous Oct3/4 gene, an exogenous Sox2 gene, and an exogenous Klf4 gene;
       wherein the cells in the first and second populations of human induced pluripotent stem cells:
         (a) comprise at least one endogenous allele associated with the health condition or the predisposition for the health condition; or
         (b) are generated from a subject suffering from the health condition or the predisposition for the health condition.

2. The method of claim 1, wherein the health condition is a neurodegenerative disorder, a neurological disorder, a mood disorder, a cardiovascular disease, a metabolic disorder, a respiratory disease, a drug sensitivity condition, an eye disease, an immunological disorder, or a hematological disease.

3. The method of claim 1, wherein the differentiated cells are neural stem cells, neurons, cardiomyocytes, hepatic stem cells, or hepatocytes.

4. The method of claim 1, wherein the phenotype is apoptosis, intracellular calcium level, calcium flux, protein kinase activity, mitochondrial oxidative stress, enzyme activity, cell morphology, receptor activation, protein trafficking, intracellular protein aggregation, organellar composition, motility, intercellular communication, protein expression, or gene expression.

5. The method of claim 1, further comprising comparing a plurality of polymorphic alleles present in the genome of the human induced pluripotent stem cell line to a plurality of polymorphic alleles present in the genome of a human other than the human from which the induced pluripotent stem cell line was generated.

6. The method of claim 1, further comprising genotyping the human induced pluripotent stem cell line for a plurality of polymorphisms.

7. The method of claim 1, further comprising comparing the genome sequence of the human induced pluripotent stem cell line, or a portion thereof, to the genome sequence, or a portion thereof, of a human other than the human from which the induced pluripotent stem cell line was generated.

8. The method of claim 1, further comprising sequencing the genome of the human induced pluripotent stem cell line.

9. A method for assessing the risk of drug toxicity in a human subject, comprising:
   (i) generating iPS cells from one or more isolated somatic cells obtained from the human subject;
   (ii) differentiating the iPS cells obtained in step (i) to obtain one or more isolated differentiated cells;
   (iii) contacting one or more cells obtained in step (ii) with a dose of a pharmacological agent;
   (iv) assaying the contacted one or more differentiated cells for toxicity; and
   (v) determining that there is a low risk for toxicity if the assay is negative for toxicity in the contacted cells; or
   (vi) determining that there is a high risk of toxicity if the assay is positive for toxicity in the contacted cells;
   wherein the differentiated cells comprise an exogenous Oct3/4 gene, an exogenous Sox2 gene and an exogenous Klf4 gene.

10. A method for assessing the efficacy of a dose of a pharmacological agent in a human subject, comprising the steps of:
   (i) generating iPS cells from one or more isolated somatic cells obtained from the human subject;
   (ii) differentiating the iPS cells obtained in step (i) to obtain one or more isolated differentiated cells;
   (iii) contacting one or more cells obtained in step (ii) with the dose of the pharmacological agent;
   (iv) assaying the contacted one or more differentiated cells for a marker of efficacy of the pharmacological agent; and
   (v) determining that the dose of the pharmacological agent is effective if the assay is positive for efficacy in the contacted cells; or
   (vi) determining that the dose of the pharmacological agent is not effective if the assay is negative for efficacy in the contacted cells;
   wherein the differentiated cells comprise an exogenous Oct3/4 gene, an exogenous Sox2 gene and an exogenous Klf4 gene.

11. A method for identifying an agent that is useful as a drug, comprising the steps of:
  (i) contacting one or more isolated cells differentiated from an induced pluripotent stem cell line with a dose of a candidate agent;
  (ii) assaying the contacted one or more differentiated cells for desired efficacy; and
  (iii) identifying the candidate agent as useful if the assay is positive for efficacy in the contacted cells; or
  (iv) identifying the candidate agent as not useful if the assay is negative for efficacy in the contacted cells;

wherein the one or more cells differentiated from the induced pluripotent stem cell line comprise an exogenous Oct3/4 gene, an exogenous Sox2 gene, and an exogenous Klf4 gene.

* * * * *

UNITED STATES PATENT AND TRADEMARK OFFICE
CERTIFICATE OF CORRECTION

PATENT NO. : 8,257,941 B2
APPLICATION NO. : 12/484163
DATED : September 4, 2012
INVENTOR(S) : Sakurada et al.

It is certified that error appears in the above-identified patent and that said Letters Patent is hereby corrected as shown below:

In column 1 (Title page 2 item 56) at line 53, Under U.S. Patent Documents, change "Yamanaka" to --Yamanaka et al.--.

In column 1 (Title page 4 item 56) at line 64, Under Other Publications, change "Proflan" to --Prof Ian--.

In column 2 (Title page 4 item 56) at line 61, Under Other Publications, change "svvith" to --with--.

In column 2 (Title page 6 item 56) at line 9, Under Other Publications, change "256570" to --2565-70--.

In column 1 (Title page 7 item 56) at line 28, Under Other Publications, before "of" insert --Induction--.

In column 1 (Title page 7 item 56) at line 31, Under Other Publications, change "Pluripotericy." to --Pluripotency.--.

In column 1 (Title page 7 item 56) at line 48, Under Other Publications, after "Oncofetal" delete "i".

In column 2 (Title page 7 item 56) at line 47, Under Other Publications, change "Dispensible" to --Dispensable--.

In column 1 (Title page 10 item 56) at line 29, Under Other Publications, change "Nati" to --Natl--.

In the Specification

In column 7 at line 35 (approx.), Change "gangliosidoses," to --gangliosidosis,--.

In column 7 at line 37-39 (approx.), Change "mucopolysaccharidoses, mucolipidoses, mucolipidoeses, mucopolysaccharidoses," to --mucopolysaccharidosis, mucolipidosis,--.

Signed and Sealed this
Third Day of September, 2013

Teresa Stanek Rea
*Acting Director of the United States Patent and Trademark Office*

CERTIFICATE OF CORRECTION (continued)
U.S. Pat. No. 8,257,941 B2

In column 13 at line 32, Change "Butyrlcholine" to --Butyrylcholine--.

In column 13 at line 35, Change "Uridin" to --Uridine--.

In column 15 at line 22, Change "digoxygenin." to --digoxigenin.--.

In column 15 at line 24, Change "digoxygenin," to --digoxigenin,--.

In column 15 at line 36-37, Change "tris-bipyridy" to --tris-bipyridyl--.

In column 16 at line 12, Change "2d" to --2nd--.

In column 17 at line 1, Change "old, 1" to --old,>1--.

In column 17 at line 3, Change "old, 45" to --old,>45--.

In column 19 at line 32, Change "10 min" to --10 minutes, cells--.

In column 20 at line 29, Change "$1^{x}$" to --1X--.

In column 20 at line 30, Change "linoneic" to --linoleic--.

In column 20 at line 38, Change "$1^{x}$" to --1X--.

In column 21 at line 62, Change "non-hematopoeitic" to --non-hematopoietic--.

In column 24 at line 16, Change "metyl" to --methyl--.

In column 24 at line 35, Change "carpoic" to --caproic--.

In column 24 at line 43, Change "RESearch" to --Research--.

In column 24 at line 44, Change "RESearch" to --Research--.

In column 24 at line 45, Change "propinate" to --propionate--.

In column 24 at line 48, Change "RESearch" to --Research--.

In column 26 at line 58, Change "KIF4" to --Klf4--.

In column 28 at line 54, Change "in stead" to --instead--.

In column 32 at line 62, Change "days" to --days.--.

In column 34 at line 47, Change "Indolyphosphate" to --Indolylphosphate--.

In column 36 at line 41, Change "permealize" to --permeabilize--

In column 37 at line 39, Change "karotype" to --karyotype--.

In column 37 at line 46, Change "colecemid" to --colcemid--.

In column 38 at line 53, Change "Micoarray" to --Microarray--.

In column 40 at line 4, Change "cyotkine," to --cytokine,--.

In column 40 at line 13, Change "D'Amouret al." to --D'Amour et al.--.

In column 40 at line 62, Change "108:407-414;;" to --108:407-414;--.

In column 40 at line 67, Change "adipoctyes," to --adipocytes,--.

In column 42 at line 1, Change "before hand," to --beforehand--.

In column 42 at line 19, Change "alles" to --alleles--.

CERTIFICATE OF CORRECTION (continued)
U.S. Pat. No. 8,257,941 B2

In column 45 at line 12-13, Change "environmental epigenetic" to --environmental/epigenetic--.

In column 45 at line 15, Change "oxdidative" to --oxidative--.

In column 45 at line 28, Change "MG 132," to --MG132,--.

In column 45 at line 31, Change "(MPP+)," to --(MPP$^+$),--.

In column 45 at line 32, Change "methylglycoxal," to --methylglyoxal,--.

In column 47 at line 4, Change "neurons," to --neurons.--.

In column 47 at line 26, Change "Natl" to --Natl.--.

In column 53 at line 45, Change "base" to --base.--.

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Gly Arg Lys Lys Arg Arg Gln Arg Arg Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Lys Lys Arg Arg Gln Arg Arg
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ala Arg Ala Ala Ala Arg Gln Ala Arg Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr His Arg Leu Pro Arg Arg Arg Arg Arg Arg
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Arg Arg Ala Arg Arg Arg Arg Arg Arg
1               5                   10
```